US012285543B2

(12) United States Patent
Mandai et al.

(10) Patent No.: US 12,285,543 B2
(45) Date of Patent: Apr. 29, 2025

(54) HUMAN CELL POPULATION COMPRISING HUMAN RETINAL PROGENITOR CELLS WITHOUT AN ISL1 GENE FOR TRANSPLANTATION AND METHODS OF USE THEREOF

(71) Applicants: Riken, Wako (JP); Sumitomo Pharma Co., Ltd., Osaka (JP)

(72) Inventors: Michiko Mandai, Wako (JP); Masayo Takahashi, Wako (JP); Suguru Yamasaki, Kobe (JP)

(73) Assignees: RIKEN, Wako (JP); Sumitomo Pharma Co., Ltd., Osaka (JP)

(*) Notice: Subject to any disclaimer, the term of this patent is extended or adjusted under 35 U.S.C. 154(b) by 48 days.

(21) Appl. No.: 16/463,424

(22) PCT Filed: Nov. 24, 2017

(86) PCT No.: PCT/JP2017/042238

§ 371 (c)(1),
(2) Date: May 23, 2019

(87) PCT Pub. No.: WO2018/097253

PCT Pub. Date: May 31, 2018

(65) Prior Publication Data

US 2019/0351103 A1 Nov. 21, 2019

(30) Foreign Application Priority Data

Nov. 25, 2016 (JP) ................................ 2016-229355
Jul. 14, 2017 (JP) ................................ 2017-138142

(51) Int. Cl.

| | |
|---|---|
| ***C12N 5/00*** | (2006.01) |
| ***A61K 9/70*** | (2006.01) |
| ***A61K 35/30*** | (2015.01) |
| ***A61K 35/545*** | (2015.01) |
| ***A61K 48/00*** | (2006.01) |
| ***A61L 27/38*** | (2006.01) |
| ***A61P 27/02*** | (2006.01) |
| ***C12N 5/0735*** | (2010.01) |
| ***C12N 5/074*** | (2010.01) |
| ***C12N 5/0789*** | (2010.01) |
| ***C12N 5/079*** | (2010.01) |
| ***C12N 5/0793*** | (2010.01) |
| ***C12N 5/0797*** | (2010.01) |
| ***C12N 5/10*** | (2006.01) |
| ***C12N 15/00*** | (2006.01) |
| ***C12N 15/85*** | (2006.01) |

(52) U.S. Cl.

CPC ............ *A61L 27/3804* (2013.01); *A61K 9/70* (2013.01); *A61K 35/30* (2013.01); *A61K 35/545* (2013.01); *A61L 27/3839* (2013.01); *A61P 27/02* (2018.01); *C12N 5/0607* (2013.01); *C12N 5/062* (2013.01); *C12N 5/0621* (2013.01); *C12N 5/0696* (2013.01); *C12N 5/10* (2013.01); *C12N 15/85* (2013.01)

(58) Field of Classification Search

CPC ............ C12N 15/8509; C12N 2506/02; C12N 2310/14; C12N 2310/141; C12N 2501/60; C12N 2510/00; C12N 2517/02; C12N 15/85; C12N 2830/008; C12N 2830/85; C12N 5/0619; C12N 5/062; C12N 5/0662; C12N 5/0678; A01K 67/0275; A01K 67/0276; G01N 33/5073

See application file for complete search history.

(56) References Cited

U.S. PATENT DOCUMENTS

| | | | | |
|---|---|---|---|---|
| 7,390,659 | B2 * | 6/2008 | Jessell | A61P 21/00 435/377 |
| 7,745,113 | B2 * | 6/2010 | Evans | C12Q 1/6883 435/6.16 |
| 8,927,274 | B2 * | 1/2015 | Itskovitz-Eldor | C12N 5/0678 435/366 |
| 9,200,252 | B2 * | 12/2015 | Park | C12N 5/062 |
| 9,328,328 | B2 * | 5/2016 | Gamm | A61P 27/02 |
| 9,359,592 | B2 * | 6/2016 | Park | C12N 5/0621 |
| 9,683,215 | B2 * | 6/2017 | Melton | A61P 3/00 |
| 9,752,119 | B2 * | 9/2017 | Gamm | C12N 5/0621 |
| 9,770,471 | B2 * | 9/2017 | Eggan | A61K 35/30 |
| 10,221,393 | B2 * | 3/2019 | Melton | A61P 3/10 |
| 10,280,400 | B2 * | 5/2019 | Ohlemacher | C12N 5/0621 |
| 10,982,188 | B2 * | 4/2021 | Lako | G01N 33/5044 |

(Continued)

FOREIGN PATENT DOCUMENTS

| | | | | |
|---|---|---|---|---|
| JP | 2016-229355 | * 11/2016 | | C12N 5/10 |
| JP | 2017-138142 | * 7/2017 | | C12N 5/10 |

(Continued)

OTHER PUBLICATIONS

Martin-Partido et al.,Neural Regen. Res. 2015; 10:1951-1952. doi:10.4103/1673-5374.165301.*

(Continued)

*Primary Examiner* — Chang-Yu Wang

(74) *Attorney, Agent, or Firm* — Morgan, Lewis & Bockius LLP

(57) ABSTRACT

An object of the present invention is to provide a cell population suitable for transplant of retinal tissue and a method of production thereof. The present invention provides a cell population for transplant, comprising retinal cells with a modified bipolar cell-regulating gene and a method of production thereof.

19 Claims, 13 Drawing Sheets

Specification includes a Sequence Listing.

(56) References Cited

U.S. PATENT DOCUMENTS

| | | | | |
|---|---|---|---|---|
| 2009/0281163 | A1* | 11/2009 | Cepko | A61K 48/0058 514/44 A |
| 2011/0023143 | A1* | 1/2011 | Weinstein | A01K 67/0278 800/3 |
| 2011/0065645 | A1* | 3/2011 | Zou | C12N 5/0619 514/17.8 |
| 2011/0081719 | A1* | 4/2011 | Gamm | A61P 27/02 435/366 |
| 2011/0223140 | A1* | 9/2011 | Park | C12N 5/0621 435/325 |
| 2011/0223660 | A1* | 9/2011 | Park | C12N 5/062 435/375 |
| 2012/0082623 | A1* | 4/2012 | Kottmann | A61P 25/00 424/9.2 |
| 2012/0207744 | A1* | 8/2012 | Mendlein | C12N 15/111 424/130.1 |
| 2014/0341864 | A1 | 11/2014 | Nakano et al. | |
| 2016/0251616 | A1 | 9/2016 | Nakano et al. | |
| 2016/0251618 | A1* | 9/2016 | Gamm | A61P 27/02 435/368 |
| 2017/0002319 | A1* | 1/2017 | D'Alessio | G16B 25/10 |
| 2017/0211039 | A1* | 7/2017 | Ohlemacher | C12N 5/0621 |
| 2017/0218335 | A1* | 8/2017 | Lako | A61L 27/3604 |
| 2017/0313981 | A1 | 11/2017 | Kuwahara et al. | |
| 2019/0218510 | A1* | 7/2019 | Rao | C12Q 1/025 |
| 2021/0115397 | A1* | 4/2021 | Kume | C12N 5/0676 |

FOREIGN PATENT DOCUMENTS

| | | | |
|---|---|---|---|
| WO | 2011/055855 | A1 | 5/2011 |
| WO | 2013/077425 | A1 | 5/2013 |
| WO | 2015/025967 | A1 | 2/2015 |
| WO | 2015/077498 | A1 | 5/2015 |
| WO | 2016/063986 | A1 | 4/2016 |
| WO | WO2016/103269 | * | 6/2016 |

OTHER PUBLICATIONS

Human ISL-1 gene ID: 3670 factsheet from the NCBI website: www.ncbi.nlm.nih.gov/gene/?term=3670 retrieved on Jul. 11, 2021.*

Murine ISL-1 gene ID 16392 factsheet from the NCBI website: www.ncbi.nlm.nih.gov/gene/?term=16392 retrieved on Jul. 11, 2021.*

Human ISL-2 gene ID: 64843 factsheet from the NCBI website:www.ncbi.nlm.nih.gov/gene/?term=64843 retrieved on Jul. 11, 2021.*

Human BHLHE23 gene ID:128408 factsheet from the NCBI website:www.ncbi.nlm.nih.gov/gene/?term=128408 retrieved on Jul. 11, 2021.*

Song et al., Cell Res. Thera, 2013; 4:94. stemcellres.com/content/4/4/94.*

Bassett et al., Trends in Neurosci. 2012; 35:565-573.*

Collin et al., Stem Cell 2016; 34:311-321.*

Jones et al., Curr. Opin. Biotechnol. 2016; 40:133-138.*

Zhao et al., J. Biol. Chem. 2014, 289; 11945-11951.*

Pan et al., Development, 2008; 135; 1981-1990, doi:10.1242/dev.010751.*

Burgess et al. J of Cell Bio. 1990, 111:2129-2138.*

Bowie et al. Science, 1990, 247:1306-1310.*

Pawson et al. 2003, Science 300:445-452.*

Alaoui-Ismaili et al., Cytokine Growth Factor Rev. 2009; 20:501-507.*

Guo et al., PNAS 2004; 101:9205-9210.*

Murine BHLHE23 gene ID: 140489 factsheet from the NCBI website: www.ncbi.nlm.nih.gov/gene/?term=140489 retrieved on Jul. 11, 2021.*

Bramblett et al., Neuron, 2004; 43:779-793.*

Bejarano-Escobar et al., Exp. Eye Res. 2015, 138;22-31. dx.doi.org/10.1016/j.exer.2015.06.021.*

Gonzalez-Cordero et al., Nat. Biotechnol. 2013; 31:741-749.*

Singh et al. ARVO Annual Meeting Abstract Apr. 2014, IOVS, 55:3989, retrieved from the IOVS website: iovs.arvojournals.org/article.aspx?articleid=2269464.*

Osakada et al., Biotechnol. Genet. Eng. Rev. 2009; 26:271-334. Doi:10.5661/bger-26-297.*

Whitney et al., PNAS, 2011; 108:9697-9702.*

Martin-Partido et al.,Neural Regen. Res. 2015; 10: 1951-1952.*

Kamao et al., "Characterization of Human Induced Pluripotent Stem Cell-Derived Retinal Pigment Epithelium Cell Sheets Aiming for Clinical Application," Stem Cell Reports, 2: 205-218 (2014).

European Search Report issued in counterpart European Patent Application No. 17874713.5 dated May 7, 2020.

MacLaren et al., "Retinal repair by transplantation of photoreceptor precursors," Nature, 444: 203-207 (2006).

Eiraku et al., "Self-organizing optic-cup morphogenesis in three-dimensional culture," Nature, 472: 51-56 (2011).

Nakano et al., "Self-Formation of Optic Cups and Storable Stratified Neural Retina from Human ESCs," Cell Stem Cell, 10: 771-785 (2012).

Kuwahara et al., "Generation of ciliary margin-like stem cell niche from self-organizing human retinal tissue," Nature Communications, 6: 1-15 (2015).

Elshatory et al., "Islet-1 Controls the Differentiation of Retinal Bipolar and Cholinergic Amacrine Cells," Journal of Neuroscience, 27: 12707-12720 (2007).

Assawachananont et al., "Transplantation of Embryonic and Induced Pluripotent Stem Cell-Derived 3D Retinal Sheets Into Retinal Degenerative Mice," Stem Cell Reports, 2: 662-674 (2014).

Bramblett et al., "The Transcription Factor Bhlhb4 is Required for Rod Bipolar Cell Maturation," Neuron, 43: 779-793 (2004).

Iida et al., "Histone demethylase Jmjd3 is required for the development of subsets of retinal bipolar cells," PNAS, 111: 3751-3756 (2014).

Mandai et al., "Visual cell transplantation into mouse degenerative retina," Journal of Japanese Ophthalmological Society, 113: 198 (2009) (see partial English translation).

International Search Report issued in corresponding International Patent Application No. PCT/JP2017/042238 dated Feb. 13, 2018.

International Preliminary Report on Patentability and Written Opinion issued in corresponding International Patent Application No. PCT/JP2017/042238 dated May 28, 2019.

Santos-Ferreira et al., "Retinal transplantation of photoreceptors results in donor-host cytoplasmic exchange," Nature Communications, 7: 13028 (2016).

Office Action issued in counterpart European Patent Application No. 17874713.5 dated Sep. 7, 2021.

Wenbin and Xiang Ping, "Research progress of retinal stem cell related genes," JBengbu Med Coll, 37 (11) (2012).

"*Homo sapiens* ISL LIM homeobox 1 (ISL1), RefSeqGene on chromosome 5", NCBI Reference Sequence: NG_023040.1, Sep. 17, 2016. (2016).

Yamasaki et al., "A Genetic modification that reduces ON-bipolar cells in hESC-derived retinas enhances functional Integration after transplantation," iScience 25: 103657, Jan. 21, 2022.

Shirai et al., "Transplantation of human embryonic stem cell-derived retinal tissue in two primate models of retinal degeneration," PNAS, E81-E90 (2015).

Santos-Ferreira et al., "Daylight Vision Repair by Cell Transplantation," Stem Cells, 33: 79-90 (2015).

Perlman et al., "The Electroretinogram: ERG", U.S. National Library of Medicine, 1-43 (2001).

Third Party Observations in European Patent Application No. 17874713.5 dated Nov. 28, 2024.

* cited by examiner

Bhlhb4-/-

Green...graft nrl-GFP
Red...graft Ctbp2
White...Host bipolar cell PKCα

ISL1-/-

No.16 No.19

Day 65 Day 64

CRX::Venus CRX::Venus

HUMAN CELL POPULATION COMPRISING HUMAN RETINAL PROGENITOR CELLS WITHOUT AN ISL1 GENE FOR TRANSPLANTATION AND METHODS OF USE THEREOF

SEQUENCE LISTING SUBMISSION VIA EFS-WEB

A computer readable text file, entitled "SequenceListing.txt" created on or about Aug. 28, 2024 with a file size of about 89,483 bytes contains the sequence listing for this application and is hereby incorporated by reference in its entirety.

TECHNICAL FIELD

The present invention relates to a cell population for transplant and a method for producing the same.

BACKGROUND ART

It has recently been reported that transplantation of photoreceptor precursor cells at an appropriate differentiation stage into a normal retina in a living murine body results in the functional integration of the cells (Non Patent Literature 1), and the possibility of transplantation therapy for degenerative diseases of photoreceptor cells such as retinitis pigmentosa has been shown.

Many methods for inducing differentiation of pluripotent stem cells to three-dimensional self-organized retinal tissues have been reported and it is becoming possible to produce and transplant three-dimensional retinal tissue having stratified structure. For example, methods have been reported for obtaining multilayered retinal tissue from pluripotent stem cells (Non-Patent Literature 2 and Patent Literature 1); for obtaining multilayered retinal tissue by forming an aggregate of homogeneous pluripotent stem cells in a serum-free culture medium containing a Wnt signaling pathway inhibitor, and culturing the obtained aggregate in suspension in the presence of a basement membrane preparation and then in a serum culture medium (Non Patent Literature 3, Patent Literature 2); and for obtaining retinal tissue by culturing an aggregate of pluripotent stem cells in suspension in a culture medium containing a BMP signaling pathway agent (Non-Patent Literature 4 and Patent Literature 3), and the like. Furthermore, it has been reported that transplanting retinal tissue obtained by induction of differentiation of pluripotent stem cells into subject results in subsequent integration, differentiation, and maturation of the transplant, while it has also been reported that the functional integration of the transplant is not sufficient (Non Patent Literature 5).

Meanwhile, some genes involved in development or differentiation of retinal cells contained in retinal tissue in the living body have been reported.

For example, it has been reported that the ISL1 (Insulin gene enhancer protein 1, Islet-1) gene is expressed in the pancreas, the heart, the nerve, and the like and rod bipolar cells, cone bipolar cells, amacrine cells, and ganglion cells degenerated in the body of retina-specific ISL1 gene KO mice (Non Patent Literature 6).

Moreover, it has been reported that the BHLHE23 (basic helix-loop-helix family, member e23) gene is expressed in the pancreas, the brain, the retina, and the like and rod bipolar cells degenerated in the body of BHLHE23 gene KO mice (Non Patent Literature 7).

CITATION LIST

Patent Literature

Patent Literature 1:
International Publication No. WO 2011/055855
Patent Literature 2:
International Publication No. WO 2013/077425
Patent Literature 3:
International Publication No. WO 2015/025967

Non Patent Literature

Non Patent Literature 1:
Nature, 444, 203-207 (2006)
Non Patent Literature 2:
Nature, 472, 51-56 (2011)
Non Patent Literature 3:
Cell Stem Cell, 10 (6), 771-785 (2012)
Non Patent Literature 4:
Nature Communications, 6, 6286 (2015)
Non Patent Literature 5:
Stein Cell Reports, 2, 662-674 (2014)
Non Patent Literature 6:
J Neurosci, 27 (46), 12, 12707-20 (2007)
Non Patent Literature 7:
Neuron, 43 (6), 779-93 (2004)

SUMMARY OF INVENTION

Technical Problem

An object of the present invention is to provide a cell population for transplant suitable for transplant of retinal tissue and a method for producing the same.

Solution to Problem

The present inventors found that the functional integration after transplantation of retinal tissue is improved by reducing bipolar cells in the retinal tissue of the transplant. More specifically, the present inventors made multiple examinations to achieve the aforementioned object and found that retinal cells having a genome in which a bipolar cell-regulating gene, described later, is modified do not sufficiently differentiate and mature into bipolar cells, but do differentiate and mature into photoreceptor cells without problems, in comparison with retinal cells having the wild-type genome, and that the ratio of contact between photoreceptor cells derived from the transplant and bipolar cells from the host is increased by use of the cell population for transplant (retinal tissue or the like) comprising the aforementioned retinal cells for transplant and the functional integration after the transplant of the retinal tissue may be improved, thereby completing the present invention.

Accordingly, the present invention relates to:

[1] A cell population for transplant, comprising retinal cells having a modified bipolar cell-regulating gene.

[2] The cell population for transplant according to the aforementioned [1], wherein the cell population is in a form of cell suspension or cell aggregate.

[3] The cell population for transplant according to the aforementioned [1] or [2], wherein the bipolar cell-regulating gene is a gene encoding a transcriptional regulator.

[4] The cell population for transplant according to the aforementioned [3], wherein the bipolar cell-regulating gene is one or a plurality of genes selected from the group consisting of an ISL1 gene and a BHLHE23 gene.

[5] The cell population for transplant according to the aforementioned [4], wherein the ISL1 gene has a nucleotide sequence set forth in the following (1) or (2):

(1) a nucleotide sequence set forth in SEQ ID NO: 1, 4, or 7;

(2) a nucleotide sequence having a nucleotide sequence modified from the nucleotide sequence set forth in SEQ ID NO: 1, 4, or 7 by deletion, addition, insertion, or substitution of one or a plurality of nucleotides, and encoding a protein having 80% or more sequence identity with an amino acid sequence set forth in SEQ ID NO: 3, 6, or 9, wherein the nucleotide sequence encodes a protein satisfying at least one of:

(a) the protein has DNA binding ability, (b) the protein has a function to regulate genetic transcription, and (c) the protein can be recognized by an antibody that specifically recognizes a protein consisting of the amino acid sequence set forth in SEQ ID NO: 3, 6, or 9.

[6] The cell population for transplant according to the aforementioned [4] or [5], wherein the BHLHE23 gene has a nucleotide sequence set forth in the following (1) or (2):

(1) a nucleotide sequence set forth in SEQ ID NO: 10 or 13;

(2) a nucleotide sequence having a nucleotide sequence modified from the nucleotide sequence set forth in SEQ ID NO: 10 or 13 by deletion, addition, insertion or substitution of one or a plurality of nucleotides, and encoding a protein having 80% or more sequence identity with an amino acid sequence set forth in SEQ ID NO: 12 or 15, wherein the nucleotide sequence encodes a protein satisfying at least one of:

(a) the protein has DNA binding ability, (b) the protein has a function to regulate genetic transcription, and (c) the protein can be recognized by an antibody that specifically recognizes a protein consisting of the amino acid sequence set forth in SEQ ID NO: 12 or 15.

[7] The cell population for transplant according to any one of the aforementioned [1] to [6], wherein the modification of a bipolar cell-regulating gene comprises deletion of the gene.

[8] The cell population for transplant according to any one of the aforementioned [1] to [7], wherein the retinal cells are derived from a pluripotent stem cell.

[9] The cell population for transplant according to the aforementioned [8], wherein the pluripotent stem cell is an induced pluripotent stem cell or an embryonic stem cell.

[10] The cell population for transplant according to any one of the aforementioned [1] to [9], wherein the retinal cells comprise one or a plurality of cells selected from the group consisting of a retinal progenitor cell, a photoreceptor precursor cell, and a photoreceptor cell.

[11] The cell population for transplant according to the aforementioned [10], wherein the retinal cells comprise one or a plurality of cells selected from a Chx10-positive cell, a Crx-positive cell, and a Recoverin-positive cell.

[12] The cell population for transplant according to the aforementioned [10] or [11], wherein the sum of the number of retinal progenitor cells, photoreceptor precursor cells, and photoreceptor cells is 10% or more of the total number of cells in the cell population for transplant.

[13] The cell population for transplant according to any one of the aforementioned [10] to [12], wherein the functional integration rate of the photoreceptor cells or photoreceptor cells induced from the retinal progenitor cell or photoreceptor precursor cell after the transplant is improved.

[14]A culture of a cell population for transplant, comprising:

(1) a cell population for transplant according to any one of the aforementioned [1] to [13]; and (2) a medium necessary to maintain viability of the cell population for transplant.

[15] A method for producing a cell population for transplant comprising retinal cells, comprising the following steps (1) and (2):

(1) modifying a bipolar cell-regulating gene of pluripotent stem cells to obtain in vitro, a cell population comprising the pluripotent stem cells with the modified bipolar cell-regulating gene;

(2) inducing differentiation of the cell population comprising the pluripotent stem cells obtained in step (1) into retinal cells in vitro to obtain a cell population for transplant comprising the retinal cells.

[16] The method of production according to the aforementioned [15], wherein the cell population for transplant comprising the retinal cells is in a form of cell suspension or cell aggregate.

[17] The method of production according to the aforementioned [15] or [16], wherein the bipolar cell-regulating gene is a gene encoding a transcriptional regulator.

[18] The method of production according to the aforementioned [17], wherein the bipolar cell-regulating gene is one or a plurality of genes selected from the group consisting of an ISL1 gene and a BHLHE23 gene.

[19] The method of production according to the aforementioned [18], wherein the ISL1 gene has a nucleotide sequence set forth in the following (1) or (2):

(1) a nucleotide sequence set forth in SEQ ID NO: 1, 4, or 7;

(2) a nucleotide sequence having a nucleotide sequence modified from the nucleotide sequence set forth in SEQ ID NO: 1, 4, or 7 by deletion, addition, insertion, or substitution of one or a plurality of nucleotides, and encoding a protein having 80% or more sequence identity with an amino acid sequence set forth in SEQ ID NO: 3, 6, or 9, wherein the nucleotide sequence encodes a protein satisfying at least one of:

(a) the protein has DNA binding ability, (b) the protein has a function to regulate genetic transcription, and (c) the protein can be recognized by an antibody that specifically recognizes a protein consisting of the amino acid sequence set forth in SEQ ID NO: 3, 6, or 9.

[20] The method of production according to the aforementioned [18] or [19], wherein the BIILIIE23 gene has a nucleotide sequence set forth in the following (1) or (2):

(1) a nucleotide sequence set forth in SEQ ID NO: 10 or 13;

(2) a nucleotide sequence having a nucleotide sequence modified from the nucleotide sequence set forth in SEQ ID NO: 10 or 13 by deletion, addition, insertion or substitution of one or a plurality of nucleotides, and encoding a protein having 80% or more sequence identity with an amino acid sequence set forth in SEQ ID NO: 12 or 15, wherein the nucleotide sequence encodes a protein satisfying at least one of:

(a) the protein has DNA binding ability, (b) the protein has a function to regulate genetic transcription, and (c) the protein can be recognized by an antibody that specifically recognizes a protein consisting of the amino acid sequence set forth in SEQ ID NO: 12 or 15.

[21] The method of production according to any of the aforementioned [15] to [20], wherein the modification of a bipolar cell-regulating gene comprises deletion of the gene.

[22] The method of production according to any one of the aforementioned [15] to [21], wherein the pluripotent stem cells are induced pluripotent stem cells or embryonic stem cells.

[23] The method of production according to any one of the aforementioned [15] to [22], wherein the retinal cells comprise one or a plurality of cells selected from the group consisting of a retinal progenitor cell, a photoreceptor precursor cell and a photoreceptor cell.

[24] The method of production according to the aforementioned [23], wherein the retinal cells comprise one or a plurality of cells selected from a Chx10-positive cell, a Crx-positive cell, and a Recoverin-positive cell.

[25] The method of production according to the aforementioned [23] or [24], wherein the sum of the number of retinal progenitor cells, photoreceptor precursor cells, and photoreceptor cells is 10% or more of the total number of cells in the cell population for transplant comprising the retinal cells.

[26] The method of production according to any one of the aforementioned [23] to [25], wherein the functional integration rate after the transplant of the photoreceptor cells or photoreceptor cells induced from the retinal progenitor cell or photoreceptor precursor cell after the transplant is improved.

[27] A method for treating a disease based on a disorder of retinal tissue or a condition of retinal tissue damage, comprising transplanting an effective amount of the cell population for transplant according to any one of the aforementioned [1] to [13] into a subject in need of transplant.

[28] A pharmaceutical composition for treating a disease based on a disorder of retinal tissue or a condition of retinal tissue damage, comprising the cell population for transplant according to any one of the aforementioned [1] to [13] as an active ingredient.

[29] The pharmaceutical composition according to the aforementioned [28], wherein the pharmaceutical composition is in a form of cell sheet.

[30] A therapeutic agent for a disease based on a disorder of retinal tissue or a condition of retinal tissue damage, comprising the cell population for transplant according to any one of the aforementioned [1] to [13].

[31] The therapeutic agent according to the aforementioned [30], wherein the therapeutic agent is in a form of cell sheet.

Advantageous Effects of Invention

According to the present invention, it becomes possible to provide a cell population for transplant suitable for transplant of retinal tissue and a method for producing the same.

DESCRIPTION OF EMBODIMENTS

Figure 1:
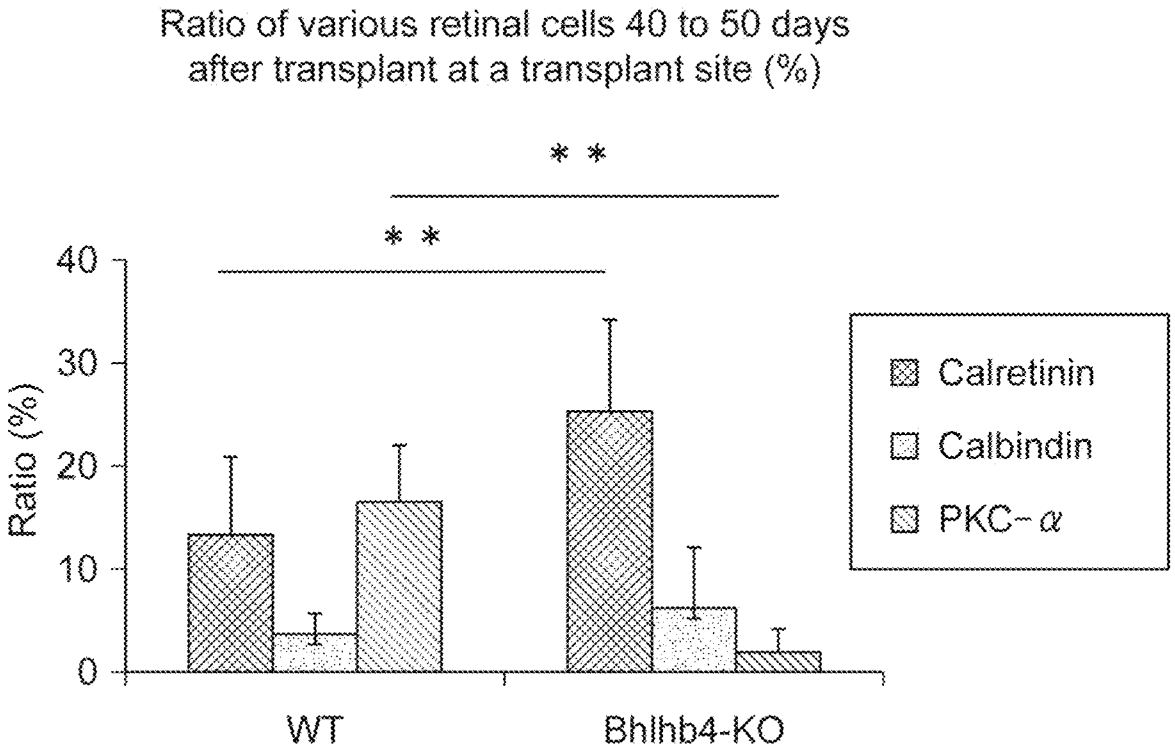
FIG. 1 is a graph showing the ratio of rod bipolar cells, amacrine cells, and horizontal cells at a transplant site 40 to 50 days after transplant of the retinal tissue derived from mouse iPS cells wherein the function of a Bhlhb4 gene is deleted.

1. Regarding Cell Population for Transplant comprising Retinal Cells

One embodiment of the present invention provides a cell population for transplant, comprising retinal cells with a modified bipolar cell-regulating gene. Retinal cells with a modified a bipolar cell-regulating gene do not sufficiently differentiate and mature into bipolar cells, but do differentiate and mature into photoreceptor cells without problems, in comparison with retinal cells having the wildtype genome. Therefore, the ratio of contact between photoreceptor cells derived from the transplant and bipolar cells from the host is increased by use of the cell population for transplant comprising the aforementioned retinal cells for transplant, and the functional integration after the transplant of the retinal tissue may be improved. A detailed description will be provided below.

1-1. Cell Population for Transplant

The "cell population for transplant" in the present invention means a cell population prepared for transplant and used for transplant.

The "cell population" in the present invention means a population in which 2 or more of the same kind or different kinds of cells are present. Preferably, the cell population is present in a medium such as a culture medium. Cell populations include cell suspensions and cell aggregates and it is preferred that the cell population is in a form of cell suspension or cell aggregate.

The "cell suspension" in the present invention means a medium containing the same kind or different kinds of a plurality of cells in suspension. The suspension preferably refers to a state in which a majority (for example, 50% or more, 60% or more, 70% or more, 80% or more, 90% or more, or 95% or more) of cells present in a medium are dissociated from each other and exists without sustained physical contact with each other. Some (for example, 50% or less, 40% or less, 30% or less, 20% or less, 10% or less or 5% or less) cells among the cells present in the medium may exist as cell aggregates or the like.

The "cell aggregate" in the present invention is not particularly limited, as long as it is a plurality of cells adhering to each other to foam a mass and the term refers to, for example, a mass formed from cells dispersed in a medium such as a culture medium. Cell aggregates include tissues and cell sheets.

The "cell sheet" in the present invention refers to a monolayer or stratified structure composed of one cell or a plurality of cells in which a biological adhesion(s) are formed in at least two-dimensional direction(s). The cell sheet may readily be prepared from adherently cultured cells or a cell aggregate(s) by excision with tweezers, a knife, scissors, or the like.

The "tissue" in the present invention means a structure of cell population having structure in which one kind of cells homogenous in morphology or nature or a plurality of kinds of cells heterogenous in morphology or nature are three-dimensionally arranged in a certain pattern. Examples of the tissue include retinal tissue.

The "retinal tissue" (or "retinal organoid") in the present invention means a tissue in which one kind or a plurality of kinds of retinal cells constituting one or a plurality of retinal layers in the retina in vivo are three-dimensionally arranged in one or a plurality of layers. Which retinal layer each kind of cells constitutes may be determined by a known method, for example, the presence or absence of expression or the expression level of a cell marker.

The "retinal layer(s)" in the present invention means a layer(s) constituting the retina, and specific examples thereof include the retinal pigment epithelial layer, the photoreceptor cell layer, the outer limiting membrane, the outer nuclear layer, the outer plexiform layer, the inner nuclear layer, the inner plexiform layer, the ganglion cell layer, the nerve fiber layer, and the inner limiting membrane.

The "photoreceptor cell layer" in the present invention is one of the retinal layers and means the retinal layer comprising many (for example, 70%, preferably 80%, more preferably 90% or more in terms of the number of nuclei of photoreceptor cells present in the photoreceptor cell layer) photoreceptor cells (rod photoreceptor cells, cone photoreceptor cells).

1-2. Retinal Cells

The term "retinal cells" in the present invention means cells constituting a retinal layer(s) in the retina in vivo or progenitor/precursor cells thereof. Specific examples thereof include, but are not limited to, photoreceptor cells (rod photoreceptor cells, cone photoreceptor cells), horizontal cells, amacrine cells, interneurons, retinal ganglion cells (ganglion cells), bipolar cells (rod bipolar cells, cone bipolar cells), Muller glial cells, retinal pigment epithelial (RPE) cells, ciliary marginal zone cells, progenitor/precursor cells thereof (for example, photoreceptor precursor cells, bipolar cell precursor cells), and retinal progenitor cells.

The term "mature retinal cells" means differentiated cells such as photoreceptor cells (rod photoreceptor cells, cone photoreceptor cells), horizontal cells, amacrine cells, interneurons, retinal ganglion cells (ganglion cells), bipolar cells (rod bipolar cells, cone bipolar cells), Muller glial cells, retinal pigment epithelial (RPE) cells, and ciliary marginal zone cells. The term "immature retinal cells" means progenitor/precursor cells (for example, photoreceptor precursor cells, bipolar cell precursor cells, retinal progenitor cells) determined to differentiate into mature retinal cells.

The photoreceptor precursor cells, horizontal cell precursor cells, bipolar cell precursor cells, amacrine cell precursor cells, retinal ganglion cell precursor cells, Muller glial precursor cells, and retinal pigment epithelial precursor cells refer to precursor cells determined to differentiate into photoreceptor cells, horizontal cells, bipolar cells, amacrine cells, retinal ganglion cells, Muller glial cells, and retinal pigment epithelial cells, respectively.

The term "retinal progenitor cells" in the present invention refers to progenitor cells that can differentiate into any of the immature retinal cells such as photoreceptor precursor cells, horizontal cell precursor cells, bipolar cell precursor cells, amacrine cell precursor cells, retinal ganglion cell precursor cells, Muller glial precursor cells, and retinal pigment epithelial precursor cells and that can finally differentiate into any of mature retinal cells such as photoreceptor cells (rod photoreceptor cells, cone photoreceptor cells), horizontal cells, bipolar cells, amacrine cells, retinal ganglion cells, Muller glial cells, and retinal pigment epithelial cells.

The presence of retinal cells may be determined by the presence or absence of expression of a marker of retinal cells (hereinafter, referred to as a "retinal cell marker"). The presence or absence of expression of a retinal cell marker or the proportion of retinal cell marker-positive cells in a cell population or a tissue may be easily determined by a person skilled in the art, for example, by counting the number of particular retinal cell marker-positive cells by a technique such as flow cytometry, immunostaining and so on using a commercially available antibody, and dividing the number by the total number of cells.

Examples of the retinal cell marker include proteins such as Rx (also referred to as "Rax"), PAX6, and Chx10 expressed in retinal progenitor cells, Crx and Blimp1 expressed in photoreceptor precursor cells, Chx10, PKC$\alpha$, and L7 expressed in bipolar cells, TuJ1 and Brn3 expressed in retinal ganglion cells, calretinin expressed in amacrine cells, calbindin expressed in horizontal cells, Recoverin expressed in mature photoreceptor cells. (rod photoreceptor cells and cone photoreceptor cells), Nr1 and rhodopsin expressed in rod photoreceptor cells, Rxr-gamma, S-Opsin, and M/L-Opsin expressed in cone photoreceptor cells, GS and GFAP expressed in Muller glial cells, RPE65 and Mitf expressed in retinal pigment epithelial cells, and Rdh10 and SSEA1 expressed in ciliary marginal zone cells.

The term "positive cells" means cells expressing a particular marker on the cell surface or in the cell. For example, the term "Chx10-positive cells" means cells expressing the Chx10 protein in the nucleus.

1-3. Bipolar Cell-Regulating Gene

The "bipolar cell-regulating gene" in the present invention refers to a gene expressed in retinal progenitor cells, bipolar cell precursor cells, and/or bipolar cells and involved in the differentiation, maturation, survival, proliferation, metabolism, or the function of forming the synapse with photoreceptor cells of bipolar cells, but not in the differentiation, maturation, survival, proliferation, metabolism, and function of photoreceptor cells. Therefore, by modifying the bipolar cell-regulating gene, retinal progenitor cells and the like that cause defect of differentiation, degeneration, dysfunction, and/or the like of bipolar cells, but allow photoreceptor cells to maintain the normal function may be prepared. Preferably, the bipolar cell-regulating gene is a gene that is expressed in bipolar cell precursor cells, and/or bipolar cells, but not expressed in retinal progenitor cells, photoreceptor precursor cells, or photoreceptor cells.

In one embodiment, the bipolar cell-regulating gene refers to a gene that is expressed in bipolar cell precursor cells and/or bipolar cells and involved in the maturation of bipolar cells, but not in the differentiation, maturation, survival, proliferation, metabolism, and function of photoreceptor cells. Preferably, the bipolar cell-regulating gene is a gene that is expressed in bipolar cell precursor cells and/or bipolar cells, but not expressed in retinal progenitor cells, photoreceptor precursor cells, and photoreceptor cells. The "maturation of bipolar cells" means that bipolar cell precursor cells differentiate into bipolar cells and become capable of forming the synapse with photoreceptor cells. The maturation of bipolar cells may be confirmed by detecting the expression of the Chx10 protein, the PKCα protein, L7, or the like, which are markers of bipolar cells by a technique such as immunohistochemical analysis, flow cytometry, or the like.

In one embodiment, the bipolar cell-regulating gene includes a gene encoding a transcription factor involved in the aforementioned function (the differentiation, maturation, survival, proliferation, metabolism, or function of forming the synapse with photoreceptor cells of bipolar cells), specifically a transcription factor that maintains or enhances the function. The bipolar cell-regulating gene is preferably a gene encoding a transcription factor.

The transcription factor contains a region (domain) having a function involved in the regulation of transcription. For example, the transcription factor contains a characteristic DNA binding region (homeodomain, zinc finger domain, basic leucine zipper domain, basic-helix-loop-helix domain, or the like). In one embodiment, the transcription factor further contains a transcription cofactor binding domain. Therefore, those skilled in the art can determine whether a particular gene is a gene encoding a transcription factor or not, for example, based on whether the gene contains a characteristic DNA-binding region or not.

The gene that is expressed in retinal progenitor cells, bipolar cell precursor cells, and/or bipolar cells can be identified by a person skilled in the art by a well known method. In one embodiment, the gene that is expressed in bipolar cells or retinal progenitor cells in the fetal stage or the adult stage may be detected by gene expression analysis (for example, microarray analysis) and/or histological analysis (for example, immunostaining analysis, in situ hybridization).

Those skilled in the art can identify the gene involved in the differentiation, maturation, survival, proliferation, metabolism, or the function of forming synapse with photoreceptor cells of bipolar cells, but not in the differentiation, maturation, survival, proliferation, metabolism and function of photoreceptor cells by a well known method or known information. In one embodiment, the effect of the aforementioned gene on the differentiation, maturation, survival, proliferation, metabolism or function of forming the synapse with photoreceptor cells of bipolar cells and the differentiation, maturation, survival, proliferation, metabolism, and function of photoreceptor cells may be examined in a genetically modified cell line and/or a genetically modified animals produced by a transfection technique (for example, electroporation, lipofection).

In a specific embodiment, genes expressed in retinal progenitor cells, bipolar cell precursor cells, or bipolar cells may be screened by gene expression analysis (for example, microarray analysis), and genes involved in the aforementioned function may be selected as candidate genes for the bipolar cell-regulating gene by known information (homology of the genetic sequence to the ISL1 gene or the like, function, conserved functional domain). In a preferred embodiment, genes that are expressed in bipolar cell precursor cells or bipolar cells, but not in photoreceptor precursor cells or photoreceptor cells are selected as candidate genes for the bipolar cell-regulating gene. Moreover, in another preferred embodiment, genes encoding transcription factors are selected as candidate genes for the bipolar cell-regulating gene. The genes encoding transcription factors may be selected based on the aforementioned conserved domains or the like. These methods for selecting candidate genes for the bipolar cell-regulating gene may be used in combination. For example, genes that are expressed in bipolar cells precursor cells or bipolar cells, but not in photoreceptor precursor cells or photoreceptor cells and that encode transcription factors may be selected as candidate genes for the bipolar cell-regulating gene.

Furthermore, a gene may be examined whether it is a bipolar cell-regulating gene, for example, by producing retinal tissue from pluripotent stem cells in which a selected gene is modified and performing histological analysis.

Examples of the bipolar cell-regulating gene include, but are not limited to, genes encoding transcription factors expressed in bipolar cells, such as the ISL1 gene and the BHLHE23 gene, which are involved in the maturation of bipolar cells and genes having nucleotide sequences that are substantially the same as these genes.

The term "genes having nucleotide sequences that are substantially the same" in the present invention means genes that encode proteins having the function that is substantially the same in nature as that of a protein encoded by a gene having a nucleotide sequence set forth in a particular sequence ID number and that have about 80% or more (preferably about 85% or more, about 90% or more, or about 95% or more) sequence identity with the nucleotide sequence set forth in a particular sequence ID number or have nucleotide sequences encoding proteins having about 80% or more (preferably about 85% or more, about 90% or more, or about 95% or more) sequence identity with an amino acid sequence set forth in a particular sequence ID number. The term "genes having nucleotide sequences that are substantially the same" encompasses genes that are an ortholog, a subtype, an isoform, or a mutant and known to have the function that is substantially the same in nature, even if the genes do not satisfy the above definition (for example, sequence identity lower than 80%).

In the present invention, the "function that is substantially the same in nature" means that the nature of the function is qualitatively the same, for example, in a physiological or pharmacological view and quantitative factors such as the degree of the function and the molecular weight of the protein may be different.

The "sequence identity" of a nucleotide sequence or an amino acid sequence in the present invention means proportion (%) of identical nucleotides or amino acids to the total nucleotide sequence or amino acid sequence overlapped in the optimal alignment when 2 nucleotide sequences are aligned using a mathematical algorithm known in the art (preferably, the algorithm is such an algorithm with which the optimal alignment is obtained in consideration of introduction of a gap(s) in one or both sequences.). Those skilled in the art can easily determine the "sequence identity" of a nucleotide sequence or an amino acid sequence. For example, NCBI BLAST (National Center for Biotechnology Information Basic Local Alignment Search Tool) may be used.

The "ortholog" in the present invention means a gene or a protein derived from different animal species having high similarity derived from the same ancestor in the evolutionary tree.

The "subtype" in the present invention means a protein group having high genetic homology and similar function.

The "isoform" in the present invention means a gene or a protein having the function that is substantially the same in nature while the conformation of the protein is different. A plurality of isoforms may be splicing variants derived from the same DNA or they may be derived from different DNAs.

The "mutant" in the present invention refers to a gene that encodes a protein having the function that is substantially the same in nature as that of a protein encoded by a gene having a nucleotide sequence set forth in a particular sequence ID number and that has a nucleotide sequence modified by deletion, addition, insertion or substitution of one or a plurality of nucleotides.

Those skilled in the art can determine whether genes are the "genes having nucleotide sequences that are substantially the same" as a particular gene, for example, based on nucleotide sequences of genes listed in ncbi.nlm.nih.gov.

As used herein, the "gene" means a nucleotide sequence of a region encoding a particular protein (a region that contains from an initiation codon to a termination codon and may contain an intron(s)) and its flanking regions (regions such as a promoter, an enhancer, a silencer, and a terminator) present on a chromosome. The ranges of the flanking regions vary depending on the gene, and examples thereof include 50 bp, 100 bp, 200 bp, 300 bp, 400 bp, 500 bp, 1000 bp, and 2000 bp. Accordingly, the modification of a gene includes not only the modification of the region encoding a particular protein, but also the modification of its flanking regions.

The ISL1 gene and the BHLHE23 gene will be described below.

The ISL1 (Insulin gene enhancer protein 1, ISL LIM homeobox 1, Islet-1) gene is a known gene. Examples of the ISL1 gene include genes having the nucleotide sequence set forth in SEQ ID NO: 1 (GenBank Accession Gene ID: 3670 (NC_000005.10)) or nucleotide sequences that are substantially the same as this nucleotide sequence. Moreover, the ISL1 gene also encompasses genes containing, as exon, nucleotide sequences containing an exon part contained in the nucleotide sequence set forth in SEQ ID NO: 1 (for example, the nucleotide sequence set forth in SEQ ID NO: 2 (GenBank Accession Gene ID: NM_002202.2)) or nucleotide sequences that are substantially the same as this exon part. The ISL1 protein encoded by a nucleotide sequence corresponding to the positions 549 to 1598 in the nucleotide sequence set forth in SEQ ID NO: 2 has the amino acid sequence set forth in SEQ ID NO: 3 (GenBank Accession Gene ID: NP_002193.2). The ISL1 gene also encompasses genes containing, as exon, nucleotide sequences encoding the amino acid sequence set forth in SEQ ID NO: 3 or amino acid sequences that are substantially the same as this.

A known ortholog of the human ISL1 gene is the murine ISL1 gene having the nucleotide sequence set forth in SEQ ID NO: 4 (GenBank Accession Gene ID: 16392 (NC_000079.6)). The ISL1 gene also encompasses genes having the nucleotide sequence set forth in SEQ ID NO: 4 or nucleotide sequences that are substantially the same as this. Moreover, the ISL1 gene also encompasses genes containing, as exon, nucleotide sequences containing an exon part contained in the nucleotide sequence set forth in SEQ ID NO: 4 (for example, the nucleotide sequence set forth in SEQ ID NO: 5 (GenBank Accession Gene ID: NM_021459.4)) or nucleotide sequences that are substantially the same as this. The ISL1 protein encoded by a nucleotide sequence corresponding to the positions 267 to 1316 in the nucleotide sequence set forth in SEQ ID NO: 5 has the amino acid sequence set forth in SEQ ID NO: 6 (GenBank Accession Gene ID: NP_067434.3). The ISL1 gene also encompasses genes containing, as exon, nucleotide sequences encoding the amino acid sequence set forth in SEQ ID NO: 6 or amino acid sequences that are substantially the same as this.

A known human subtype of the human ISL1 gene is the human ISL2 gene having the nucleotide sequence set forth in SEQ ID NO: 7 (GenBank Accession Gene ID: 64843 (NC_000015.10)). The ISL1 gene also encompasses genes having the nucleotide sequence set forth in SEQ ID NO: 7 or nucleotide sequences that are substantially the same as this. Moreover, the ISL1 gene also encompasses genes containing, as exon, nucleotide sequences containing an exon part contained in the nucleotide sequence set forth in SEQ ID NO: 7 (for example, the nucleotide sequence set forth in SEQ ID NO: 8 (GenBank Accession Gene ID: NM_145805)) or nucleotide sequences that are substantially the same as this. The ISL1 protein encoded by a nucleotide sequence corresponding to the positions 161 to 1240 in the nucleotide sequence set forth in SEQ ID NO: 8 has the amino acid sequence set forth in SEQ ID NO: 9 (GenBank Accession Gene ID: NP_665804.1). The ISL1 gene also encompasses genes containing, as exon, nucleotide sequences encoding the amino acid sequence set forth in SEQ ID NO: 9 or amino acid sequences that are substantially the same as this.

The term "genes having nucleotide sequences that are substantially the same as SEQ ID NO: 1" means genes that encode proteins having the function that is substantially the same in nature as that of a protein having the amino acid sequence set forth in SEQ ID No: 3 wherein the genes have about 80% or more (preferably about 85% or more, about 90% or more, or about 95% or more) sequence identity with a nucleotide sequence set forth in SEQ ID NO: 1 or wherein the exon of the genes have such sequence identity with the nucleotide sequence set forth in SEQ ID NO: 2, or genes that contain a nucleotide sequence encoding a protein having about 80% or more (preferably about 85% or more, about 90% or more, or about 95% or more) sequence identity with the amino acid sequence set forth in SEQ ID NO: 3.

The term "genes having nucleotide sequences that are substantially the same as SEQ ID NO: 4" means genes that encode proteins having the function that is substantially the same in nature as that of a protein having the amino acid sequence set forth in SEQ ID No: 6 wherein the genes that have about 80% or more (preferably about 85% or more, about 90% or more, or about 95% or more) sequence identity with a nucleotide sequence set forth in SEQ ID NO: 4 or wherein the exon of the genes have such sequence identity with the nucleotide sequence set forth in SEQ ID NO: 5, or genes that contain a nucleotide sequence encoding a protein having about 80% or more (preferably about 85% or more, about 90% or more, or about 95% or more) sequence identity with the amino acid sequence set forth in SEQ ID NO: 6.

The term "genes having nucleotide sequences that are substantially the same as SEQ ID NO: 7" means genes that encode proteins having the function that is substantially the same in nature as that of a protein having the amino acid sequence set forth in SEQ ID No: 9 wherein the genes have about 80% or more (preferably about 85% or more, about 90% or more, or about 95% or more) sequence identity with a nucleotide sequence set forth in SEQ ID NO: 7 or wherein the exon of the genes have such sequence identity with the nucleotide sequence set forth in SEQ ID NO: 8, or genes that contain a nucleotide sequence encoding a protein having about 80% or more (preferably about 85% or more, about 90% or more, or about 95% or more) sequence identity with the amino acid sequence set forth in SEQ ID NO: 9.

It has been reported that the ISL1 protein is a homeodomain transcription factor, has two LIM domains, LIM1 and LIM2, an Lhx3 binding domain, and a DNA binding domain, and is involved in the maturation of bipolar cells.

Therefore, "having the function that is substantially the same in nature as that of a protein having the amino acid sequence set forth in SEQ ID No: 3" means having an ability to bind with DNA and the function of positively or negatively regulating transcription of a gene.

Specific examples of the "gene having a nucleotide sequence that is substantially the same as the nucleotide sequence set forth in SEQ ID NO: 1, 4, or 7", that is, the ISL1 gene include the following (1) or (2):

(1) a nucleotide sequence set forth in SEQ ID NO: 1, 4, or 7;

(2) a nucleotide sequence modified from the nucleotide sequence set forth in SEQ ID NO: 1, 4, or 7 by deletion, addition, insertion, or substitution of one or a plurality of nucleotides, and encoding a protein having 80% or more sequence identity with the amino acid sequence set forth in SEQ ID NO: 3, 6, or 9, wherein the nucleotide sequence encodes a protein satisfying at least one of:

(a) the protein has DNA binding ability, (b) the protein has a function to regulate genetic transcription, and (c) the protein can be recognized by an antibody that specifically recognizes a protein consisting of the amino acid sequence set forth in SEQ ID NO: 3, 6, or 9.

Here, examples of the "nucleotide sequence modified by deletion, addition, insertion or substitution of one or a plurality of nucleotides" include nucleotide sequences that have, after the deletion, addition, insertion or substitution, 80% or more, 85% or more, 90% or more, 95% or more, 97% or more, 98% or more, or 99% or more sequence identity with the nucleotide sequence before the deletion, addition, insertion, or substitution. Examples of the specific number of nucleotides in the "one or a plurality of nucleotides" are 1 to 100, 1 to 50, 1 to 30, 1 to 10, and 1 to several (2, 3, 4, or 5). The deletion, addition, insertion, or substitution may be a combination thereof.

In one embodiment of the present invention, the ISL1 gene is a gene at a chromosomal position (locus) "5q11.1" or "15q24.3" when it is a human gene or at a chromosomal position "13D2.3" when it is a murine gene. Those skilled in the art can determine the chromosomal position of the ISL1 gene (ortholog) in other animal species based, for example, on nucleotide sequences of genes listed in ncbi.nlm.nih.gov.

The ISL1 gene is preferably the human ISL1 gene or the murine ISL1 gene.

The BHLHE23 (basic helix-loop-helix family, member e23) gene is a known gene. Examples of the BHLHE23 gene include genes having the nucleotide sequence set forth in SEQ ID NO: 10 (GenBank Accession Gene ID: 128408 (NC_000020.11)) or nucleotide sequences that are substantially the same as the nucleotide sequence. Moreover, the BHLHE23 gene also encompasses genes containing, as exon, nucleotide sequences containing an exon part contained in the nucleotide sequence set forth in SEQ ID NO: 10 (for example, the nucleotide sequence set forth in SEQ ID NO: 11 (GenBank Accession Gene ID: NM_080606)) or nucleotide sequences that are substantially the same as this. The BHLHE23 protein encoded by the nucleotide positions 262 to 987 in the nucleotide sequence set forth in SEQ ID NO: 11 is a protein having the amino acid sequence set forth in SEQ ID NO: 12 (GenBank Accession Gene ID: NP_542173.2). The BHLHE23 gene also encompasses genes containing, as exon, nucleotide sequences encoding the amino acid sequence set forth in SEQ ID NO: 12 or amino acid sequences that are substantially the same as this.

Known ortholog of the human BHLHE23 gene is the murine BHLHE23 gene (Bhlhb4 gene) having the nucleotide sequence set forth in SEQ ID NO: 13 (GenBank Accession Gene ID: 140489 (NC_000068.7)). The BHLHE23 gene encompasses genes having the nucleotide sequence set forth in SEQ ID NO: 13 or nucleotide sequences that are substantially the same as this. Moreover, the BHLHE23 gene also encompasses genes containing, as exon, nucleotide sequences containing an exon part contained in the nucleotide sequence set forth in SEQ ID NO: 13 (for example, the nucleotide sequence set forth in SEQ ID NO: 14 (GenBank Accession Gene ID: NM_080641.5)) or nucleotide sequences that are substantially the same as this. The murine Bhlhb4 protein encoded by the nucleotide positions 158 to 829 in the nucleotide sequence set forth in SEQ ID NO: 14 has an amino acid sequence set forth in SEQ ID NO: 15 (GenBank Accession Gene ID: NP_542372.2). The BHLHE23 gene also encompasses genes containing, as exon, nucleotide sequences encoding the amino acid sequence set forth in SEQ ID NO: 15 or amino acid sequences that are substantially the same as this.

The term "genes having nucleotide sequences that are substantially the same as SEQ ID NO: 10" means genes that encode proteins having the function that is substantially the same in nature as that of a protein having the amino acid sequence set forth in SEQ ID No: 12 wherein the genes have about 80% or more (preferably about 85% or more, about 90% or more, or about 95% or more) sequence identity with a nucleotide sequence set forth in SEQ ID NO: 10 or wherein the exon of the genes have such sequence identity with the nucleotide sequence set forth in SEQ ID NO: 11, or genes that contain a nucleotide sequence encoding a protein having about 80% or more (preferably about 85% or more, about 90% or more, or about 95% or more) sequence identity with the amino acid sequence set forth in SEQ ID NO: 12.

The term "genes having nucleotide sequences that are substantially the same as SEQ ID NO: 13" means genes that encode proteins having the function that is substantially the same in nature as that of a protein having the amino acid sequence set forth in SEQ ID No: 15 wherein the genes have about 80% or more (preferably about 85% or more, about 90% or more, or about 95% or more) sequence identity with the nucleotide sequence set forth in SEQ ID NO: 13 or wherein the exon of the genes have such sequence identity with the nucleotide sequence set forth in SEQ ID NO: 14, or genes that contain a nucleotide sequence encoding a protein having about 80% or more (preferably about 85% or more, about 90% or more, or about 95% or more) sequence identity with the amino acid sequence set forth in SEQ ID NO: 15.

It has been reported that the BHLHE23 protein is a Basic helix-loop-helix transcription factor, has a DNA binding domain and the helix-loop-helix domain, and is involved in the maturation of bipolar cells.

Therefore, "having the function that is substantially the same in nature with a protein having the amino acid sequence set forth in SEQ ID NO: 12" means having an ability to bind with DNA and the function of positively or negatively regulating transcription of a gene.

Specific examples of the "gene having a nucleotide sequence that is substantially the same as the nucleotide sequence set forth in SEQ ID NO: 10 or 13", that is, the BHLHE23 gene include the following (1) or (2):

(1) a nucleotide sequence set forth in SEQ ID NO: 10 or 13;
(2) a nucleotide sequence modified from the nucleotide sequence set forth in SEQ ID NO: 10 or 13 by deletion, addition, insertion or substitution of one or a plurality of nucleotides, and encoding a protein having 80% or more sequence identity with an amino acid sequence set forth in SEQ ID NO: 12 or 15, wherein the nucleotide sequence encodes a protein satisfying at least one of:
(a) the protein has DNA binding ability,
(b) the protein has a function to regulate genetic transcription, and
(c) the protein can be recognized by an antibody that specifically recognizes a protein consisting of the amino acid sequence set forth in SEQ ID NO: 12 or 15.

Here, examples of the "nucleotide sequence modified by deletion, addition, insertion or substitution of one or a plurality of nucleotides" include nucleotide sequences that have, after the deletion, addition, insertion or substitution, 80% or more, 85% or more, 90% or more, 95% or more, 97% or more, 98% or more, or 99% or more sequence identity with the nucleotide sequence before the deletion, addition, insertion, or substitution. Examples of the specific number of nucleotides in the "one or a plurality of nucleotides" are 1 to 100, 1 to 50, 1 to 30, 1 to 10, and 1 to several (2, 3, 4, or 5). The deletion, addition, insertion, or substitution may be a combination thereof.

In one embodiment of the present invention, the BHLHE23 gene is a gene at a human chromosomal position "20q13.33" or at a murine chromosomal position "2103.34 cM". Those skilled in the art can determine the chromosomal position of the BHLHE23 gene (ortholog) in other animal species based, for example, on nucleotide sequences of genes listed in http://www.ncbi.nlm.nih.gov.

The BHLHE23 gene is preferably the human BHLHE23 gene or the murine BHLHE23 gene.

1-4. Genetic Modification

The "genetic modification" and the "modification of a gene" in the present invention mean elimination or attenuation of the expression or function of the mRNA or protein encoded by a particular gene by addition, insertion, deletion, substitution, or the like of one or a plurality of nucleotides to the particular gene. Accordingly, the genetic modification includes deletion of a gene(s). The number and the positions of nucleotides (including an enhancer(s), a promoter(s), an intron(s), and the like) to be added, inserted, deleted, substituted, or so and the method of the genetic modification are not limited, as long as the expression or function of the protein encoded by the particular gene is eliminated or attenuated.

In one embodiment of the present invention, the modification of the bipolar cell-regulating gene also includes substitution of a sequence encoding a protein (the exon and the intron) downstream of the enhancer and the promoter in the bipolar cell-regulating gene (for example, the ISL1 gene or the BHLHE23 gene) with a special sequence, while maintaining the enhancer and the promoter. Examples of the special sequence include suicide genes, survival regulatory genes, growth regulatory genes, differentiation regulatory genes, and metabolism regulatory genes, (hereinafter, also referred to as the "suicide genes and the like"), or genes encoding microRNAs that can suppress the expression of the bipolar cell-regulating gene, antisense RNAs containing nucleic acid sequences identical or homologous with the bipolar cell-regulating gene, and noncoding RNAs of the bipolar cell-regulating gene (hereinafter, also referred to as the "microRNA genes and the like"), or the like. Examples of the suicide genes and the like include genes for apoptosis inducing factors and the like. Examples of the microRNA genes and the like include genes encoding the microRNAs and the like against other bipolar cell-regulating genes. By expressing these genes under the promoter of a bipolar cell-regulating gene, for example, the induction of bipolar cell-specific cell death or the suppression of expression of a bipolar cell-regulating gene other than the replaced gene may be performed. Thus, the bipolar cells may be lead to cell death by the expression of one of the suicide genes and the like that has been incorporated downstream of the same enhancer and promoter at the time when the bipolar cell-regulating gene is expressed since the bipolar cell-regulating gene is expressed by the process inducing the bipolar cells. Moreover, the function of mRNA of the bipolar cell-regulating gene may be suppressed by expressing one of the microRNA genes and the like.

The special sequence may be substituted for the internal bipolar cell-regulating gene itself in pluripotent stem cells or may be introduced downstream of the enhancer and the promoter of the bipolar cell-regulating gene in the genome of pluripotent stem cells while maintaining the bipolar cell-regulating gene. In this case, the position of the introduction is not particularly limited, as long as it is a position at which the special sequence can function. Preferably, the special sequence is introduced, without substituting the bipolar cell-regulating gene itself.

In one embodiment, examples of the genetic modification include the genome editing that substantially eliminates the function from the gene. Examples of the "genome editing that substantially eliminates the function" include introduction of a mutation that modifies the gene into a mutated form and eliminates the function of the wild type (for example, a nonsense mutation such as frameshift), genome editing that decreases the expression level of the gene, and the like.

In one embodiment, examples of the "genome editing that decreases the expression level of the gene" include modification of an expression level regulatory sequence for a gene in genome, and the like. Examples of the expression level regulatory sequence include an enhancer and/or a promoter.

For example, the enhancer and/or promoter is present in the upstream sequence, in the downstream sequence, and/or within the gene (for example, an intronic region) of the bipolar cell-regulating gene.

The terms "gene deletion" and "deletion of gene" in the present invention mean eliminating or attenuating, by deleting a nucleotide(s) from a particular gene, the expression or function of the protein encoded by the particular gene. The number and the positions of the nucleotides (including an enhancer(s), a promoter(s), an intron(s), and the like) and the method of the gene deletion are not limited, as long as the expression or function of the protein encoded by the particular gene is eliminated or attenuated. For example, each of the murine and human ISL1 genes may be deleted by deleting the first and second exons and the murine BhIhb4 gene may be deleted by deleting a flanking sequence (for example, about 150 nucleotides) including the initiation codon of the protein coding region. For example, such a gene may be deleted by deleting some exons (for example, the first or second exon) or by deleting a plurality of nucleotides (1 to the total number of nucleotides in the protein coding region, for example, 10 to 500 nucleotides, 100 to 300 nucleotides, or about 150 nucleotides) including the initiation codon of the protein coding region.

In the present invention, genetic modification may be performed in a somatic cell before reprograming, a pluripotent stem cell, or a retinal cell. Examples of the method for obtaining a genetically modified retinal cell include a method involving inducing the differentiation of a genetically modified pluripotent stem cell (including a pluripotent stem cell obtained by reprograming a genetically modified somatic cell) and a method involving performing genetic modification in a retinal cell. Preferably, the genetic modification is performed in a pluripotent stem cell.

The "genetically modified pluripotent stem cell" in the present invention means a pluripotent stem cell in which genetic modification has been performed, within the extent that allows maintenance of pluripotency. In one embodiment, the "genetically modified pluripotent stem cell" means a pluripotent stem cell in which genetic modification has been performed within the extent that allows maintenance of pluripotency and proliferative capacity (self-renewal capacity).

In the present invention, the gene to be modified is the bipolar cell-regulating gene, but other genes may be further modified. One embodiment includes, but is not limited to, substitution of a particular cell marker gene with a gene encoding a fluorescence protein for the purpose of confirming the existence of the particular cell, and the like.

The genetically modified pluripotent stem cell or retinal cell may be produced, for example, by using a homologous recombination technique. The modification of a target gene on a chromosome may be performed by using a method described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual series 8, Gene targeting, Production of mutant mouse using embryonic stem cells, Yodosha Company, Ltd. (1995), and the like.

In a specific example, genomic DNA containing a target gene to be modified is isolated and a targeting vector for homologously recombining the target gene is prepared using isolated genomic DNA. By introducing the prepared targeting vector into a stem cell and selecting a cell in which homologous recombination between the target gene and the targeting vector has occurred, a stem cell in which the chromosomal gene has been modified may be prepared.

Examples of the method for isolating genomic DNA containing the target gene include known methods described in Molecular Cloning, A Laboratory Manual, Second Edition, Cold Spring Harbor Laboratory Press (1989) and Current Protocols in Molecular Biology, John Wiley & Sons (1987-1997). Genomic DNA containing the target gene may be isolated by using a genomic DNA library screening system (manufactured by Genome Systems), Universal GenomeWalker Kits (manufactured by CLONTECH), or the like. Instead of using genomic DNA, a polynucleotide encoding the target protein may be used. Such a polynucleotide may be obtained by amplifying an applicable polynucleotide by PCR.

The preparation of the targeting vector for homologously recombining the target gene and effective selection of homologous recombinants may be performed according to a method described in Gene Targeting, A Practical Approach, IRL Press at Oxford University Press (1993); Biomanual series 8, Gene targeting, Production of mutant mouse using embryonic stem cells, Yodosha Company, Ltd. (1995), and the like. The targeting vector either of a replacement type or an insertion type may be used. Examples of the method for selection include methods such as positive selection, promoter selection, negative selection, or poly A selection.

Examples of the method for selecting homologous recombinants of interest from selected cell lines include Southern hybridization with genomic DNA, PCR, and the like.

Moreover, the genetically modified pluripotent stem cell or retinal cell may be produced by genome editing. The genome editing is a genetic modification technique for gene-specific disruption, knock-in of a reporter gene, or the like by a technique such as the Zinc Finger system, the CRISPR/Cas9 system, and Transcription Activator-Like Effector Nucleases (TALEN).

In the Zinc Finger system, the target gene is usually recognized and cleaved by using artificial chimeric proteins composed of a domain referred to as the zinc finger motif that specifically binds to DNA and the restriction enzyme FokI. When the two artificial chimeric proteins have bound to the closely positioned target sequence, the DNA cleavage domains form a dimer to cleave DNA. The cleaved DNA is repaired by homologous recombination or non-homologous end-joining and the gene of interest is modified at the same time.

In the CRISPR/Cas9 genome editing system, an expression vector or mRNA of Cas9 (a DNA cleavage enzyme) or the Cas9 protein and an expression vector that expresses a guide RNA under the control of the polymerase III promoter or the like or the guide RNA itself are usually introduced into a cell. The guide RNA may be a fusion RNA of an RNA (crRNA) complementary to the target genome sequence and of tracrRNA. When a protospacer adjacent motif (PAM-sequence NGG) is present at the 3' end of the target genome sequence, Cas9 dissociates the DNA double strand, the target sequence is recognized by the guide RNA, and the both strands are cleaved. A mutation is introduced in the process of repairing the cleaved site.

The transcription activator-like effector nuclease (TALEN) is a system using the TAL effector, which the phytopathogenic bacterium *Xanthomonas* spp. produces. TALEN is usually an artificial nuclease that is a fusion of a DNA binding domain from the TAL effector and a DNA cleavage domain from the FokI nuclease. The DNA binding domain is composed of repeats of a 34 amino acid residue sequence and one repeat recognizes one nucleotide in the target DNA. The 12th and 13th amino acid residues in the repeat sequence are referred to as the repeat variable diresidues (RVD) and the sequence of them determines the target nucleotide. By designing TALEN such that 2 sets of TALEN molecules face each other on a particular sequence in the genome, the FokI domains dimerize on the target sequence and the TALEN pair exhibits the nuclease activity. The cleaved DNA double-strand is repaired by an intrinsic cellular mechanism and a mutation is introduced in the process. When genome editing is performed by TALEN, an expression vector or mRNA of TALEN is introduced into cells.

1-5. Pluripotent Stem Cell

In the present invention, the term "stem cells" means undifferentiated cells having differentiation potency and capacity to proliferate (in particular self-renewal capacity) while maintaining differentiation potency. The stem cells include subpopulations such as pluripotent stem cells, multipotent stem cells, and unipotent stem cells depending on the differentiation potency. The term "pluripotent stem cells" refers to stem cells that can be cultured in vitro and have the ability to differentiate to all the cell lineages belonging to the 3 blastoderms (the ectoderm, the mesoderm, the endoderm) and/or extraembryonic tissue (pluripotency). The term "multipotent stem cells" means stem cells having the ability to differentiate into a plurality, but not all, of tissues or cells. The term "unipotent stem cells" means stem cells having the ability to differentiate into a particular tissue or cell.

The pluripotent stem cells may be induced from fertilized eggs, clonal embryos, germline stem cells, tissue stem cells, somatic cells, and the like. Examples of the pluripotent stem cells include embryonic stem cells (ES cells), EG cells (Embryonic germ cells), induced pluripotent stem cells (iPS cells), and the like. The pluripotent stem cells also encompass Muse cells (Multi-lineage differentiating stress enduring cells) obtained by mesenchymal stem cells (MSCs) and GS cells prepared from germ cells (for example, the testis). The embryonic stem cells are established in 1981 for the first time and have also been applied to the production of knockout mice since 1989. Human embryonic stem cells were established in 1998 and have been used in regenerative medicine. The embryonic stem cells may be produced by culturing the internal cell mass with feeder cells or in a culture medium containing LIF (leukemia inhibitory factor). Methods for producing embryonic stem cells are described in, for example, WO96/22362, WO02/101057, U.S. Pat. Nos. 5,843,780, 6,200,806, 6,280,718, and the like. The embryonic stem cells are available from certain institutions and commercial products may also be purchased. For example, the human embryonic stem cells KhES-1, KhES-2, and KhES-3 are available from the Institute for Frontier Medical Sciences, Kyoto University. The human embryonic stem cell line Rx::Venus (derived from the cell line KhES-1) is available from the Institute of Physical and Chemical Research. The murine embryonic stem cell lines EB5 and D3 are respectively available from the Institute of Physical and Chemical Research and ATCC.

The nuclear transplantation embryonic stem cells (ntES cells), which are one of the embryonic stem cells, may be established from clonal embryos produced by transplanting a somatic nucleus to an ovum from which the nucleus is removed.

The EG cells may be produced by culturing primordial germ cells in a culture medium containing mSCF, LIF, and bFGF (Cell, 70: 841-847, 1992).

The "induced pluripotent stem cells" in the present invention are cells in which pluripotency is induced by reprogramming somatic cells by a known method. Specific examples thereof include cells obtained by reprogramming differentiated somatic cells such as a fibroblasts or peripheral blood mononuclear cells by expressing a combination of a plurality of genes selected from reprogramming genes including Oct3/4, Sox2, Klf4, Myc (c-Myc, N-Myc, L-Myc), Glis1, Nanog, Sall4, Lin28, and Esrrb to induce pluripotency. Examples of preferred combinations of reprogramming factors include (1) Oct3/4, Sox2, Klf4, and Myc (c-Myc or L-Myc), and (2) Oct3/4, Sox2, Klf4, Lin28, and L-Myc (Stem Cells, 2013, 31:458-466).

The induced pluripotent stem cells were established from murine cells by Yamanaka et al. in 2006 (Cell, 2006, 126 (4), pp. 663-676). The induced pluripotent stem cells were also established from human fibroblasts in 2007 and have pluripotency and self-renewal capacity like embryonic stem cells (Cell, 2007, 131 (5), pp. 861-872, Science, 2007, 318 (5858), pp. 1917-1920, Nat. Biotechnol., 2008, 26 (1), pp. 101-106).

The induced pluripotent stem cells may be induced from somatic cells by the addition of compounds, other than by a method of production by direct reprogramming by gene expression (Science, 2013, 341, pp. 651-654).

Moreover, established induced pluripotent stem cells are available and, for example, human induced pluripotent cell lines such as 201B7 cells, 201B7-Ff cells, 253G1 cells, 253G4 cells, 1201C1 cells, 1205D1 cells, 1210B2 cells, 1231A3 cells, and the like established in Kyoto University are available from Kyoto University. As Examples of the established induced pluripotent stem cells, Ff-I01 cells and Ff-I14 cells established at Kyoto University are available from Kyoto University.

Examples of the somatic cells to be used in the production of induced pluripotent stem cells include, but are not particularly limited to, fibroblasts, hematopoietic cells (for example, peripheral blood mononuclear cells (PBMCs), T cells), hepatocytes, pancreatic cells, intestinal epithelium cells, smooth muscle cells derived from tissue, and the like.

When reprogramming is performed by expression of several genes in the production of induced pluripotent stem cells, the means for expressing the genes is not particularly limited. Examples of the means include infection using a virus vector (for example, a retroviral vector, a lentiviral vector, a Sendai virus vector, an adenovirus vector, an adenoassociated virus vector), transfection (for example, the calcium phosphate method, lipofection, the RetroNectin method, electroporation) using a plasmid vector (for example, a plasmid vector, an episomal vector), transfection using an RNA vector (for example, the calcium phosphate method, lipofection, electroporation), direct injection of a protein (for example, a method using a needle, lipofection, electroporation), and the like.

The induced pluripotent stem cells may be produced in the presence of feeder cells or in the absence of feeder cells (feeder-free). In the production of the induced pluripotent stem cells in the presence of feeder cells, the induced pluripotent stem cells may be produced in the presence of an undifferentiated state-maintaining factor by a known method. The culture medium to be used in the production of induced pluripotent stem cells in the absence of feeder cells is not particularly limited, but examples thereof include maintenance culture media for known embryonic stem cells and/or induced pluripotent stem cells or culture media for establishing induced pluripotent stem cells in feeder-free conditions. Examples of the culture media for establishing induced pluripotent stem cells in feeder-free conditions include feeder-free culture medium such as the Essential 8 medium (E8 medium), the Essential 6 medium, the TeSR medium, the mTeSR medium, the mTeSR-E8 medium, the Stabilized Essential 8 medium, and the StemFit medium. In the production of induced pluripotent stem cells, the induced pluripotent stem cells may be produced, for example, by genetically introducing the 4 factors: Oct3/4, Sox2, Klf4, and Myc into somatic cells in feeder-free conditions using a Sendai virus vector.

The pluripotent stem cells to be used in the present invention are preferably embryonic stem cells or induced pluripotent stem cells and more preferably induced pluripotent stein cells.

The pluripotent stem cells to be used in the present invention are mammalian pluripotent stem cells, preferably rodent (for example, mouse or rat) or primate (for example, human or monkey) pluripotent stem cells, more preferably human or murine pluripotent stem cells, and further preferably human iPS cells or human ES cells.

Examples of the multipotent stem cells include tissue stem cells (referred to as tissue stem cells, tissue-specific stem cells, or somatic stem cells) such as hematopoietic stem cells, neural stem cells, retinal stem cells, and mesenchymal stem cells.

2. Regarding Culture of Cell Population for Transplant

One embodiment of the present invention provides a culture of a cell population for transplant, comprising: (1) the cell population for transplant and (2) a medium necessary to maintain viability of the cell population for transplant.

The "culture" in the present invention means a liquid that contains a medium necessary for maintaining viability and a cell population and may further contain a biological substance added or produced by the cell population. Examples of the biological substance include, but are not limited to, cytokines, chemokines, and the like.

Examples of the "medium necessary for maintaining viability" in the present invention include a culture medium and a physiological buffer solution, and the like, but the medium is not particularly limited as long as the cell population containing retinal cells such as retinal progenitor cells survives and those skilled in the art may select such a medium as appropriate. Examples thereof include culture media modified from basal media usually used for culture of animal cells. Examples of the basal media include culture media that may be used in culture of animal cells such as BME medium, BGJb medium, 1066 CMRL medium, Glasgow MEM (GMEM) medium, Improved MEM Zinc Option medium, IMDM medium, 199 Medium, Eagle MEM medium, αMEM medium, DMEM medium, F-12 medium, DMEM/F12 medium, IMDM/F12 medium, Ham's medium, RPMI 1640 medium, Fischer's medium, or mixed culture media thereof.

3. Regarding Method for Producing Cell Population for Transplant containing Retinal Cell One embodiment of the present invention is a method for producing a cell population for transplant comprising retinal cells, comprising the following steps (1) and (2):

(1) modifying a bipolar cell-regulating gene of pluripotent stem cells to obtain in vitro, a cell population comprising the pluripotent stem cells with the modified bipolar cell-regulating gene;

(2) inducing differentiation of the cell population comprising the pluripotent stem cells obtained in step (1) into retinal cells in vitro to obtain a cell population for transplant comprising the retinal cells.

As used herein, "modifying a bipolar cell-regulating gene of a pluripotent stem cells" includes an embodiment involving modifying a bipolar cell-regulating gene in a somatic cell before reprogramming, and then producing a pluripotent stem cell having a modified bipolar cell-regulating gene by reprograming the somatic cell before reprogramming.

Those skilled in the art may store the cell population obtained in step (1) by a well known method. The stored cell population is a raw material or a production intermediate for obtaining retinal cells with a modified bipolar cell-regulating gene. One embodiment of the present invention provides the raw material or production intermediate of retinal cells with a modified bipolar cell-regulating gene.

Examples of the method for storing the cell population obtained in step (1) include cryopreservation. The method for cryopreservation is not particularly limited, as long as it is a method generally known as a method for cryopreserving cells. For example, the cell population obtained in step (1) may be suspended in a culture medium containing a cryoprotective agent such as DMSO or glycerin and cryopreserved. Moreover, a commercially available cell cryopreservation medium "StemCellBanker (Nippon Zenyaku Kogyo Co., Ltd., registered trademark)" may also be used. The long-term preservation of cell population is possible by cryopreservation.

One embodiment of the present invention provides, as a raw material or a production intermediate for obtaining retinal cells with a modified bipolar cell-regulating, a master cell bank or a working cell bank of cell population containing a pluripotent stem cell with a modified bipolar cell-regulating gene.

More specifically, it is possible to produce the master cell bank by expanding a cell obtained in step (1) and then cryopreserving the resulting cells. Furthermore, the working cell bank may be produced by expanding a cell thawed from the master cell bank. For producing the master cell bank and the working cell bank, the smaller passage number of cells is preferred.

Here, the "master cell bank" refers to a preparation obtained by expanding a seed cell line that serves as an origin of all cell seeds for production and dispensing the resulting cells into a plurality of ampules. Moreover, the "working cell bank" refers to a preparation obtained by expanding one or a plurality of cells reactivated from the master cell bank and dispensing the resulting cells into a plurality of ampules.

One embodiment of the present invention provides a method for producing a raw material or a production intermediate for retinal cells with a modified bipolar cell-regulating gene (for example, a master cell bank of a cell population(s) containing a pluripotent stem cells with a modified bipolar cell-regulating gene), comprising the following steps (i) to (iii):

(i) modifying a bipolar cell-regulating gene of a pluripotent stem cells to obtain in vitro, a cell population of the pluripotent stem cell with a modified bipolar cell-regulating gene;

(ii) proliferating the cell population of the pluripotent stem cell obtained in step (i) by culture, (iii) cryopreserving the cell population of the pluripotent stem cell obtained in step (ii).

It is possible to provide the cryopreserved cell population (including the master cell bank or working cell bank) of pluripotent stem cells with a modified bipolar cell-regulating gene to step (2) after thawing. Those skilled in the art may thaw frozen cells by a well known method. An unfrozen or frozen or thawed-after-freezing cell population of pluripotent stem cell with a modified bipolar cell-regulating gene is also one embodiment of the present invention.

Accordingly, another one embodiment of the present invention is a method for producing a cell population comprising retinal cells, comprising the following steps (iv) and (v):

(iv) thawing a cryopreserved cell population of pluripotent stem cell with a modified bipolar cell-regulating gene, (v) inducing differentiation of the cell population comprising the pluripotent stem cells obtained in step (iv) into the retinal cells in vitro to obtain a cell population for transplant comprising the retinal cells.

Step (1) and (2) will be described in detail below.

3-1. Regarding Step (1)

Preferable examples of the pluripotent stem cells in step (1) include iPS cells or ES cells.

Here, the method for producing the iPS cells or ES cells is not particularly limited and the iPS cells or ES cells may be produced by a method well known to those skilled in the art as described above. Preferably, the production is conducted in the absence of feeder cells (feeder-free).

In the present invention, "the production is conducted in the absence of feeder cells (feeder-free)" means culturing in the absence of feeder cells. Examples of being in the absence of feeder cells include conditions in which feeder cells are not added or conditions in which feeder cells are substantially absent (for example, the proportion of the number of feeder cells to the total number of cells is 3% or less and preferably 0.5% or less).

In step (I), the maintenance culture or expansion of pluripotent stem cells may be conducted depending on need. The maintenance culture or expansion may be conducted by a method well known to those skilled in the art, but preferably conducted feeder-free.

The culture medium used in the maintenance culture or expansion of the pluripotent stem cells is not limited as long as the maintenance culture or expansion is possible. Under feeder-free conditions, a culture medium containing an undifferentiated state-maintaining factor for enabling undifferentiated state-maintenance culture is used, and many synthetic culture media have been developed and marketed, which may be used. Examples thereof include Essential 8 (manufactured by Life Technologies) medium, S-medium (manufactured by DS Pharma Biomedical Co., Ltd.), StemPro (manufactured by Life Technologies, registered trademark), hESF9 (Proc Natl Acad Sci USA. 2008, Sep. 9, 105 (36): 13409-14), mTeSR1 (manufactured by STEMCELL Technologies Inc.), mTeSR2 (manufactured by STEMCELL Technologies Inc.), TeSR-E8 (manufactured by STEMCELL Technologies Inc.), and StemFit (manufactured by Ajinomoto Co., Inc., registered trademark).

The genetic modification in step (1) may be conducted by a method well known to those skilled in the art as described above.

Those skilled in the art can determine how to modify the bipolar cell-regulating gene for eliminating or attenuating the expression or function of the bipolar cell-regulating gene.

One embodiment for eliminating or attenuating the expression or function of the bipolar cell-regulating gene includes gene deletion of the bipolar cell-regulating gene. In this embodiment, a part or all of the nucleotide sequence of the bipolar cell-regulating gene is deleted. Examples of the deletion of a part of the nucleotide sequence include partial deletion of a region containing the transcription initiation codon or a region important for the function of the protein. It is possible to substitute a part or all of the nucleotide sequence of the bipolar cell-regulating gene, for example, with a drug-resistant gene or a fluorescence protein, for selecting a pluripotent stem cell having gene deletion.

Those skilled in the art can easily confirm that a gene is modified. One embodiment includes Southern blotting, PCR (Polymerase Chain Reaction), and sequencing.

Those skilled in the art can select genetically modified pluripotent stem cells. One embodiment includes a method involving introducing a drug resistance gene such as the neomycin resistance gene or a gene encoding fluorescence proteins such as GFP in genetic modification and selecting a genetically modified cell with a drug or the fluorescence of GFP.

The genetically modified pluripotent stem cell obtained in step (1) may be subjected to maintenance culture, expansion, storage, or another treatment before shifting to step (2), as long as its viable state and pluripotency is maintained.

The maintenance culture, expansion, and storage may be conducted by a method well known to those skilled in the art, such as the method described above.

When using cryopreserved pluripotent stem cells with a modified bipolar cell-regulating gene, step (1) may be replaced with a step of thawing the frozen cells.

Those skilled in the art can thaw cryopreserved cells by a well known method and use the thawed cells in step (2). In one embodiment, the cryopreserved cells may be thawed and then subjected to maintenance culture or expansion.

3-2. Regarding Step (2)

Specific examples of the method for obtaining a cell population for transplant comprising retinal cells from the cell population obtained in step (1) will be described. Examples of the method for inducing differentiation in the aforementioned step (2) include, but are not limited to, methods disclosed in WO2011/055855, WO2012/173207, WO2013/077425, WO2015/025967, WO2016/063985, WO2016/063986, PLoS One. 2010 Jan. 20; 5 (1): e8763., Stem Cells. 2011 Aug. 29 (8): 1206-18, Proc Natl Acad Sci USA 2014 Jun. 10, 111 (23): 8518-23, Nat Commun. 2014 Jun. 10; 5: 4047. The pluripotent stem cell in which the bipolar cell-regulating gene has been modified by a method known to those skilled in the art may be subjected to other methods for inducing differentiation into a cell population for transplant comprising retinal cells or retinal tissue.

In one embodiment of step (2), a cell aggregate containing retinal cells may be obtained by the following steps (A) to (C).

(A): culturing the cell population of genetically modified pluripotent stem cells obtained in step (1) in suspension in a serum-free culture medium containing a Wnt signaling pathway inhibitor to form a cell aggregate of pluripotent stem cells, (B): culturing the cell aggregate obtained in step (A) in suspension in a serum-free culture medium containing a basement membrane preparation, (C): culturing the cell aggregate obtained in step (B) in suspension in a serum culture medium.

This method is disclosed, for example, in WO2013/077425, and WO2013/077425 may be referred to for greater detail.

The "serum-free culture medium" in the present invention means a culture medium not containing unadjusted or unpurified serum. In the present invention, a culture medium containing a purified ingredient derived from blood or derived from animal tissue (for example, a growth factor) is also included in the serum-free culture medium unless the culture medium contains unadjusted or unpurified serum.

As such a serum-free culture medium, a serum-free culture medium containing a proper amount (for example, about 0.5% to about 30%, preferably about 1% to about 20% in volume percentage) of commercially available KSR (manufactured by Life Technologies, trade name) may be used.

The Wnt signaling pathway inhibitor is not particularly limited, as long as it can suppress the signal transduction mediated by Wnt. For example, CKI-7 (N-(2-aminoethyl)-5-chloro-isoquinoline-8-sulfonamide), IWR-1-endo (IWR1e) are known Wnt signaling pathway inhibitors and commercially available as appropriate. Preferably, IWR1e is used as a Wnt signaling pathway inhibitor.

The concentration of the Wnt signaling pathway inhibitor to be used may be a concentration at which an aggregate of pluripotent stem cells is formed. For example, IWR1e is added to a culture medium at a concentration of about 0.1 μM to 100 μM, preferably about 1 μM to 10 μM, more preferably about 3 μM.

The Wnt signal pathway inhibitor may be added to a serum-free culture medium before starting the suspension culture. Moreover, it may be added to a serum-free culture medium within several days (for example, within 5 days) after starting the suspension culture. Preferably, the Wnt signal pathway inhibitor is added to a serum-free culture medium within 5 days, more preferably within 3 days after starting the suspension culture, and most preferably at the same time as starting the suspension culture. Moreover, the suspension culture is continued in the presence of the Wnt signal pathway inhibitor, preferably until the 18th day and more preferably until the 12th day after starting the suspension culture.

Examples of the experimental operation for forming the aggregate include a method involving trapping cells in a small space using a plate with small wells (96-well plate), micropores, or the like, a method involving aggregating cells by centrifugation for a short time using a small centrifuging tube, and the like.

When forming cell aggregates, the number of the pluripotent stem cells is not particularly limited as long as it allows formation of homogeneous aggregates of stem cells. For example, when using 96-well microwell plates, a liquid prepared at about $1\times10^3$ to about $5\times10^4$ cells, preferably about $3\times10^3$ to about $3\times10^4$ cells, more preferably about $5\times10^3$ to about $2\times10^4$ cells, most preferably around $9\times10^3$ cells per well is added and the plate is left stand to allow the formation of cell aggregates.

The formation of aggregates of pluripotent stem cells can be determined by a person skilled in the art based on the size and the number of cells of the cell aggregates, the macroscopic morphology, the microscopic morphology and uniformity detected by the tissue staining analysis, the expression of differentiation and undifferentiation marker and the uniformity thereof, the regulation of expression of a differentiation marker and the synchronism, the reproducibility of differentiation efficiency between aggregates, and the like.

The basement membrane preparation refers to a preparation containing a basement membrane component having the function of controlling an epithelial cell-like cellular morphology, differentiation, proliferation, mobility, functional expression, and/or the like, when desired cells having basement membrane-forming ability are seeded and cultured thereon. Here, the "basement membrane component" refers to an extracellular matrix molecule in the form of thin film present between the epithelium cell layer and the stroma cell layer in animal tissue. The basement membrane preparation may be prepared, for example, by removing the cells having basement membrane-foaming ability adhering on a support via a basement membrane using a solution that can lyse lipids of the cell or an alkaline solution. Examples of a preferred basement membrane preparation include products commercially available as basement membrane components (for example, Matrigel) or a preparation containing an extracellular matrix molecule known as a basement membrane component (for example, laminin, type IV collagen, heparan sulfate proteoglycan, entactin, or the like).

Examples of the amount of the basement membrane preparation to be used include preferably an amount of 1/20 to 1/200, more preferably an amount of around 1/100, based on the volume of culture medium, when Matrigel is used. The basement membrane preparation may have been already added to a culture medium at the time of starting the culture of stem cells or be added to a serum-free culture medium, preferably within 5 days after starting the suspension culture and more preferably within 2 days after starting the suspension culture.

Examples of the serum that may be used include mammalian sera such as bovine serum, calf serum, fetal bovine serum, horse serum, foal serum, fetal horse serum, rabbit serum, leveret serum, fetal rabbit serum, and human serum.

The addition of the serum is conducted on the 7th day or later, more preferably on the 9th day or later, and most preferably on the 12th day after starting the suspension culture. The serum is added so that the concentration will be about 1 to 30%, preferably about 3 to 20%, more preferably around 10% (for example, 5% to 15%), in volume percentage.

In another embodiment of step (2), it is possible to obtain a cell aggregate containing retinal cells by a method comprising the following steps (D), (E) and (F).

(D): culturing the pluripotent stem cells with a modified bipolar cell-regulating gene obtained in step (1) in the absence of feeder cells in a culture medium containing 1) a TGFβ family signaling pathway inhibitor and/or a Sonic Hedgehog signaling pathway agent, and 2) an undifferentiated state-maintaining factor, (E): culturing the pluripotent stem cells with a modified bipolar cell-regulating gene cultured in step (D) in a serum-free culture medium in suspension to form a cell aggregate, (F): further culturing the cell aggregate obtained in step (E) in suspension in a culture medium containing a BMP signaling pathway agent.

This method is disclosed, for example, in WO2016/063985, and WO2016/063985 may be referred to for greater detail.

The TGFβ family signaling pathway inhibitor refers to a substance that inhibits the TGF13 family signaling pathway, that is, a signaling pathway transmitted by the Smad family, and specific examples thereof include TGFβ signaling pathway inhibitors (for example, SB431542, LY-364947, SB-505124, A-83-01), Nodal/Activin signaling pathway inhibitors (for example, SB431542, A-83-01), and BMP signaling pathway inhibitors (for example, LDN193189, Dorsomorphin). These substances are marketed and available.

The Sonic Hedgehog (hereinafter, referred to as the "Shh".) signaling pathway agent is a substance that can enhance the signaling transmitted by Shh. Examples of the Shh signaling pathway agent include PMA (Purmorphamine), SAG (Smoothened Agonist), and the like.

The concentration of the TGFβ family signaling pathway inhibitor and the Sonic Hedgehog signaling pathway agent may be a concentration that can induce the differentiation into retinal cells. For example, SB431542 is usually used at a concentration of 0.1 to 200 μM and preferably 2 to 50 μM.

A-83-01 is usually used at a concentration of 0.05 to 50 μM and preferably 0.5 to 5 μM. LDN193189 is usually used at a concentration of 1 to 2000 nM and preferably 10 to 300 nM. SAG is usually used at a concentration of 1 to 2000 nM and preferably 10 to 700 nM. PMA is usually used at a concentration of 0.002 to 20 μM and preferably 0.02 to 2 μM.

In culturing the pluripotent stem cell under feeder-free conditions in step (D), the feeder-free culture medium containing an undifferentiated state-maintaining factor may be used as a culture medium.

In culturing the pluripotent stem cell under feeder-free conditions in step (D), an appropriate matrix may be used as, a scaffold to provide a scaffold for pluripotent stem cells in the place of feeder cells. Examples of matrices that may be used as a scaffold include Laminin (Nat Biotechnol 28, 611-615, (2010)), Laminin fragments (Nat Commun 3, 1236, (2012)), a basement membrane preparation (Nat Biotechnol 19, 971-974, (2001)), gelatin, collagen, heparan sulfate proteoglycan, entactin, vitronectin, and the like.

The culture time of pluripotent stem cells in step (D) is not particularly limited, as long as it is within the range that allows improvement of the quality of cell aggregates Banned in step (E), but it is usually 0.5 to 144 hours. In one embodiment, the culture time is preferably 2 to 96 hours, more preferably 6 to 48 hours, further preferably 12 to 48 hours, and even more preferably 18 to 28 hours (for example, 24 hours).

The preparation of the serum-free culture medium and the formation of the cell aggregate may be performed as described above.

In one embodiment, the culture medium used in step (E) comprises a Sonic Hedgehog signaling pathway agent. As the Sonic Hedgehog signaling pathway agent, those described above may be used at a concentration described above. The Sonic Hedgehog signaling pathway agent is preferably contained in the culture medium from the start of the suspension culture. A ROCK inhibitor (for example, Y-27632) may be added to the culture medium. The culture time is, for example, 12 hours to 6 days.

The BMP signaling pathway agent is a substance that can enhance a signaling pathway transmitted by BMP. Examples of the BMP signaling pathway agent include a BMP protein such as BMP2, BMP4, or BMP7, a GDF protein such as GDF7, an anti-BMP receptor antibody, or a partial BMP peptide. The BMP2 protein, the BMP4 protein, and the BMP7 protein are available, for example, from R&D Systems, Inc. and the GDF7 protein is available, for example, from Wako Pure Chemical Industries, Ltd.

Examples of the culture medium to be used include serum-free culture media or serum culture media (preferably serum-free culture media) in which the BMP signaling pathway agent is added. The serum-free culture media and the serum culture media may be prepared as described above.

The concentration of the BMP signaling pathway agent may be a concentration that can induce the differentiation into retinal cells. For example, the human BMP4 protein is added to a culture medium at a concentration of about 0.01 nM to about 1 μM, preferably about 0.1 nM to about 100 nM, more preferably about 1 nM to about 10 nM, and more preferably about 1.5 nM (55 ng/mL).

The BMP signaling pathway agent may be added to a culture medium about 24 hours or more after starting the suspension culture in step (D), and for example, it may be added to a culture medium within several days (for example, within 15 days) after starting the suspension culture. Preferably, the BMP signaling pathway agent may be added to a culture medium between the 1st day and the 15th day, more preferably between the 1st day and the 9th day, most preferably the 3rd day after starting the suspension culture.

The culture conditions such as the culture temperature and the $CO_2$ concentration in step (A) to step (F) may be set as appropriate. The culture temperature is, for example, about 30° C. to about 40° C. and preferably about 37° C. Moreover, the $CO_2$ concentration is, for example, about 1% to about 10% and preferably about 5%.

It is possible to produce retinal cells at various differentiation stages by changing the culture period in step (C) or step (F) described above. Accordingly, it is possible to produce retinal cells comprising immature retinal cells (for example, retinal progenitor cells or photoreceptor precursor cells) and mature retinal cells (for example, photoreceptor cells) at various ratios. It is possible to increase the ratio of mature retinal cells by extending the culture period of step (C) or step (F).

It is also possible to produce a ciliary marginal zone-like structure by culturing the cell aggregate of retinal cells obtained in the method described above in the presence or absence of the BMP signaling pathway agent in a serum-free culture medium or a serum culture medium containing the Wnt signaling pathway agent and/or the FGF signaling pathway inhibitor for a time period of from about 3 days to 6 days and then in a serum-free culture medium or a serum culture medium containing neither Wnt signaling pathway agent nor FGF signaling pathway inhibitor for from about 30 days to 60 days.

The ciliary marginal zone-like structure is a structure similar to the ciliary marginal zone. Examples of the "ciliary marginal zone (CMZ)" include a region of a retina that is a tissue present in the border region between the retinal tissue (specifically the neural retina) and the retinal pigment epithelium in the retina in vivo and that contains tissue stem cells (retinal stem cells). The ciliary marginal zone is also called as the ciliary margin or the retinal margin. It is known that the ciliary marginal zone plays an important role in the supply of retinal progenitor cells or differentiated cells to retinal tissue and the maintenance of retinal tissue structure. Examples of marker genes for the ciliary marginal zone include the Rdh10 gene (positive), the Otx1 gene (positive), and the Zic1 (positive).

The Wnt signaling pathway agent is not particularly limited, as long as it can enhance the signal transduction transmitted by Wnt. Specific examples of the Wnt signaling pathway agent include a GSK3β inhibitor (for example, 6-Bromoindirubin-3'-oxime (BIO), CHIR99021, Kenpaullone). For example, CHIR99021 is added at a concentration of about 0.1 μM to about 100 μM and preferably about 1 μM to about 30 μM.

The FGF signaling pathway inhibitor is not particularly limited, as long as it can inhibit the signal transduction transmitted by FGF. Examples of the FGF signaling pathway inhibitor include SU-5402, AZD4547, BGJ398, and the like. For example, SU-5402 is added at a concentration of about 0.1 μM to about 100 μM, preferably about 1 μM to about 30 μM, and more preferably about 5 μM.

The retinal cells with a modified bipolar cell-regulating gene may be produced by a method described above, but it is not limited to these methods.

In the cell population for transplant comprising the retinal cell obtained in step (2), the sum of the number of retinal progenitor cells, photoreceptor precursor cells, and photoreceptor cells is 10% or more (preferably 20% or more, 30% or more, 40% or more, 50% or more, 60% or more, 70% or more, 80% or more, or 90% or more) of the total number of cells. Moreover, when continuing the culture of the cell population for transplant comprising the retinal cell obtained in step (2) (for example, after 120 days from the start of step (2)), or when transplanting the cell population for transplant comprising the retinal cell obtained in step (2) into the living body, the neural retinal layer is formed and cells that constitute the neural retinal layer increase in a retina in vitro or in a transplanted recipient retina. At this stage, the sum of the number of retinal progenitor cells, photoreceptor precursor cells, and photoreceptor cells may be 30% or more (preferably 40% or more or 50% or more) of the total number of cells, and the sum of the numbers of bipolar cells precursor cells, cone bipolar cells, and rod bipolar cells may be 30% or less (preferably 20% or less, 10% or less, or 5% or less) of the total number of cells. Moreover, the ratio of the number of bipolar cells to the number of amacrine cells decreases (for example, 70% or less, 60% or less, or 50% or less).

In one embodiment of the present invention, the retinal progenitor cells are Chx10-positive cells, the photoreceptor precursor cells are Crx-positive cells, and the photoreceptor cells are Recoverin-positive cells.

Those skilled in the art can measure the ratio of retinal progenitor cells, photoreceptor precursor cells, and photoreceptor cells in the cell population obtained in step (2) by a well known method. In one embodiment, it is possible to measure the ratio of Chx10-positive cells, Crx-positive cells, Recoverin-positive cells contained by a method such as immunohistochemistry or flow cytometry.

Those skilled in the art can confirm that the modification of the bipolar cell-regulating gene is maintained by a well known method, for example, the method described above.

The undifferentiation into bipolar cells or degenerative death of bipolar cells may be confirmed, for example, based on the presence or absence of the expression of the bipolar cell marker PKCα, Chx10, or the like determined by the method such as immunohistochemistry or flow cytometry.

The dysfunction of bipolar cells may be confirmed by a method such as immunohistochemical analysis or electrophysiological analysis. For example, if the synaptic connection with photoreceptor cells or neuronal firing is not observed, it is possible to determine that bipolar cells are dysfunctional.

Moreover, it is possible to confirm that normal photoreceptor cells are induced, for example, based on the presence or absence of the expression of the photoreceptor cell marker Recoverin or the like determined by a method such as immunohistochemistry or flow cytometry.

The presence or absence of the aforementioned cells and the ratio thereof may also be confirmed from tissue after the transplant.

4. Regarding Transplant of Cell Population for Transplant comprising Retinal Cell The cell population for transplant comprising a retinal cell produced by the method described above may be transplanted into a subject (for example, a mammal) in need of transplant and it is possible to improve the visual function of the subject by the transplant. Examples of a mammalian animal that may be a subject include a human, a mouse, a rat, a guinea pig, a hamster, a rabbit, a cat, a dog, a sheep, a pig, a cow, a horse, a goat, a monkey, and the like.

The cell population for transplant comprising retinal cells may be transplanted in the form of a cell aggregate. Moreover, it is possible to cut the retinal tissue that is obtained in the method of production according to the present invention into appropriate size using tweezers, a knife, scissors, or the like to make a sheet agent (a cell sheet) and then transplant the agent. Examples thereof include transplanting one or a plurality of pieces of the cell sheet (for example, 300 μm in diameter, 50 μm in height) cut out from one cell aggregate depending on the area of the region in which photoreceptor cells are degenerated. Those skilled in the art can select the number of pieces of the cell sheet depending on the area of the region of degenerative death. Furthermore, it is possible to subject the produced retinal cells to an operation such as an enzymatic treatment or pipetting and transplant the cells in a form of cell suspension.

The cell population for transplant comprising retinal cells is transplanted preferably after being made into a pharmaceutical composition.

The transplant of the cell suspension is carried out, for example, by a method involving transplanting the cell suspension under retina using a needle. The transplantation of the cell sheet is carried out, for example, by incising a part of the eyeball and transplanting the cell sheet to the damaged site or lesion site through the incision.

After transplantation, at least a part of integrated immature retinal cells is induced to differentiate into mature retinal cells in the in vivo (intraocular) environment of the subject. Here, the "photoreceptor cells induced after transplantation" means photoreceptor cells induced and differentiated from integrated retinal progenitor cells or photoreceptor precursor cells after transplantation in the eye of the subject.

Here, the "integration" in the present invention means that the transplanted cells survive in the living body for a long period of time (for example, 30 days or more, 60 days or more, or 90 days or more) and are adhered to and remain in the organ.

The "functional integration" in the present invention means a state in which the transplanted cells are integrated and perform their original function in the body.

The original function of the photoreceptor cells is to come in contact with bipolar cells to form the synapse in the body and to transmit electrical signals converted in the photoreceptor cells to bipolar cells. Therefore, the "functional integration of photoreceptor cells" in the present invention means that transplanted photoreceptor cells (including photoreceptor cells induced after transplantation) is integrated in a state in which the photoreceptor cells come in contact with host bipolar cells to form the synapse and electrical signals converted in the photoreceptor cells are transmitted to bipolar cells through the synapse. It is possible to confirm that photoreceptor cells and bipolar cells have formed the synapse by staining a photoreceptor cell synaptic marker (for example, Ctbp2, Basoon, Cacna1f, ELFN1) or a bipolar cell synaptic marker (for example, mGluR6, Cacnals, TRPM1). Specifically, it is possible to confirm the synapse formation by staining the aforementioned synapse marker on the contact surface of Recoverin-positive cells (photoreceptor cells) and PKCα-positive cells (bipolar cells) by a technique such as immunostaining. In the present invention, the state in which the photoreceptor cell layer in the transplant come in contact with the retinal layer containing host bipolar cells may be considered as the functional integration of photoreceptor cells (Stem Cells, 31, 1149-1159, (2013)).

The "contact" in the present invention refers to the state in which cells are physically in close proximity and the synaptic connection is suggested.

The "ratio of contact" in the present invention refers to the ratio of length of contact between the photoreceptor cell layer in the transplanted retinal tissue and the retinal layer containing host bipolar cells to the length of a longer side of the transplanted retinal tissue.

The "functional integration rate" in the present invention means the ratio of the cells that have achieved functional integration to the cells transplanted. The functional integration rate of transplanted photoreceptor cells may be determined from the aforementioned contact ratio.

The functional integration rate of transplanted photoreceptor cells (including photoreceptor cells induced after transplantation) by transplanting the cell population for transplant comprising retinal cells produced by the method according to the present invention is 10% or more, preferably 20% or more, more preferably 40% or more, further preferably 50% or more, and particularly preferably 60% or more.

The higher the integration rate and/or the functional integration rate of transplanted photoreceptor cells (including photoreceptor cells induced after transplantation) is, the greater the improvement of the visual function after the transplantation.

Accordingly, the present invention provides a method for improving the integration rate and/or the functional integration rate of transplanted photoreceptor cells (including photoreceptor cells induced after transplantation).

5. Pharmaceutical Composition

The present invention provides a pharmaceutical composition comprising an effective amount of a cell population for transplant comprising retinal cells produced by the aforementioned method of production. The effective amount of the cell population for transplant varies depending on the purpose of administration, the mode of administration, and the state (sex, age, body weight, conditions) of the subject of administration, but may be, for example, $1\times10^5$ to $1\times10^7$ cells (for example, $1\times10^5$ cells, $1\times10^6$ cells, or $1\times10^7$ cells) in the number of cells.

The pharmaceutical composition comprises an effective amount of the aforementioned cell population for transplant produced by the method of production according to the present invention and a pharmaceutically acceptable carrier.

As the pharmaceutically acceptable carrier, a physiological aqueous solvent (physiological saline, buffer solution, a serum-free culture medium, or the like) may be used. A preservative, a stabilizer, a reducing agent, an isotonizing agent, or the like that is usually used in medicaments in transplant medicine containing tissue or cells to be transplanted may be added to the pharmaceutical composition as needed.

The pharmaceutical composition according to the present invention may be produced as a cell suspension by suspending the aforementioned cell population for transplant produced by the aforementioned method of production with an appropriate physiological aqueous solvent. If needed, it is also possible to add a cryoprotective agent to the aforementioned cell population for transplant to cryopreserve the cell population, thaw the cryopreserved cell population before using, wash the thawed cell population with a buffer solution, and use it for transplant medicine.

The retinal tissue comprising the cell population for transplant that is obtained by the method of production according to the present invention may be cut into appropriate size using tweezers, a knife, scissors, or the like to make it a sheet agent.

Moreover, the cell population for transplant that is obtained by the method of production according to the present invention may also be formed into a sheet to make it a sheet agent that is a cell sheet, by conducting the adherent culture in step (2) of inducing differentiation.

The pharmaceutical composition according to the present invention is useful as a therapeutic agent for diseases based on disorders of retinal cells.

6. Therapeutic Agent and Method of Treatment

The cell population for transplant comprising retinal cells produced by the method of production according to the present invention is useful in transplant medicine for diseases based on disorders of retinal tissue (including disorders of retinal progenitor cells or retinal cells). Accordingly, the present invention provides a therapeutic agent for a disease based on a disorder of retinal tissue, comprising a cell population for transplant comprising retinal cells produced by the method of production according to the present invention. Moreover, the present invention provides a method of treatment, comprising administering (transplanting) the therapeutic agent in the form of a suspension or a sheet agent to a patient. The cell population for transplant comprising retinal cells produced by the method of production according to the present invention may be used as a therapeutic agent for a disease based on a disorder of retinal tissue or for supplementing the damaged site in a condition of retinal tissue damage. It is possible to treat diseases based on a disorder of retinal tissue or a condition of retinal tissue damage by transplanting a cell population for transplant comprising retinal cells produced by the method of production according to the present invention to a patient in need of transplantation with a disease based on a disorder of retinal tissue or a condition of retinal tissue damage and supplementing the retinal cells or damaged retinal tissue itself. Examples of the disease based on a disorder of retinal tissue include eye diseases such as macular degeneration, age-related macular degeneration, retinitis pigmentosa, glaucoma, corneal disease, retinal detachment, central serous chorioretinopathy, cone dystrophy, cone-rod dystrophy, and the like. Examples of the condition of retinal tissue damage include the condition in which photoreceptor cells are dead in degeneration, and the like.

While the rejection due to the difference in histocompatible antigens often becomes the problem in transplant medicine, it is possible to overcome the problem by using pluripotent stem cells (for example, induced pluripotent stem cells) established from somatic cells of the recipient of the transplantation. Accordingly, in a preferred embodiment of the present invention, immunologically autologous retinal tissue or retinal cells for the recipient are produced by using pluripotent stem cells (for example, induced pluripotent stem cells) established from somatic cells of the recipient as pluripotent stem cells, and are transplanted into the recipient.

Moreover, allo (non autologous) retinal tissue or retinal cells may be prepared from pluripotent stem cells (for example, induced pluripotent stem cells) established from somatic cells of a nonself who is immunologically compatible (for example, having a compatible HLA or MHC type) with the recipient and transplanted to the recipient.

EXAMPLES

Hereinafter, the present invention is described in detail in reference with examples but is not limited thereto.

Example 1: Example of Transplanting the Retinal Tissue Derived from Mouse iPS Cells wherein the Function of a Bhlhb4 Gene is Deleted to Reduce Rod Bipolar Cells in the Transplanted Tissue Mouse iPS cells (Stem Cells, 31, 1149-1159, (2013), Proc. Natl. Acad. Sci. USA, 103, pp. 3890-3895, (2006)) having an Nr1::eGFP reporter established from an Nr1::eGFP mouse were cultured while maintaining undifferentiated state in accordance with the method described in Nature biotechnology, 26(2), 215-24, (2008).

A CRISPR/Cas9 system was used as a method for causing loss of function of a BhIhb4 gene (mouse ortholog of BHLHE23 gene). The target sequence sites can be cleaved by intracellular expression of SpCas9 and target sequences sgRNA (SEQ ID NO 16: ccgagctcaagtcgctgtcg, SEQ ID NO: 17 cgcgccttggtgagaaggcg). A plasmid into which SpCas9 and the target sequences were incorporated was introduced to mouse iPS cells by electroporation (product name: Nucreofector, manufactured by Lonza). CRISPR/Cas9, gRNA designed so as to delete a region comprising an initiation codon of the BhIhb4 gene, and a plasmid into which a puromycin-resistance gene was incorporated were introduced to the mouse iPS cells. The introduced cells were selected using puromycin and colonies were picked up, whereby a BhIhb4 gene-deleted line was established. The deletion at the sites of interest in the BhIhb4 gene was continued by PCR and agarose gel electrophoresis, or by reading the nucleotide sequence information.

SFEBq method described in Non Patent Literature 5, which is the modified method described in Non Patent Literature 2, was used as the method for inducing differentiation into the retina. The induction of differentiation was operated as follows. Mouse iPS cells were enzymatically treated and dispersed into single cells, and subsequently suspension cultured in a 96-well plate at 3000 cells/well. From day 0 to day 1 after the initiation of differentiation, the above cells were cultured in a culture medium to which AGN193109 (0.1 μM, manufactured by Toronto Research Chemicals) was added, and subsequently up to day 8 the above cells were cultured in a culture medium to which AGN193109 and Growth Factor Reduced Matrigel (2% v/v, manufactured by BD Biosciences) were added. Note that the "day N after the initiation of differentiation" refers to a period from N days after (N×24 hours after) the initiation of differentiation to immediately before N+1 day ((N+1)×24 hours) have passed (the same applies hereinafter). For the culture medium, G-MEM (5% KSR, 0.1 mM non-essential amino acid, 1 mM pyruvate, 0.1 mM 2-mercaptoethanol) was used. On day 8 after the initiation of differentiation, an optic vesicle wherein the epithelial structure of retinal progenitor tissue is projected like a pouch was cut off from the cell aggregate using a No. 11 Blade and suspension cultured in a culture medium of DMEM/F12 (N2 Supplement, 10% FBS, 0.5 μM all-trans-retinoic acid, 1 mM L-taurine) under environment of 40% $O_2$ and 5% $CO_2$. Three-dimensional retina was cut off on day 15 after the initiation of differentiation and subretinally transplanted using a syringe into a rd1 mouse, a photoreceptor cell degeneration model. On the age equivalent to 30- to 50-day differentiation after transplant, the ocular tissue was fixed in paraformaldehyde (PFA fixation) and replaced with sucrose. Tissue sections were prepared using a cryostat. Rod bipolar cells, amacrine cells, and horizontal cells in the tissue section were stained by immunostaining using respectively an anti-PKCα antibody (product name: Rabbit Anti-Protein Kinase Cα antibody, manufactured by Sigma), an anti-calretinin antibody (product name: Rabbit Anti-Calretinin Antibody, manufactured by Millipore), and an anti-calbindin antibody (product name: Monoclonal Anti Calbindin-D-28K antibody, manufactured by Sigma) and the grafts after transplant were evaluated.

Fluorescence observation was performed on the stained tissue using a confocal microscope (product name: TCS SP8, manufactured by Leica) to investigate a ratio of each cell in the graft. As a result, the ratio of rod bipolar cells was found to have been significantly reduced when the retinal tissue wherein the BhIhb4 gene was deleted was transplanted compared with the case where the retinal tissue wherein the BhIhb4 gene was not deleted was transplanted (FIG. 1).

Example 2: Example of Transplanting the Retinal Tissue Derived from Mouse iPS Cells wherein the Function of a BhIhb4 Gene is Deleted to Enhance a Contact Ratio with Host Rod Bipolar Cells Mouse iPS cells having an Nr1::eGFP reporter established from an Nr1::eGFP mouse were cultured while maintaining undifferentiated state in accordance with the method described in Nature biotechnology, 26(2), 215-24, (2008).

The method for inducing differentiation into the retina and the transplant method used were the same methods as in Example 1. On the age equivalent to about 40- to 90-day differentiation after transplant, the ocular tissue was fixed in PFA and replaced with sucrose. Tissue sections were prepared using a cryostat. Rod bipolar cells in the tissue section were stained by immunostaining using an anti-PKCα antibody (product name: Rabbit Anti-Protein Kinase Cα antibody, manufactured by Sigma).

Figure 2:
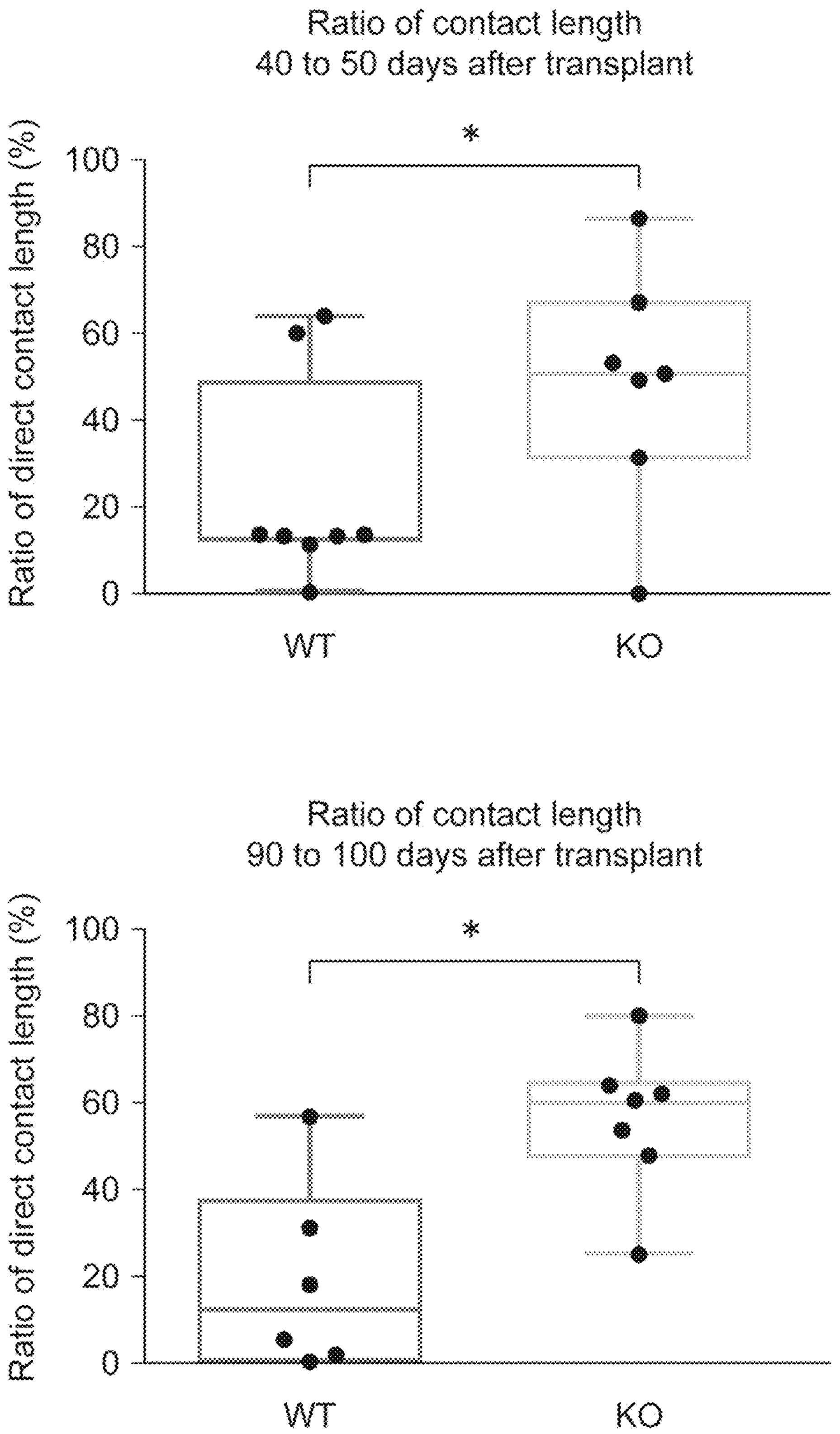
FIG. 2 is graphs showing the ratio of contact lengths of host rod bipolar cells and transplanted photoreceptor cells 40 to 50 days after or 90 to 100 days after transplant of the retinal tissue derived from mouse iPS cells wherein the function of a Bhlhb4 gene is deleted.

Fluorescence observation was performed on the stained tissue using a confocal microscope (product name: TCS SP8, manufactured by Leica) to investigate a ratio of the length of the part along which the host rod bipolar cells and the eGFP-positive transplanted photoreceptor cells were in contact with each other to the length of the entire part wherein the graft was present. As a result, the ratio of the photoreceptor cells derived from the graft in contact with the host rod bipolar cells was found to have been significantly increased when the retinal tissue wherein the BhIhb4 gene was deleted was transplanted compared with the case where the retinal tissue wherein the BhIhb4 gene was not deleted was transplanted (FIG. 2).

Example 3: Example of Transplanting the Retinal Tissue Derived from Mouse iPS Cells wherein the Function of an ISL1 Gene is Deleted to Reduce Rod Bipolar Cells, Amacrine Cells, and Horizontal Cells in the Transplanted Tissue Mouse iPS cells having an Nr1::eGFP reporter established from an Nr1::eGFP mouse were cultured while maintaining undifferentiated state in accordance with the method described in Nature biotechnology, 26(2), 215-24, (2008).

A CRISPR/Cas9 system was used as a method for deleting the function of an ISL1 gene. CRISPR/Cas9, target sequences designed so as to delete the first and second exons of the ILS1 gene (SEQ ID NO 18: tcttcaatagcacgcgggaa, SEQ ID NO 19: tcctaagccataaagcgctt), and a plasmid into which a puromycin-resistance gene was incorporated were introduced to the mouse iPS cells by electroporation (Nucreofector, manufactured by Lonza). The introduced cells were selected using puromycin and colonies were picked up, whereby an ISL1 gene-deleted line was established. The deletion at the sites of interest in the ISL1 gene was confirmed by PCR and agarose gel electrophoresis, or by reading the nucleotide sequence information.

SFEBq method described in Non Patent Literature 5, which is the modified method described in Non Patent Literature 2, was used as the method for inducing differentiation into the retina. The induction of differentiation was operated as follows. Mouse iPS cells were enzymatically treated and dispersed into single cells, and subsequently suspension cultured in a 96-well plate at 3000 cells/well. From day 0 to day 1 after the initiation of differentiation, the above cells were cultured in a culture medium to which AGN193109 (0.1 µM) was added, and subsequently up to day 8 the above cells were cultured in a culture medium to which AGN193109 (0.1 µM) and Growth Factor Reduced Matrigel (2% v/v) were added. For the culture medium, G-MEM (5% KSR, 0.1 mM non-essential amino acid, 1 mM pyruvate, 0.1 mM 2-mercaptoethanol) was used. On day 8 after the initiation of differentiation, an optic vesicle was cut off using a No. 11 Blade and suspension cultured in a culture medium of DMEM/F12 (N2 Supplement, 10% FBS, 0.5 µM all-trans-retinoic acid, 1 mM L-taurine) under environment of 40% $O_2$ and 5% $CO_2$. Three-dimensional retina was cut off on day 15 after the initiation of differentiation and subretinally transplanted using a syringe into a rd1 mouse, a photoreceptor cell degeneration model. On days 30 to 50 after transplant, the ocular tissue was fixed in PFA and replaced with sucrose. Sections were prepared using a cryostat. Rod bipolar cells, amacrine cells, and horizontal cells were stained by immunostaining using respectively an anti-PKCα antibody, an anti-calretinin antibody, and an anti-calbindin antibody and the grafts after transplant were evaluated.

Figure 3:
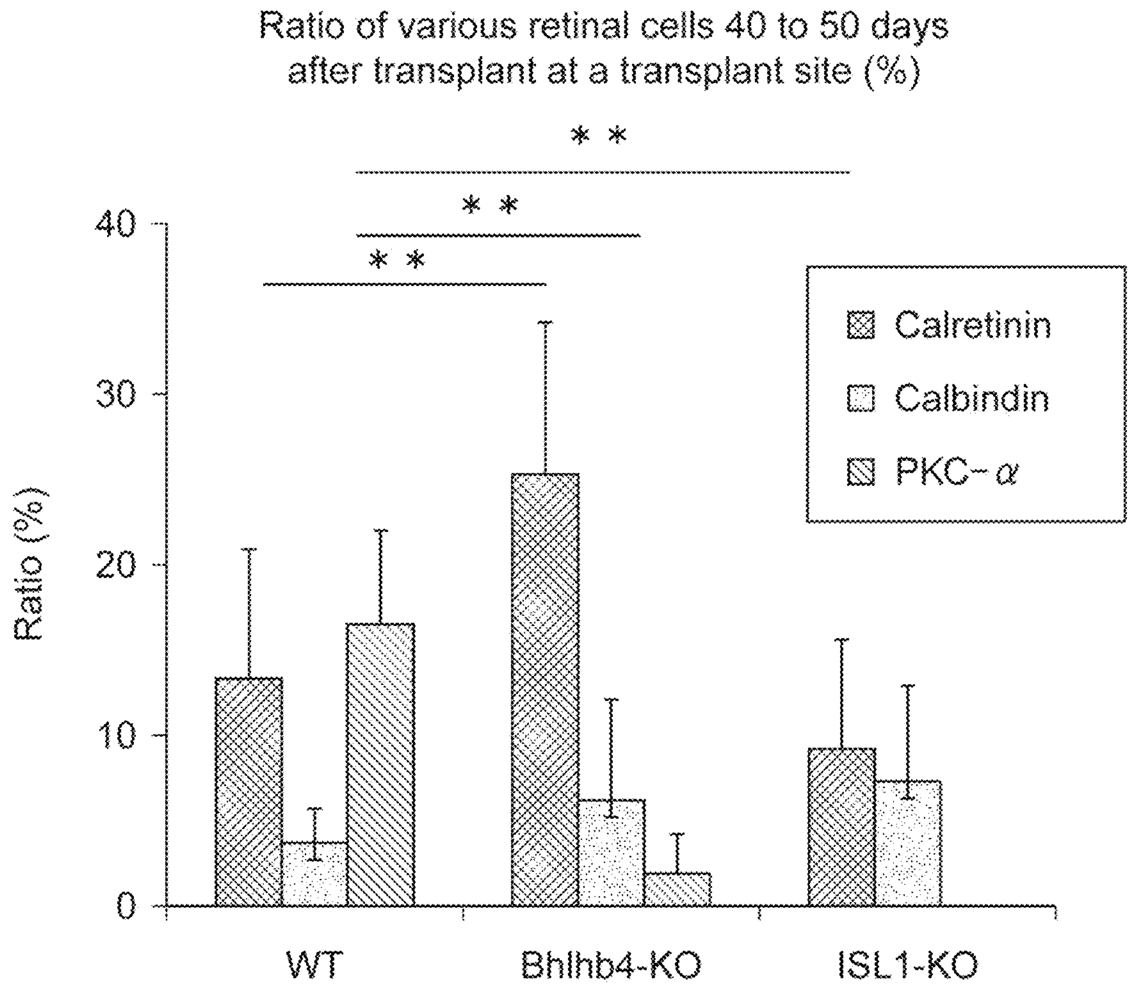
FIG. 3 is a graph showing the ratio of rod bipolar cells, amacrine cells, and horizontal cells at a transplant site 40 to 50 days after transplant of the retinal tissue derived from mouse iPS cells wherein the function of an ISL1 gene is deleted.

Fluorescence observation was performed on the stained tissue using a confocal microscope (manufactured by Leica) to investigate a ratio of each cell in the graft. As a result, the ratio of rod bipolar cells was found to have been significantly reduced when the retinal tissue wherein the ISL1 gene was deleted was transplanted compared with the case where the retinal tissue wherein the ISL1 gene was not deleted was transplanted (FIG. 3).

Example 4: Example of Transplanting the Retinal Tissue Derived from Mouse iPS Cells wherein the Function of a Bipolar Cell-Regulating Gene is Deleted and Suggesting the Synaptic Connection between the Host Bipolar Cells and the Transplanted Photoreceptor Cells in the Transplanted Tissue Mouse iPS cells having an Nr1::eGFP reporter established from an Nr1::eGFP mouse were cultured while maintaining undifferentiated state in accordance with the method described in Nature biotechnology, 26(2), 215-24, (2008).

The method for deleting the BhIhb4 gene or the ISL1 gene used was the same method as in Examples 1 and 3.

SFEBq method described in Non Patent Literature 5, which is the modified method described in Non Patent Literature 2, was used as the method for inducing differentiation into the retina. The induction of differentiation was operated as follows. Mouse iPS cells were enzymatically treated and dispersed into single cells, and subsequently suspension cultured in a 96-well plate at 3000 cells/well. From day 0 to day 1 after the initiation of differentiation, the above cells were cultured in a culture medium to which AGN193109 (0.1 µM) was added, and subsequently up to day 8 the above cells were cultured in a culture medium to which AGN193109 (0.1 µM) and Growth Factor Reduced Matrigel (2% v/v) were added. For the culture medium, G-MEM (5% KSR, 0.1 mM non-essential amino acid, 1 mM pyruvate, 0.1 mM 2-mercaptoethanol) was used. On day 8 after the initiation of differentiation, an optic vesicle was cut off using a No. 11 Blade and suspension cultured in a culture medium of DMEM/F12 (N2 Supplement, 10% FBS, 0.5 µM all-trans-retinoic acid, 1 mM L-taurine) under environment of 40% $O_2$ and 5% $CO_2$. Three-dimensional retina was cut off on day 15 after the initiation of differentiation and subretinally transplanted using a syringe into a rd1 mouse, a photoreceptor cell degeneration model. On days 30 to 50 after transplant, the ocular tissue was fixed in PFA and replaced with sucrose. Sections were prepared using a cryostat. Synaptic terminals of the rod bipolar cells and the photoreceptor cells in the section were stained by immunostaining using respectively an anti-PKCα antibody and an anti-Ctbp2 antibody and the grafts after transplant were evaluated.

Figure 4:
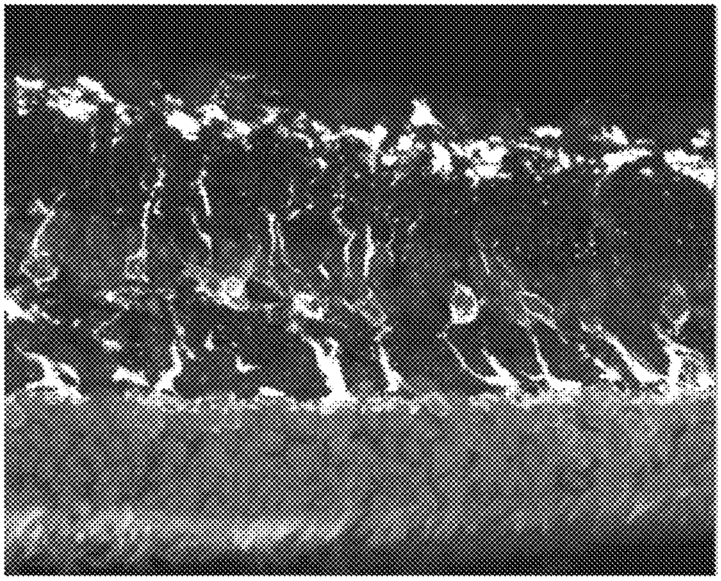
FIG. 4 is photographs showing synaptic connection between the host bipolar cells and the transplanted photoreceptor cells at a transplant site on day 30 to day 50 from transplant of the retinal tissue derived from mouse iPS cells wherein the function of a Bhlhb4 gene or an ISL1 gene is deleted.
Figure 4:
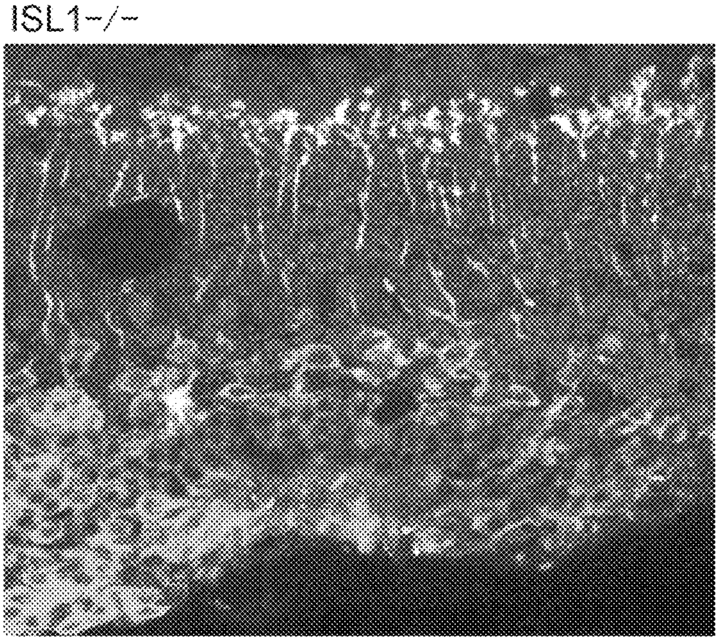

Fluorescence observation was performed on the stained tissue using a confocal microscope (manufactured by Leica) to evaluate the synaptic connection between the host bipolar cells and the transplanted photoreceptor cells in the transplanted tissue. As a result, the retinal tissue wherein the BhlhB4 and ISL1 genes were deleted, when transplanted, was suggested to have been synaptically connected with the host bipolar cells (FIG. 4).

Example 5: Example of Evaluating the Reduction of Rod Bipolar Cells, Amacrine Cells, and Horizontal Cells Due to Loss of Function of a Bipolar Cell-Regulating Gene Mouse iPS cells having an Nr1::eGFP reporter established from an Nr1::eGFP mouse were cultured while maintaining undifferentiated state in accordance with the method described in Nature biotechnology, 26(2), 215-24, (2008).

The method for deleting the BhIhb4 gene or the ISL1 gene used was the same method as in Examples 1 and 3.

SFEBq method described in Non Patent Literature 5, which is the modified method described in Non Patent Literature 2, was used as the method for inducing differentiation into the retina. The induction of differentiation was operated as follows. Mouse iPS cells were enzymatically treated and dispersed into single cells, and subsequently suspension cultured in a 96-well plate at 3000 cells/well. From day 0 to day 1 after the initiation of differentiation, the above cells were cultured in a culture medium to which AGN193109 (0.1 µM) was added, and subsequently up to day 8 the above cells were cultured in a culture medium to which AGN193109 (0.1 µM) and Growth Factor Reduced Matrigel (2% v/v) were added. For the culture medium, G-MEM (5% KSR, 0.1 mM non-essential amino acid, 1 mM pyruvate, 0.1 mM 2-mercaptoethanol) was used. On day 8 after the initiation of differentiation, an optic vesicle was cut off using a No. 11 Blade and suspension cultured in a culture medium of DMEM/F12 (N2 Supplement, 10% FBS, 0.5 µM all-trans-retinoic acid, 1 mM L-taurine) under environment of 40% $O_2$ and 5% $CO_2$. On day 29 after the initiation of differentiation, the tissue was fixed in PFA and replaced with sucrose to prepare a section. Mature photoreceptor cells using an anti-rhodopsin antibody (manufactured by Sigma), rod bipolar cells using an anti-PKCα antibody (manufactured by Sigma), amacrine cells, horizontal cells, and bipolar cells using an anti-ISL1 antibody (product name: Anti Islet 1 Antibody, manufactured by DSHB), photoreceptor cells using an anti-Recoverin antibody (product name: Anti Recoverin Antibody, manufactured by Millipore), bipolar cells using an anti-Chx10 antibody (product name: Anti Chx10 Antibody, manufactured by Exalpha), and Muller glial cells using an anti-GS antibody (product name: Anti GS Antibody, manufactured by Millipore) and an anti-GFAP antibody (product name: Anti GFAP antibody, manufactured by dako) were stained by immunostaining, and fluorescence observation was performed using a confocal microscope (TCS, SP8, manufactured by Leica).

Figure 5:
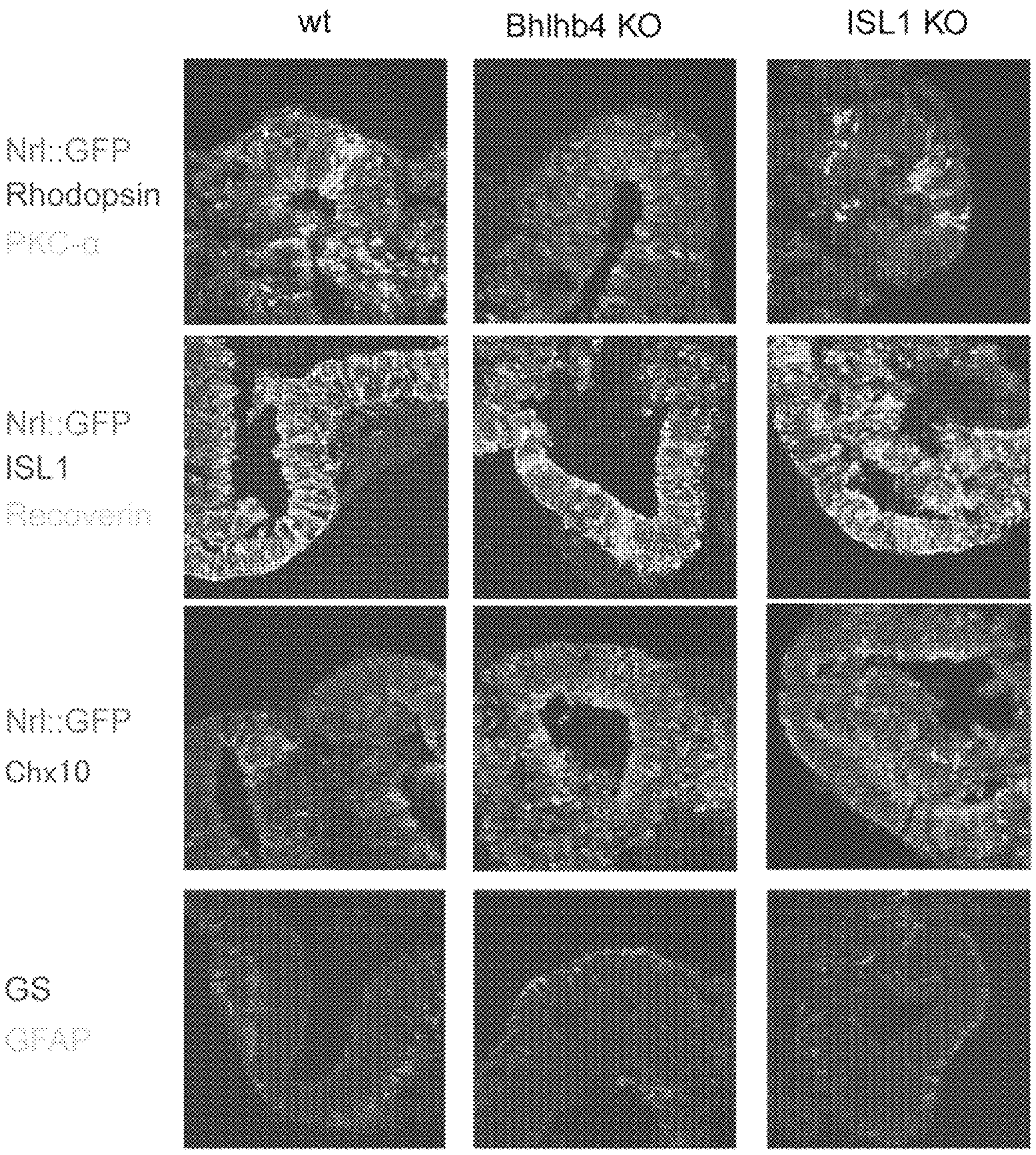
FIG. 5 is confocal microscope photographs of the immunostained retinal tissue (tissue on day 29 after the initiation of differentiation) derived from mouse iPS cells wherein the function of a Bhlhb4 gene or an ISL1 gene is deleted.

Fluorescence observation was performed on the stained tissue using a confocal microscope (manufactured by Leica) and a ratio of each cell in the differentiation-induced retinal tissue was investigated. As a result, the aggregate (aggregate cluster) derived from iPS cells wherein the BhIhb4 gene or the ISL1 gene was deleted had Nr1-positive rod photoreceptor cells, rhodopsin-positive mature photoreceptor cells, Recoverin-positive photoreceptor cells, and GS-positive and GFAP-positive Muller glial cells just as the aggregate wherein the BhIhb4 gene and the ISL1 gene were not deleted. On the other hand, PKCα-positive rod bipolar cells, Chx10-positive bipolar cells, and ISL1-positive cells were reduced (FIG. 5). Thus, it was found that when iPS cells wherein the BhlhB4 gene or the ISL1 gene was deleted were cultured for long term under conditions of differentiating into the retinal cells, the number of photoreceptor cells and Muller glia cells was I5 not affected while the number of bipolar cells and ISL 1-positive cells decreased significantly (FIG. 5).

Example 6: Example of Establishing a Human ES Cell Line wherein the Function of an ISL1 Gene is Deleted Human ES cells (Kh-ES1 line, Non Patent Literature 3) genetically modified so as to have a Crx::Venus reporter gene were cultured under feeder free conditions in accordance with the method described in "Scientific Reports, 4, 3594 (2014)". StemFit medium (product name: AK03N, manufactured by Ajinomoto Co., Inc.) was used as the feeder free culture medium and Laminin511-E8 (product name, manufactured by Nippi Inc.) was used as a scaffold in place of the feeder cells.

Maintenance culture of the human ES cells was operated specifically as follows. Human ES cells (KhES-1 line) reached subconfluence (about 60% of a culture area is covered with cells) was washed with PBS and dispersed into single cells using TrypLE Select (product name, manufactured by Life Technologies). Subsequently, the human ES cells dispersed into single cells were inoculated in a plastic culture dish coated with Laminin511-E8 and cultured in the presence of Y27632 (ROCK inhibitor, 10 μM) under feeder free conditions in StemFit medium. When a 6-well plate (manufactured by IWAKI & CO., LTD., for cell culture, culture area 9.4 $cm^2$) was used as the plastic culture dish, the inoculated number of the above human ES cells dispersed into single cells was $1.2\times10^4$ cells/well. One day after inoculation, the medium was replaced with Y27632 free StemFit medium. Thereafter, the medium was replaced with Y27632 free StemFit medium once every 1 to 2 days. Subsequently, 6 days after inoculation, the cells were cultured until subconfluency was reached.

The following operation was performed as an introduction example of a CRISPR/Cas9 system in step (1) of a method for producing a cell population for transplant comprising retinal cells. Human ES cells which reached subconfluence were washed with PBS, dispersed into single cells using TrypLE Select, and collected. Subsequently, CRISPR/Cas9, gRNA designed so as to delete the first and second exons of the ISL1 gene (SEQ ID NO 20: CCAACTCCGCCGGCTTAAAT, SEQ ID NO 21: GGGAGGTTAATACTTCGGAG), and a plasmid into which a puromycin-resistance gene was incorporated were introduced to the human ES cells using electroporation (product name: Nucreofector, manufactured by Lonza).

Figure 6A:
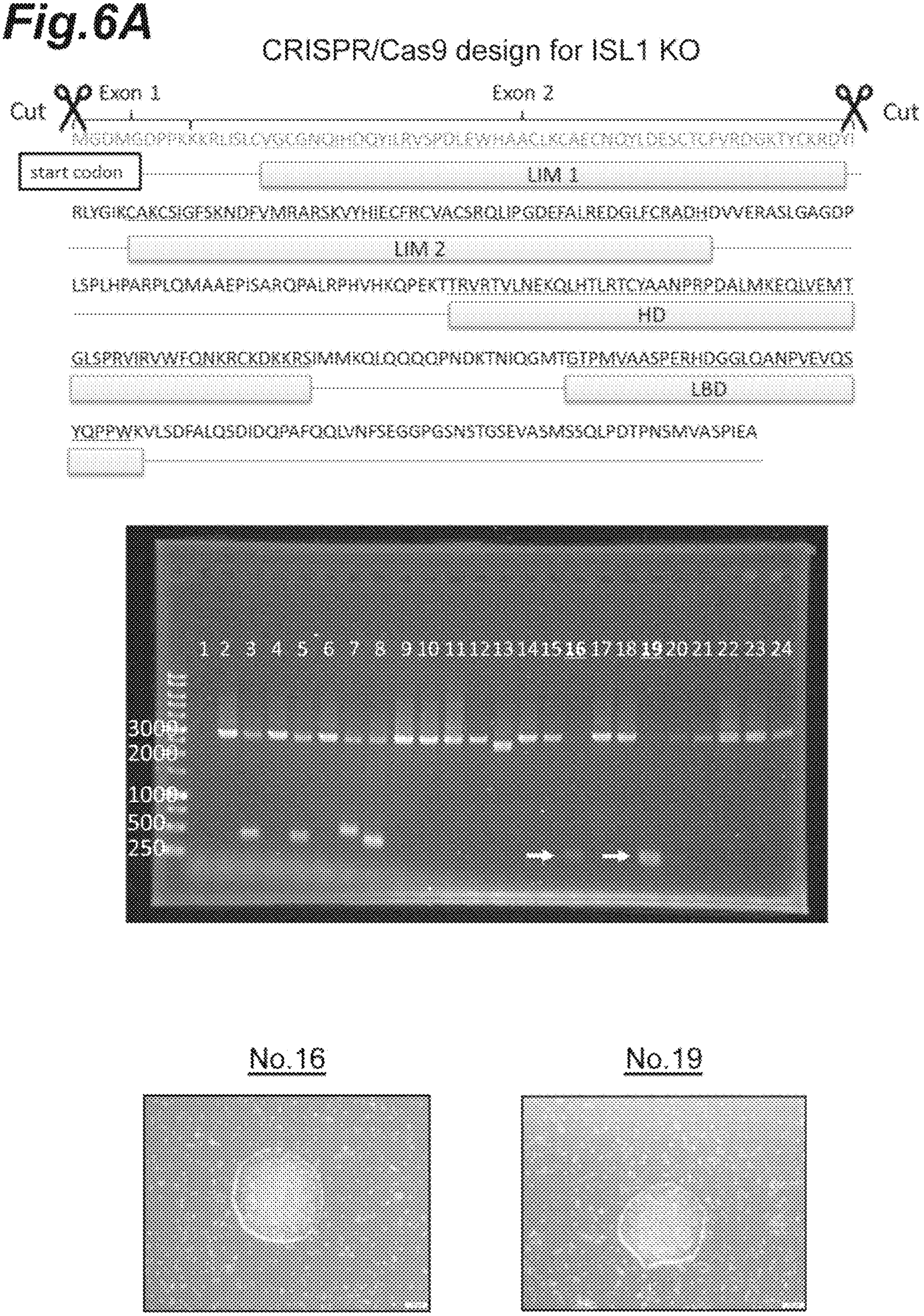
FIG. 6A is (upper row) a schematic diagram showing the design of CRISPR/Cas9 system for deleting the function of an ISL1 gene (SEQ ID NO: 3), (middle row) an agarose gel electrophoresis photograph for confirming the deletion of the ISL1 gene, and (lower row) a photograph of an established human ES cell line (ISL1 gene-deleted line).

The human ES cells into which the plasmid was introduced by electroporation were inoculated in a plastic culture dish (manufactured by IWAKI & CO., LTD.) coated with Laminin511-E8 and cultured in the presence of Y27632 (ROCK inhibitor, 10 μM) under feeder free conditions in StemFit medium. When a 6-well plate (manufactured by IWAKI & CO., LTD., culture area 9.4 $cm^2$) was used as the plastic culture dish, the inoculated number of the above human ES cells dispersed into single cells was $1\times10^3$ cells/well. One day after inoculation, the medium was replaced with Y27632 free StemFit medium. Thereafter, the medium was replaced with Y27632 free StemFit medium once every 1 to 2 days. Thereafter, the cells were cultured until 6 days after inoculation or until 1 day before reaching subconfluence. 0.5 ng/ml or 0.4 ng/ml of puromycin was added to the human ES cells of 1 day before reaching subconfluence cultured under the above feeder free conditions, and the plasmid-introduced cells were selected. The colonies survived by selection were picked up and genetically analyzed to establish ISL1 gene-deleted lines (No. 16 line and No. 19 line, lower row in FIG. 6A). At the time of picking up the colonies, the cells were dispersed into single cells using TrypLE Select and subsequently a half thereof was inoculated in a plastic culture dish (manufactured by IWAKI & CO., LTD.,) coated with Laminin511-E8 and cultured in the presence of Y27632 (10 μM) under feeder free conditions in StemFit medium. The other half was collected as a genetic analysis sample.

Figure 6B:
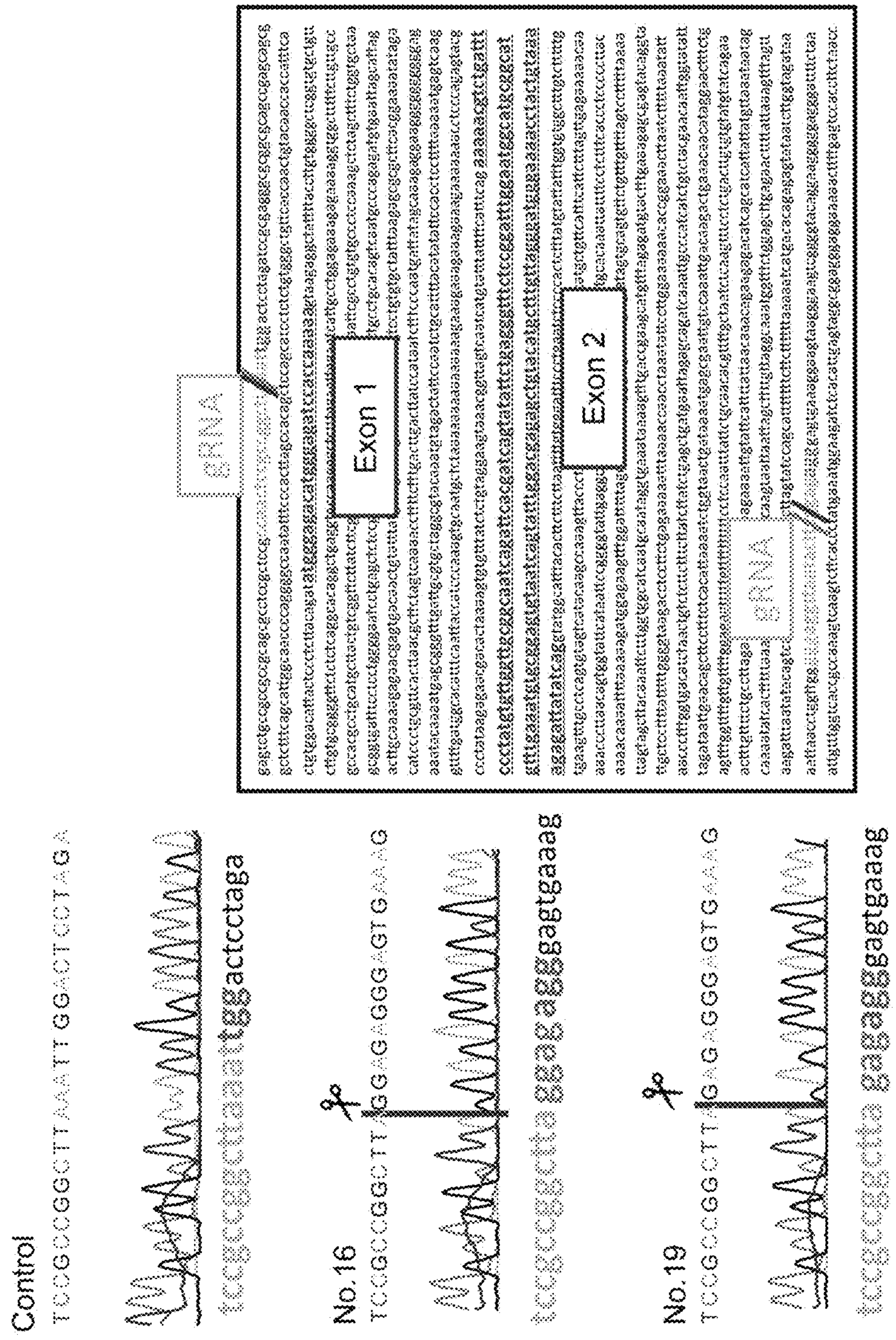
FIG. 6B is drawings showing the sites of the ISL1 gene cleaved by the CRISPR/Cas9 system. Control sequence is SEQ ID NO: 22, No. 16 sequence is SEQ ID NO: 23, No. 19 sequence is SEQ ID NO: 24, gRNA sequence is SEQ ID NO: 20 and 21.

The deletion at the sites of interest in the ISL1 gene of the human ES cells in the colonies picked up was confirmed by PCR and agarose gel electrophoresis (middle row in FIG. 6A) and by investigating the nucleotide sequence information (FIG. 6B).

Example 7: Example of Differentiating the Human ES Cell Line wherein the Function of an ISL1 Gene is Deleted into the Retina The ISL1 gene-deleted human ES cells (KhES-1 line derived, No. 16 line and No. 19 line) prepared in Example 6 were cultured in StemFit medium under feeder free conditions until 1 day before reaching subconfluence. The human ES cells of 1 day before reaching subconfluence were cultured for 1 day in the presence of SB431542 (TGFβ signaling pathway agent, 5 μM) and SAG (Shh signaling pathway agent, 300 nM) (Precondition treatment) under feeder free conditions.

The ISL1 gene-deleted human ES cells prepared in Example 6 were washed with PBS, subsequently treated with a cell dispersion using TrypLE Select, further dispersed into single cells by pipetting procedure, and subsequently the human ES cells dispersed into single cells were suspended in 100 μL of a serum-free culture medium so as to be $1.2\times10^4$ cells per well of a non-cell adhesive 96-well culture plate (product name: PrimeSurface 96-well V-bottom plate, manufactured by Sumitomo Bakelite Co., Ltd.) and suspension cultured at 27° C., 5% $CO_2$. For the serum-free culture medium (gfCDM+KSR) at this operation, a serum-free culture medium wherein 10% KSR, 450 μM of 1-monothioglycerol, and 1× Chemically defined lipid concentrate were added to a 1:1 mixed solution of F-12 medium and IMDM medium was used.

At the initiation of suspension culture (day 0 after the initiation of suspension culture), Y27632 (ROCK inhibitor, final concentration 20 μM) and SAG (Shh signaling pathway agent, 300 nM or 30 nM) were added to the above serum-free culture medium. On day 3 after the initiation of suspension culture, 50 μL of a culture medium comprising exogenous recombinant human BMP4 (product name: Recombinant Human BMP-4, manufactured by R&D) at a final concentration of 1.5 nM and not comprising Y27632 and SAG was added.

Figure 7A:
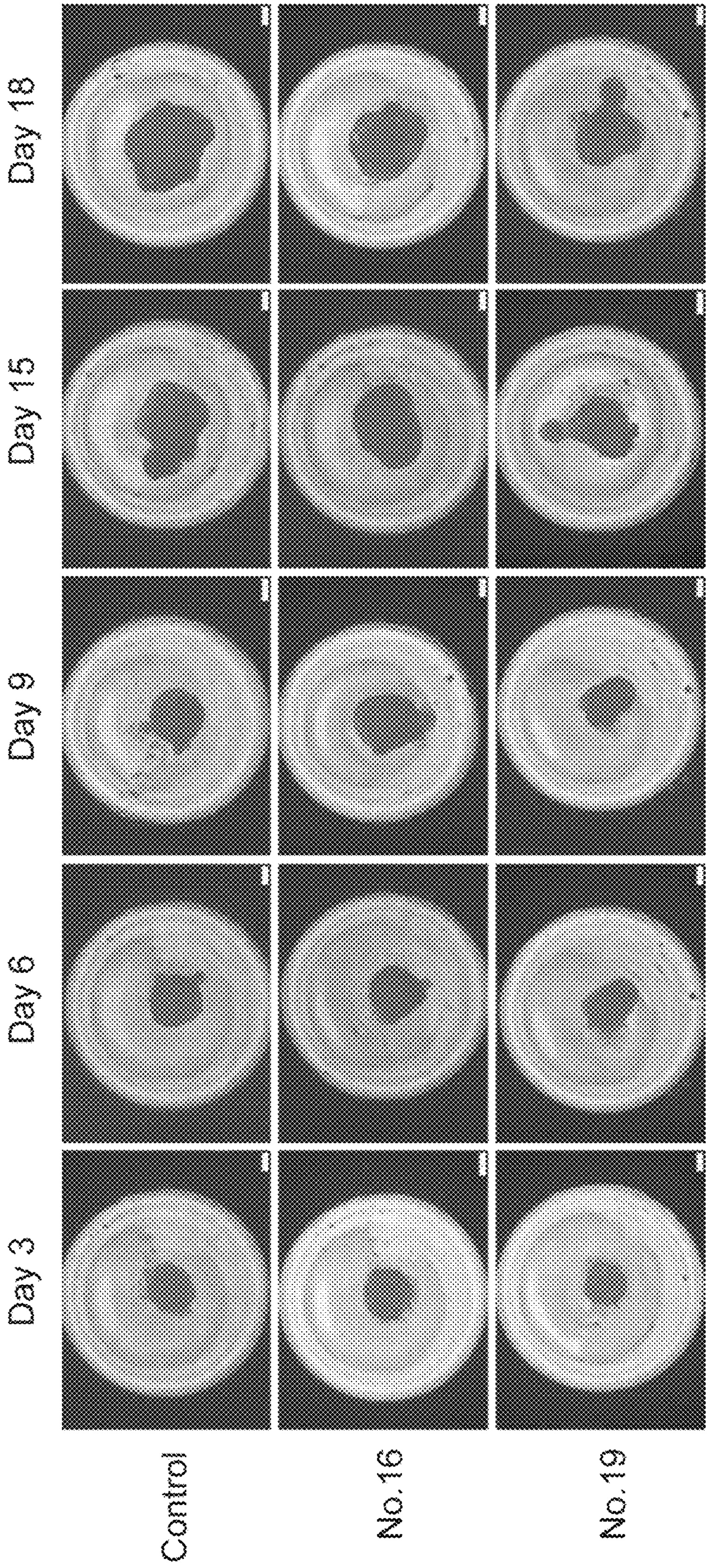
FIG. 7A is photographs showing that the human ES cell line wherein the function of the ISL1 gene is deleted is differentiated into a retina.

Bright-field observation was performed on the thus prepared cells on days 3, 6, 9, 15, and 18 after the initiation of suspension culture using an inverted microscope (FIG. 7A). As a result, it was revealed that cell aggregates having a stratified structure were formed also in the human ES cell lines wherein the function of the ISL1 gene was deleted (FIG. 7A).

Figure 7B:
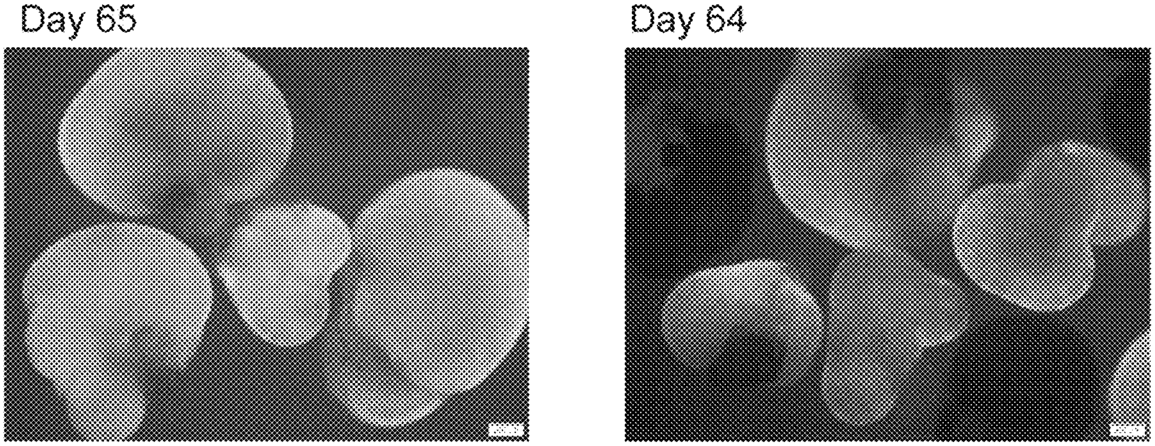
FIG. 7B is photographs showing the presence of photoreceptor precursor cells in the retina derived from the human ES cell line wherein the function of the ISL1 gene is deleted.

The aggregate on day 18 after the initiation of suspension culture was moved to a 90 mm low-adhesion culture dish (manufactured by Sumitomo Bakelite Co., Ltd.) and cultured in a serum-free culture medium comprising Wnt signaling pathway agent (CHIR99021, 3 μM) and FGF signaling pathway agent (SU5402, 5 μM) (a culture medium wherein 1% N2 Supplement was added to DMEM/F12 medium) at 37° C., 5% $CO_2$ for 3 to 4 days. Subsequently, the aggregate was long-term cultured in a 90 mm low-adhesion culture dish (manufactured by Sumitomo Bakelite Co., Ltd.) in a serum culture medium not comprising Wnt signaling pathway agent and FGF signaling pathway agent (a culture medium wherein 10% fetal bovine serum, 1% N2 Supplement, 0.5 μM retinoic acid, and 100 μM taurine were added to DMEM/F12 medium). Half medium replacement was performed once in 2 to 4 days with the above serum culture medium. The cells were observed on days 64 to 65 after the initiation of suspension culture using a fluorescence microscope (FIG. 7B). As a result, it was revealed that three-dimensional retina having CRX-positive photoreceptor precursor cells was formed in the human ES cell line wherein the function of the ISL1 gene was deleted (FIG. 7B).

Figure 7C:
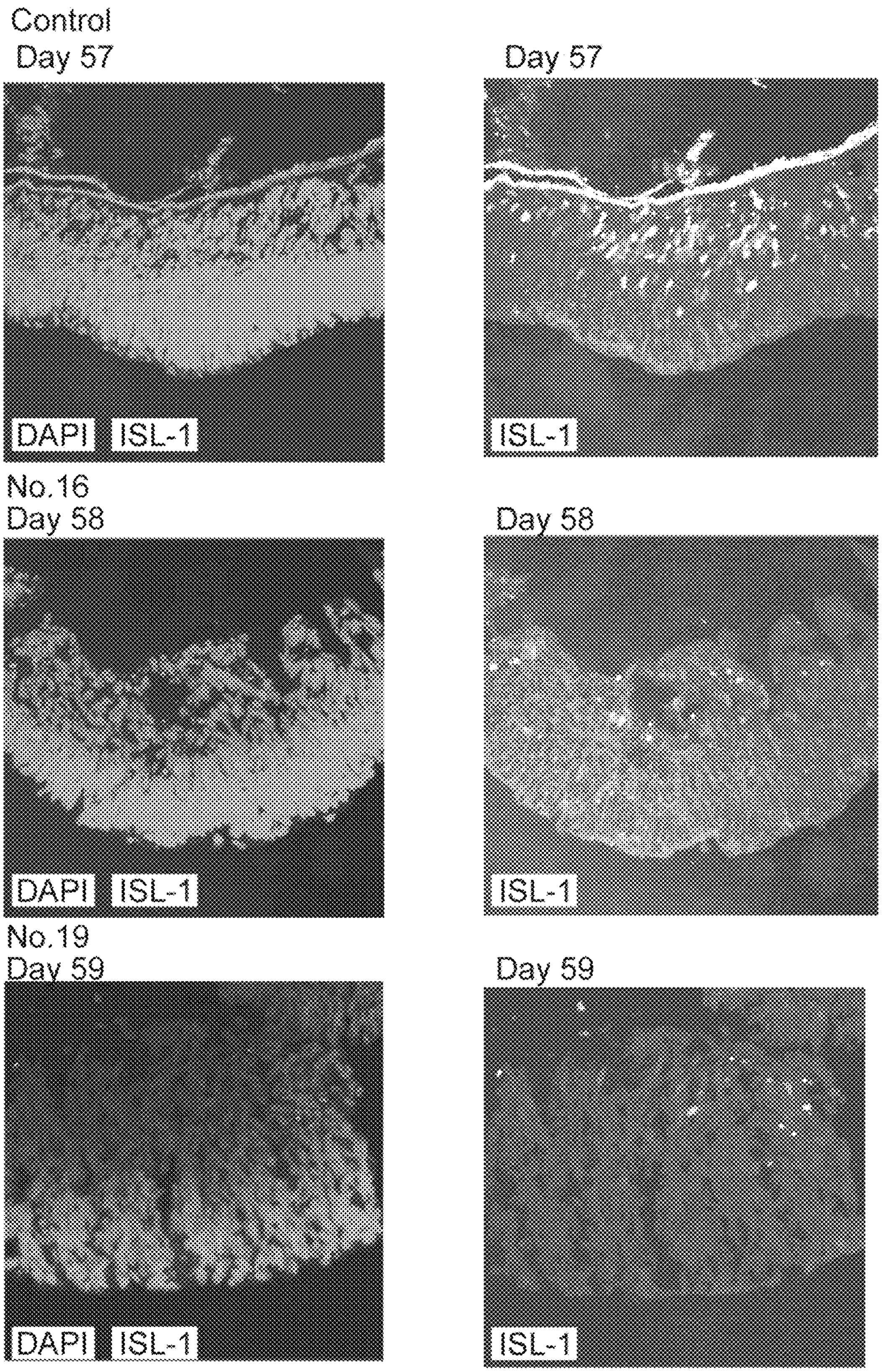
FIG. 7C is photographs showing that the ISL1 protein is not expressed in the retina derived from the human ES cell line wherein the function of the ISL1 gene is deleted.

Cell aggregates on days 57, 58, and 59 after the initiation of suspension culture prepared using the human ES cells wherein the ISL1 gene was deleted as a starting material was fixed in 4% PFA to prepare frozen sections. These frozen sections were immunostained using an anti-ISL1 antibody (product name: Anti Islet-1 Antibody, manufactured by DSHB). These immunostained sections were observed using a confocal fluorescence microscope. As a result, it was revealed that ISL1 protein was not expressed in the cell aggregates prepared from the human ES cells wherein the ISL1 gene was deleted (FIG. 7C).

These results revealed that retinal tissue can be formed from the human ES cell lines wherein the ISL1 gene has the failed function and that ISL1 protein is not expressed in the human ES cell line wherein the ISL1 gene has the failed function.

Example 8: Example of Transplanting the Retina into which the Human ES Cell Line wherein the Function of an ISL1 Gene is Deleted is Differentiated and Confirming the Integration thereof The ISL1 gene-deleted human ES cells (KhES-1 line derived) prepared in Example 6 were cultured in StemFit medium under feeder free conditions until 1 day before reaching subconfluence. The human ES cells of 1 day before reaching subconfluence were cultured for 1 day in the presence of SB431542 (TGFβ signaling pathway agent, 5 μM) and SAG (Shh signaling pathway agent, 300 nM) (Precondition treatment) under feeder free conditions.

The ISL1 gene-deleted human ES cells prepared in Example 6 were washed with PBS, subsequently treated for dispersion using TrypLE Select, further dispersed into single cells by pipetting procedure, and subsequently the human ES cells dispersed into single cells were suspended in 100 μL of a serum-free culture medium so as to be $1.2\times10^4$ cells per well of a non-cell adhesive 96-well culture plate (product name: PrimeSurface 96-well V-bottom plate, manufactured by Sumitomo Bakelite Co., Ltd.) and suspension cultured at 37° C., 5% $CO_2$. For the serum-free culture medium (gfCDM+KSR) at this operation, a serum-free culture medium wherein 10% KSR, 450 μM of 1-monothioglycerol, and 1× Chemically defined lipid concentrate were added to a 1:1 mixed solution of F-12 medium and IMDM medium was used.

At the initiation of suspension culture (day 0 after the initiation of suspension culture), Y27632 (final concentration 20 μM) and SAG (Shh signaling pathway agent, 300 nM or 30 nM) were added to the above serum-free culture medium. On day 3 after the initiation of suspension culture, 50 μL of a culture medium comprising recombinant human BMP4 (product name: Recombinant Human BMP-4, manufactured by R&D, final concentration 1.5 nM) and not comprising Y27632 and SAG was added.

On day 6 after the initiation of suspension culture of the thus prepared cells, 60 μL of the culture medium was removed and 90 μL of a fresh culture medium was added. Further, on days 9, 12 and 15 after the initiation of suspension culture, 85 μL of the culture medium was removed and 90 μL of a fresh culture medium was added.

Figure 8:
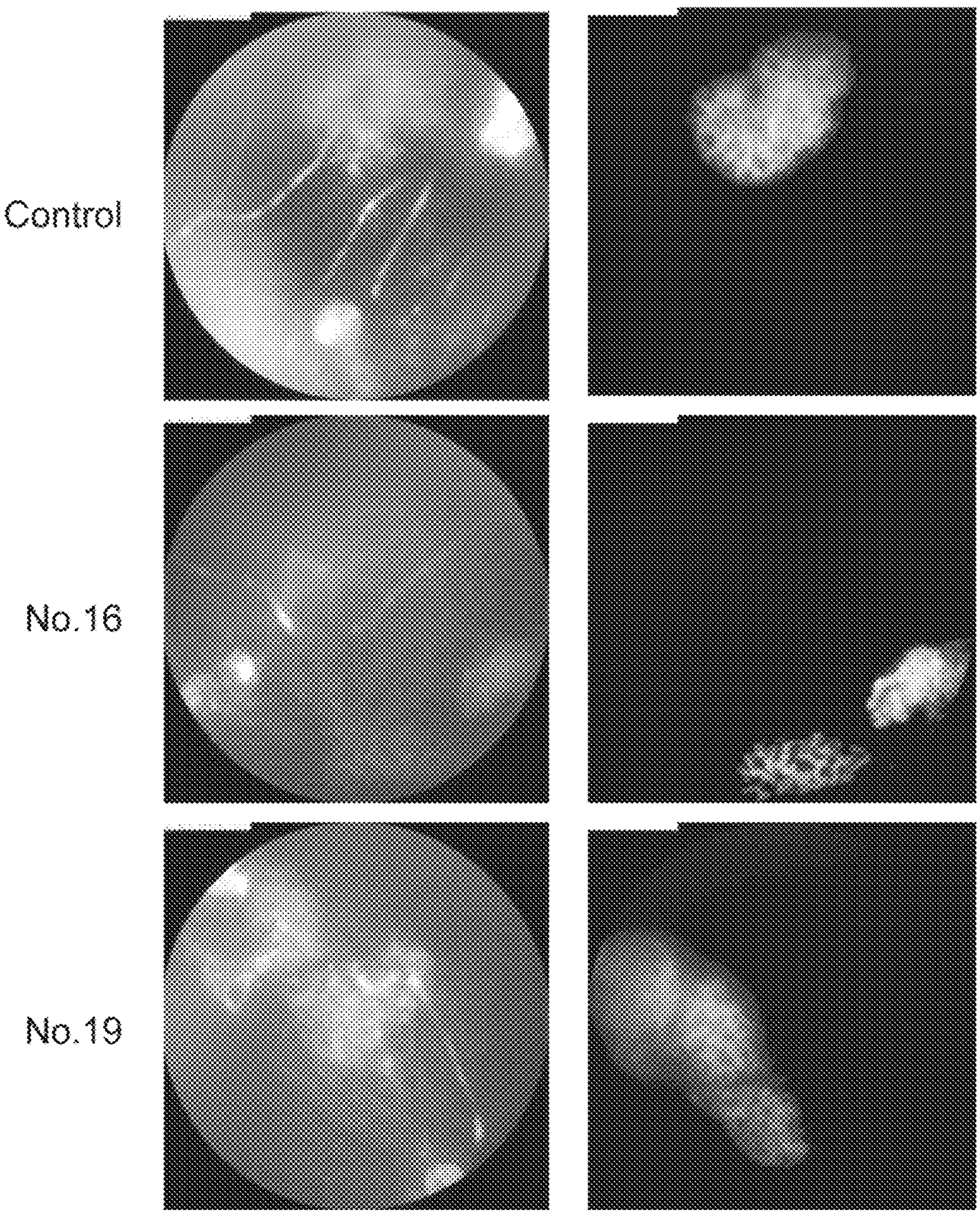
FIG. 8 is photographs showing that the retina derived from the human ES cell line wherein the function of the ISL1 gene is deleted has been integrated after transplanted into a retinal degeneration rat.

The aggregate on day 18 after the initiation of suspension culture was moved to a 90 mm low-adhesion culture dish (manufactured by Sumitomo Bakelite Co., Ltd.) and cultured in a serum-free culture medium comprising Wnt signaling pathway agent (CHIR99021, 3 μM) and FGF signaling pathway agent (SU5402, 5 μM) (a culture medium wherein 1% N2 Supplement was added to DMEM/F12 medium) at 37° C., 5% $CO_2$ for 3 to 4 days. Subsequently, the aggregate was long-term cultured in a 90 mm low-adhesion culture dish (manufactured by Sumitomo Bakelite Co., Ltd.) in a serum culture medium not comprising Wnt signaling pathway agent and FGF signaling pathway agent (a culture medium wherein 10% fetal bovine serum, 1% N2 Supplement, 0.5 μM retinoic acid, and 100 μM taurine were added to DMEM/F12 medium). Half medium replacement was performed once in 2 to 4 days with the above serum culture medium. Three-dimensional retina was cut off on days 58 to 65 after the initiation of suspension culture and subretinally transplanted using a syringe into a retinal degeneration rat, a photoreceptor cell degeneration model. On months 1 to 2 after transplant, the integration of a graft was observed based on the fluorescence of CRX::Venus using a fluorescent funduscopy (product name: MicronIV, manufactured by Phoenix research). As a result, the retinal tissue wherein the ISL1 gene was deleted, when transplanted, was subretinally integrated into the retinal degeneration rat as comparable as the retinal tissue wherein the ISL1 gene was not deleted (FIG. 8). Thus, it was revealed that the retinal tissue into which the human ES cells wherein the ISL1 gene is deleted are differentiated is integrated after transplant.

Example 9: Example of Transplanting the Retina into which the Human ES Cell Line wherein the Function of the ISL1 Gene is Deleted is Differentiated and Confirming the Reduction in Ratio of Bipolar Cells The ISL1 gene-deleted human ES cells (KhES-1 line derived) prepared in Example 6 were cultured in StemFit medium under feeder free conditions until 1 day before reaching subconfluence. The human ES cells of 1 day before reaching subconfluence were cultured for 1 day in the presence of SB431542 (TGFβ signaling pathway agent, 5 μM) and SAG (Shh signaling pathway agent, 300 nM) (Precondition treatment) under feeder free conditions.

The ISL1 gene-deleted human ES cells cultured above were washed with PBS, subsequently treated for dispersion using TrypLE Select, further dispersed into single cells by pipetting procedure, and subsequently the human ES cells dispersed into single cells were suspended in 100 μL of a serum-free culture medium so as to be $1.2\times10^4$ cells per well of a non-cell adhesive 96-well culture plate (product name: PrimeSurface 96-well V-bottom plate, manufactured by Sumitomo Bakelite Co., Ltd.) and suspension cultured at 37° C., 5% $CO_2$. For the serum-free culture medium (gfCDM+KSR) at this operation, a serum-free culture medium wherein 10% KSR, 450 μM of 1-monothioglycerol, and 1× Chemically defined lipid concentrate were added to a 1:1 mixed solution of F-12 medium and IMDM medium was used.

At the initiation of suspension culture (day 0 after the initiation of suspension culture), Y27632 (final concentration 20 μM) and SAG (Shh signaling pathway agent, 300 nM or 30 nM) were added to the above serum-free culture medium. On day 3 after the initiation of suspension culture, 50 μL of a culture medium comprising recombinant human BMP4 (product name: Recombinant Human BMP-4, manufactured by R&D, final concentration 1.5 nM) and not comprising Y27632 and SAG was added.

On day 6 after the initiation of suspension culture of the thus prepared cells, 60 μL of the culture medium was removed and 90 μL of a fresh culture medium was added. Further, on days 9, 12 and 15 after the initiation of suspension culture, 85 μL of the culture medium was removed and 90 μL of a fresh culture medium was added.

The aggregate on day 18 after the initiation of suspension culture was moved to a 90 mm low-adhesion culture dish (manufactured by Sumitomo Bakelite Co., Ltd.) and cultured in a serum-free culture medium comprising Wnt signaling pathway agent (CHIR99021, 3 μM) and FGF signaling pathway agent (SU5402, 5 μM) (a culture medium wherein 1% N2 Supplement was added to DMEM/F12 medium) at 37° C., 5% $CO_2$ for 3 to 4 days. Subsequently, the aggregate was long-term cultured in a 90 mm low-adhesion culture dish (manufactured by Sumitomo Bakelite Co., Ltd.) in a serum culture medium not comprising Wnt signaling pathway agent and FGF signaling pathway agent (a culture medium wherein 10% fetal bovine serum, 1% N2 Supplement, 0.5 μM retinoic acid, and 100 μM taurine were added to DMEM/F12 medium). Half medium replacement was performed once in 2 to 4 days with the above serum culture medium. The obtained three-dimensional retina was cut off on days 58 to 65 after the initiation of suspension culture and subretinally transplanted using a syringe into a retinal degeneration rat, a photoreceptor cell degeneration model. On the age equivalent to 240- to 270-day differentiation after transplant, the ocular tissue was fixed in PFA and replaced with sucrose. Tissue sections were prepared using a cryostat. Human cells, bipolar cells, and amacrine cells in the tissue section were stained by immunostaining using respectively an anti-Nuclei antibody (product name: Anti-Nuclei, manufactured by Millipore), an anti-Chx10 antibody (product name: Chx10 Anti Antibody, manufactured by EX alpha), and an anti-Pax6 antibody (product name: Anti Pax6 antibody, manufactured by Covance Inc.) and the grafts after transplant were evaluated. Three slides each of the retinal tissue wherein the Islet-1 gene was not deleted (wild type) and the retinal tissue wherein the Islet-1 gene was deleted were stained and 2 areas were photographed per slide.

Figure 9A:
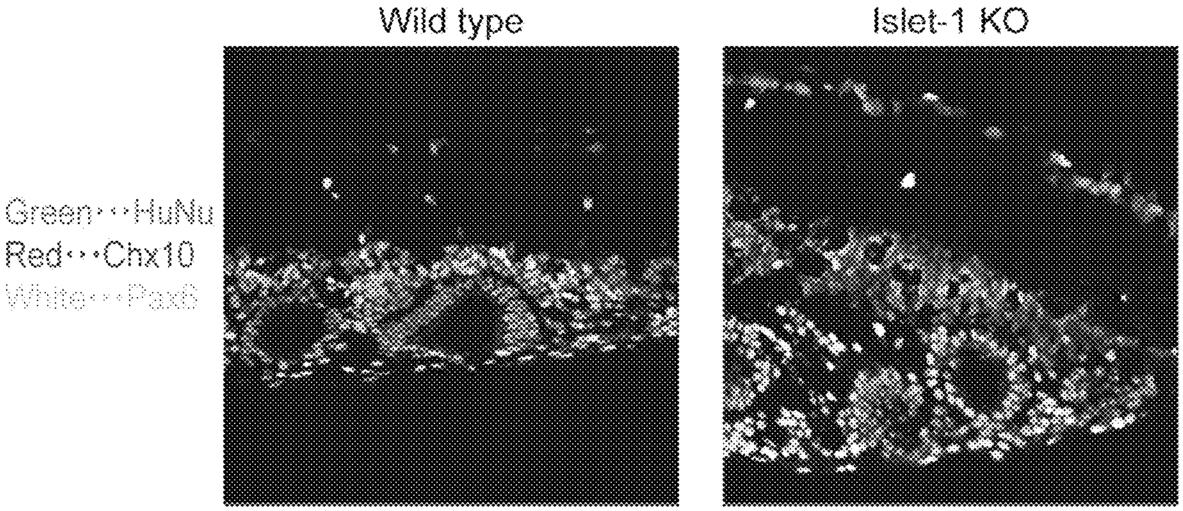
FIG. 9A is photographs showing the ratio of bipolar cells and amacrine cells at a transplant site 240 to 260 days after transplant of the retina into which the human ES cell line wherein the function of the ISL1 gene is deleted is differentiated.
Figure 9B:
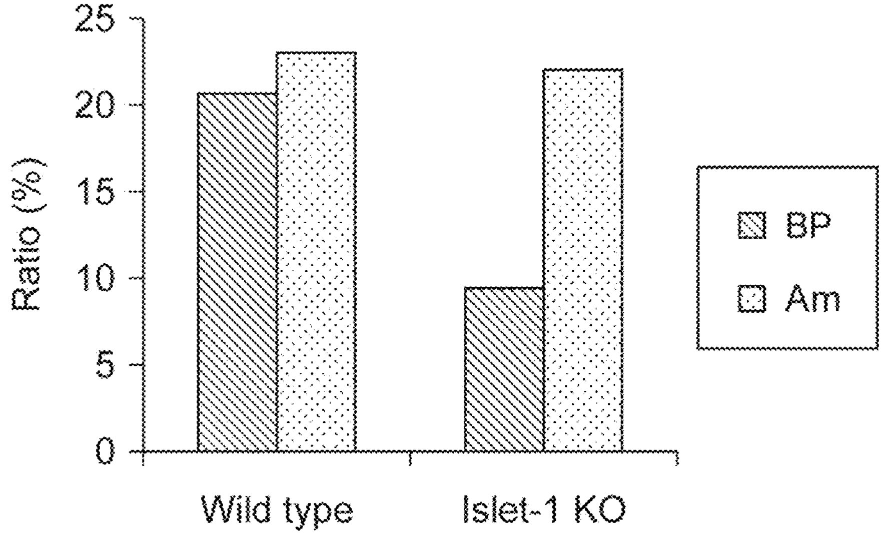
FIG. 9B is a graph showing the ratio of bipolar cells and amacrine cells at a transplant site 240 to 260 days after transplant of the retina into which the human ES cell line wherein the function of the ISL1 gene is deleted is differentiated.

Fluorescence observation was performed on the stained tissue using a confocal microscope (product name: TCS SP8, manufactured by Leica) and ratio of the bipolar cells and the amacrine cells derived from the human cells in the grafts were investigated in 3 sections at 2 areas. Representative photographs thereof are shown in FIG. 9A. From FIG. 9A, it was confirmed that the ratio of the Chx10-positive cells (i.e., bipolar cells) was reduced when the retinal tissue wherein the Islet-1 gene was deleted was transplanted compared with the case wherein the wild type retinal tissue was transplanted. Additionally, graphs of the numericalized ratio are shown in FIG. 9B. The same results were also confirmed by FIG. 9B. More specifically, it was revealed that the ratio of the amacrine cells (Am) to the all human cells remained substantially unchanged, whereas the ratio of bipolar cells (Bp) was reduced when the retinal tissue wherein the Islet-1 gene was deleted was transplanted compared with the case where the retinal tissue wherein the Islet-1 gene was not deleted was transplanted. The reduction in ratio of the bipolar cells derived from the graft (human derived) enhanced the contact ratio of the photoreceptor cells derived from the graft to the bipolar cells on the host side (mouse side), suggesting that the functional integration of the retinal tissue after transplant was improved.

INDUSTRIAL APPLICABILITY

According to the present invention, the retinal tissue suitable for transplant can be obtained.

The invention claimed is:

1. A human cell population for transplant, comprising human retinal cells with a modified bipolar cell-regulating gene, wherein:

i. the human retinal cells are human retinal progenitor cells derived from human pluripotent stem cells with a modified bipolar cell-regulating gene and the human retinal progenitor cells are retina and anterior neural fold homeobox (Rax)-positive and Ceh-10 Homeodomain-containing Homolog (Chx10)-positive cells; and ii. the modified bipolar cell-regulating gene is an ISL1 gene, and the ISL1 gene is deleted in whole or part, thereby eliminating expression of ISL1 protein, wherein the human cell population is formed as a cell aggregate and the cell aggregate comprises a retinal tissue.

2. The human cell population for transplant according to claim 1, wherein the ISL1 gene has (1) the nucleotide sequence of SEQ ID NO: 1, 4, or 7; or (2) a nucleotide sequence encoding a protein having the amino acid sequence of SEQ ID NO: 3, 6, or 9.

3. The human cell population for transplant according to claim 1, wherein the eliminating expression of ISL1 protein is by deletion of a region comprising an initiation codon of the ISL1 gene.

4. The human cell population for transplant according to claim 1, wherein the human pluripotent stem cells are human induced pluripotent stem cells or human embryonic stem cells.

5. The human cell population for transplant according to claim 1, wherein a number of the human retinal progenitor cells with the deletion of the ISL1 gene is 10% or more of a total number of cells in the human cell population for transplant.

6. The human cell population for transplant according to claim 1, wherein a functional integration rate of photoreceptor cells induced from the human retinal progenitor cell with the deletion of the ISL1 gene after the transplant is 10% or more.

7. A culture of a human cell population for transplant, comprising:

(1) the human cell population for transplant according to claim 1; and (2) a medium to maintain viability of the human cell population for transplant.

8. A pharmaceutical composition for treating a disease based on a disorder of retinal tissue or a condition of retinal tissue damage, comprising the human cell population for transplant according to claim 1 as an active ingredient.

9. The pharmaceutical composition according to claim 8, wherein the pharmaceutical composition is in a form of cell sheet.

10. A therapeutic agent for a disease based on a disorder of retinal tissue or a condition of retinal tissue damage, comprising the human cell population for transplant according to claim 1.

11. The therapeutic agent according to claim 10, wherein the therapeutic agent is in a form of cell sheet.

12. A method for producing the human cell population for transplant according to claim 1, comprising the following steps (1) and (2):

(1) deleting an ISL1 gene in whole or part to eliminate expression of ISL1 protein in human pluripotent stem cells to obtain in vitro, a human cell population comprising the human pluripotent stem cells with the deletion of the ISL1 gene;

(2) inducing differentiation of the cell population comprising the human pluripotent stem cells with the deletion of the ISL1 gene obtained in step (1) into human retinal progenitor cells with the deletion of the ISL1 gene in vitro to obtain the human cell population for transplant of claim 1.

13. The method of production according to claim 12, wherein the human cell population for transplant is in a form of cell aggregate.

14. The method of production according to claim 12, wherein the ISL1 gene has (1) the nucleotide sequence of SEQ ID NO: 1, 4, or 7; or (2) a nucleotide sequence encoding a protein having the amino acid sequence of SEQ ID NO: 3, 6, or 9.

15. The method of production according to claim 12, wherein the human pluripotent stem cells are human induced pluripotent stem cells or human embryonic stem cells.

16. The method of production according to claim 12, wherein the human retinal progenitor cells with the deletion of the ISL1 gene are Rax-positive and Chx10-positive cells.

17. The method of production according to claim 12, wherein a number of the human retinal progenitor cells with the deletion of the ISL1 gene is 10% or more of a total number of cells in the human cell population for transplant.

18. The method of production according to claim 12, wherein a functional integration rate of photoreceptor cells induced from the human retinal progenitor cells with the deletion of the ISL1 gene after the transplant is 10% or more.

19. A method for treating a disease based on a disorder of retinal tissue or a condition of retinal tissue damage, comprising transplanting an effective amount of the human cell population for transplant according to claim 1 into a subject in need thereof.

* * * * *

SEQUENCE LISTING

```
<160> NUMBER OF SEQ ID NOS: 24

<210> SEQ ID NO 1
<211> LENGTH: 11607
<212> TYPE: DNA
<213> ORGANISM: Homo sapiens

<400> SEQUENCE: 1

gaaggaagag gaagaggagg agagggaggc cagagccaga acagcccggc agcccgagct      60

tcgggggaga acggcctgag ccccgagcaa gttgcctcgg gagccctaat cctctcccgc     120

tggctcgccg agcggtcagt ggcgctcagc ggcggcgagg ctgaaatatg ataatcagaa     180
```

```
cagctgcgcc gcgcgccctg cagccaatgg gcgcggcgct cgcctgacgt ccccgcgcgc    240
tgcgtcagac caatggcgat ggagctgagt tggagcagag aagtttgagt aagagataag    300
gaagagaggt gcccgagccg cgccgagtct gccgccgccg cagcgcctcc gctccgccaa    360
ctccgccggc ttaaattgga ctcctagatc cgcgagggcg cggcgcagcc gagcagcggc    420
tctttcagca ttggcaaccc caggggccaa tatttcccac ttagccacag ctccagcatc    480
ctctctgtgg gctgttcacc aactgtacaa ccaccatttc actgtggaca ttactccctc    540
ttacagatat gggagacatg ggagatccac caaaaagtaa gaggctattt taccttgtgg    600
ggctcggtgt gctgttcttg tgcggggttc tctctcaggc acaggctgag gtgccaaggg    660
ctctttggag ttggagtcat tgcctggaga aagagaaaag gtggcttttt cttgttgccg    720
ccacgcctgc atgcttactg tcggttctta tcttcgggaa actgattgta ccttgtgtgt    780
gaattcgcct gtgtgccctc caaagctcta gctttctggt gctaagcggt gatttcctcc    840
tggggaatcc tgagctctcc gagaaggtta ttatgttgca aaggtctgcc tgcacagtca    900
atgcccagag atgtgaatta gcattagact tgcaaaagag aacgagtgac aactgtattt    960
atgcctgctc ttgctaacaa tatccagtcc tgtgtgctat ttaagagcgc gcttcacgga   1020
aaatatagac atccctgcgt tcacttaacg cttctagtca aaacctttc tttgacttga   1080
cttatccata atctttccca atgattatag caaagaggaa gggggggggg agaaatacaa   1140
aatgagcggg tttgattgcg tgctaggcgt acaaatgtag actattccaa tctgcatttt   1200
acatatattc cacctccttt taaaaatgag tcaaggtttt gatggcacat ttcaattacc   1260
atcccaaagt gcaatgctct aaaaaaaaaa aaaaagaaag aaagaaagaa agaaaaaaac   1320
ctcccagagt acgccctata agagaacgac actaaaagtg tgtttatctc tgtaggaagt   1380
aaacggttag tcaatcatgt atttattttc atttcagaaa aacgtctgat ttccctatgt   1440
gttggttgcg gcaatcagat tcacgatcag tatattctga gggtttctcc ggatttggaa   1500
tggcatgcgg catgtttgaa atgtgcggag tgtaatcagt atttggacga gagctgtaca   1560
tgctttgtta gggatgggaa aacctactgt aaaagagatt atatcaggta tggcatttac   1620
acttctttct taattttgtg ggatttccct gaatctcccc actctttatg tattatttgg   1680
tgtggctttg tctttttgtg aagtttgcct cagtgtagtc atacaagcca aagttaccct   1740
gtacatgtgt taaaaaaatc aagctatgct gttcatttca ttctttagtt gagaaaaaca   1800
aaaaccctta acagtggtat tcataattcc ggggtattga ggcttgttta attactcttg   1860
gagtttatga tgcacaaatt attttcctct ttcaccctcc cccttacaaa acaaaatttt   1920
aaaaagatgg agaagtttgg atttttagct ttaaaatagg gttgattttt gttgtatagt   1980
gcagtgttct gtttgtttta gtccttttta aaattagtag cttacaaatt ctttggtggc   2040
atcaatgcaa taggtgaaat aaaagtttga ccgaagcatg tttagagatg tactttgaaa   2100
gagcgagtac aggtattgct ccttttattt ttggggtaag acctccttct gagaaaaatt   2160
taaaaccaac ctaaatattc cttggaaaaa acaccggaaa cttaatcttt ttaaatatta   2220
accctttggt gacatctaac tgtctcttct ttcttatctt atctgagctg atgaattaga   2280
gcagatcaaa ttgcccatca tctgtctacg aacaattggt atatttagat aattgaacag   2340
cttcctttct cacattaaaa tctggtaact gataaaatga gcgaattgtc caaattgaca   2400
agactgaaac aacataggaa ctttctgagt ttggttttgt tgttttggag agtttttgtt   2460
ttttttttcc tccaatttat tctgcaacac gttttgctaa tctcaagttt cctctgactt   2520
gtgtgtatgt atcagaaact ttgttttctg ccttagaaag ccagtagtct ctaaagaaaa   2580
```

-continued

```
ttgtattcat tttattaaca aacagaagag acatcagcat cattattatg ttaaataata   2640
gcaaaatatc actttttaaa tgtccggtgg ctattaacaa gtaattaatt agcttttgtt   2700
aggcaaatgg tttctggagc ttgagaactt ttattaaagt ttagttaaga tttaatatac   2760
agtcacagtt tgctcctgct cacttagtat ccagcatttt tttcttcttt tttaaaaatc   2820
atgacacaga gagtataatc ttggtagata aaattaacct ggttggggga ggttaatact   2880
tcggagaggg agtgaaagga agtaagggaa gtcggggtac aggaaggggg agggattttc   2940
taaattgttt ggtcaccgcc aaagtcaagt cttcacccta tgaaatggaa gatctcacat   3000
tgagtaggcg gagggaggaa aaacttttga gtccaccttc taacctctga caaatgagcg   3060
ttttcattgt ttactagatt ggtgtgtaaa cgcaagattc tagagaagga gagcccactt   3120
caggagtatc tttactgcta tggaaatagt attttgctca attgcacaca ggcttgcatg   3180
tgcctaattc tggatacaca catgtgtaga aggaactaat catttttacc ttctcttcac   3240
tctctctcaa ctctgtgtgt gtgtgtgtgt gtgtgtgtgt gtgtgtgtgt aatcttgtag   3300
ttgtaaaagc agaacagact ggacagttag atttccacat ctctccttgg agaagcagga   3360
tgcctcctcc tgttatgtgg atcttttcct ctctcttcca ttctttctgt tcgtaggaat   3420
gccccagctt ctgttattcc tgaaagatgg agaaggggcc agggaagtgc agcctagatg   3480
gaacctataa agattgtccc ttggtaagga aaggccagga gtgagaaaga ccttagaagc   3540
gggtctttgc attttttca ttctggtcat ggttttcaag aaaattgaaa tgaggtagat   3600
gattcagcaa cttgaaaaag attgagggaa cagacgcaga ttttttaaa aaaataataa   3660
tacaaggaag aatggagagg aaattttctg ttaacattgc tgcctgaaga aaatctttag   3720
ttggagaaag actggaaagt acttgtgcaa aaggagatgt ggaaactctc agaggtttca   3780
ttttgttatt ctgcttgttt atttgtgagt gtttgcaaac cgagtggggt gacaatcccc   3840
ttctcctacc tcctttttc ttggaaggag gactttttgt tgcagtttta gacatttcta   3900
gcagcagaaa ttgtgggata gggaagtgaa agtgttggtg tcggtggcca ccagagtctt   3960
tctggattcc ttcctgccaa gatctgcaag atcaacactg ggattgattg ctagagcagc   4020
agcccgagtt tggaacccat caatacattt tctgtggtac aagctaggtg ttttgagcta   4080
agagttacca actaagacag aggttcatcg gaaaggaaac gggagtaaaa gaaagggagg   4140
agggagggag gggaaaagag agatggggga aggaagagag acagggaagg agagagcagg   4200
gtttcatttc tgtccttctg tttccaactt ctgtttggaa atgctgttta cttggggcgt   4260
cttgccccggg atcttgggcc agggaagtgc cggcctgaag tgaccccctc ttcctgtact   4320
tctctccccg ctctgggccg cctccgctcc cccctccccc gcacaggttg tacgggatca   4380
aatgcgccaa gtgcagcatc ggcttcagca agaacgactt cgtgatgcgt gcccgctcca   4440
aggtgtatca catcgagtgt ttccgctgtg tggcctgcag ccgccagctc atccctgggg   4500
acgaatttgc gcttcgggag gacggtctct tctgccgagc agaccacgat gtggtggaga   4560
gggccagtct aggcgctggc gacccgctca gtcccctgca tccagcgcgg ccactgcaaa   4620
tggcaggtac tcctctgccc ggctcgggta ggcaggcgcc aggttaagcc agcctgtgtg   4680
ccagcggcca caacaactat ggtagctaca ggggtggtcg tagtgtttgc ctgcagttaa   4740
atgaagtgtt ctgtatgcaa tttgcgctgt gctctgctcc tttgcagcaa ggttcaatgc   4800
actcactgtc tcccttgatt ccccgagcac acctacaccg tctgtgtgtc tctatatggt   4860
tacacataaa tgtacaccac ttgtgtacac gtgtatacac acgcccaaac attacttcca   4920
```

gttcgctctg gcctccaaac cttggcttgc tgaaaacggg cttcagctcc cagccaggta 4980
ttctcctgct gcctaattaa aggggcggag ccccgggtcc ctggagcttc atcctttaac 5040
ccaatgaagg aagcttaggt ggcctgaagt catttagtct cccaaatcct ttttccttgt 5100
gagttgcttc acactcgaaa ttttttttt aattttttta tctttctgtg agagaacagg 5160
actgaaaaga tacagtttta aaaactgcag gccattgcac agagttgtaa tataaaactg 5220
tcaacaagct tatctgcagt aattgccttt taaagggagc ctgcttcttt aaatcattca 5280
ttctatatga tttggtgaga atttcatctt caggcccatg gttgtagctc taaattgacc 5340
ccataggtgt tggcctgacc ctagggggtt gtagaaggtg caggatttgt atcatgtaga 5400
taagaggact cattcccaag gaagaggagt ggaaacacag caaggttggc cgggaccaaa 5460
gcagtgggtt agaaggtgga cagtgtttcc aaacctgact tcctgccatg aatagatcta 5520
ccccttgca gttttaaagt atcaattccc actaaacact gaaggtgagg aaactatagc 5580
cctcccttac ccttctgcct tctggcagct ctaagaattc tgttcagggg gatttgtgac 5640
tagtttgcac cggggcacgg ctggggtggt gctcctgttc agtggagcct gcactctgct 5700
tgtggggaag cacagaggaa gctaaaatac cgagagggag gcgggggaca tctcccagcc 5760
accgtttatc tagagcctag gcagctcaac agagtttccg ttttccactg cttgggatca 5820
gcccatctca ggaacatcca tgtattacct tagatttaat actaagagca gggattggag 5880
atatggcaga aatagcgaat ctcttcagcc ccttcacatg actgtcctct cggactgaag 5940
ttcaaggcgt tctggcagag ttctcgacct tccccttgca gaagtccctg ctggtgtagt 6000
atttatggct gtcactgaag tgctctgcgt tcctttccct ggtaccctct gtggccttgg 6060
cccaagagaa aattctgatc ctggagaggg tggtaatcaa tgtaactggg gcccagtctg 6120
ggcacaagga aaggtgagaa tggaggagaa acagtgctga aaaatgccac ccctgctgtg 6180
aacaggggga cagactttga gacctgcttc ccttggctaa cactttgttg acacgaggag 6240
gggcgagtgc tgcgtttcag gccgggatta ctcagcaaag acctctgcag attagagagg 6300
aagattttat tctccctttc accctcttcg cccccacctc tgccgccccc tgctttgtgt 6360
gctgaggctg caaaccctag ccattgtcct gagtatctcg ggcgggcgag caagtaagcg 6420
ggcgggcggg cgggcaagcg agcgagcgag cgagcgcgcg accgcgggcg ggccggcaag 6480
cgagcctcca gcccagcgct cacggcgctc cttgccccgc agcggagccc atctccgcca 6540
ggcagccagc cctgcggccc cacgtccaca agcagccgga gaagaccacc cgcgtgcgga 6600
ctgtgctgaa cgagaagcag ctgcacacct tgcggacctg ctacgccgca aacccgcggc 6660
cagatgcgct catgaaggag caactggtag agatgacggg cctcagtccc cgtgtgatcc 6720
gggtctggtt tcaaaacaag cggtgcaagg acaagaagcg aagcatcatg atgaagcaac 6780
tccagcagca gcagcccaat gacaaaactg tgagtggctc tggggccggg cagggaatgc 6840
gagggggaag gagacgcagc gtgcgaggtg cgttcctggt acgcaggatc gcacggtttt 6900
caatcctgct cctgggcagg agtttggccg gggctgcccc tcatccttac ccccctaccc 6960
atgccccggg ggacaggcta cccggcgccg gccgccagct gagggcgggg aagctgggag 7020
gctccgtgcg ccgggggagc agcatccagg tcccaacctc gtgggtgggc tcatgccctt 7080
ccacctcgcc tgtacctgtg aaccggagaa acgccgtcct cccctctgag ggcaggcggc 7140
aacgaggttt ggcccgggtt ttgccaacat tcagatcgtc agttcctcac gtacacaaga 7200
agagggaggg ataatacctt ggattcctgc ctacatccag gggttccgtg ggcaggtcac 7260
cctgtgagcc cccagggcgc accgcacttc taagtaaggt cggccgctgc gccttcaggc 7320

-continued

```
tggcgagttc ccccaaggtg acccgcatgc ccagatcacc ctctgctcca ggtgaagccc   7380
aggcctccac agaggcatca ggcccctcgc accagtatcc actgttatct tggtcccacg   7440
gaagcaccca ctctgcaggc ctcctggtga agttaagcta gagtttcttt tcttcctttt   7500
tttcttttct ttctttttct tttttttttt tttttttttt tttttttttt ttttttttact   7560
gctttggacc tatttttaaa tgccataaaa tctgctgtca ttaaacttgg caggctggcc   7620
aagattgggc cagggcactt tctgagttgg ttagtgcata atagcacaat aggaaccaga   7680
cccaaatgct ttggggggat ggagtggggg gctggctctt ccttgaggag aacggcttgg   7740
aaaaaatctg cagctaactg aaactgctca gaaaaccacc ctgtctagag gctgaaggga   7800
agccctgctt acctcagctt tttagttctg ggaagctatg gtctgagaag gcagagggga   7860
ggaattgggc tgagctgtga aggtaagggg gaagaagaaa atcaaagtag aatttggttt   7920
aataaggtcc atgcagacct aatagtccag cccacagagg cagaaaaaca aaacaataaa   7980
acaaattgaa ttctaactaa tatccgtagg tacggcggat taactgagtc aataaagacc   8040
actatataga taagataata ccagggtata tttgcttagc ctgtgcagac aacggaggga   8100
gggaatttgc tcattaacat gttgggattg gttgggggc ctattcacag aatatccagg   8160
ggatgacagg aactcccatg gtggctgcca gtccagagag acacgacggt ggcttacagg   8220
ctaacccagt ggaagtacaa agttaccagc caccttggaa agtactgagc gacttcgcct   8280
tgcagagtga catagatcag cctgcttttc agcaactggt aagtgtcagc tcccagatgg   8340
aagaggctga attcccaaca ggagactctg gtttaactgt cacacattga aagattcagt   8400
ggggagggtg ccttcttggg ctcagggttg ggagaaaacc aaggaggtgg gtaatgaaga   8460
gaagggagac aaatgcaggg aaaacgaacc tcttggcatc tttttttttt taatgagact   8520
gcataatttg accatatagg ttgaattttc tatcaatcag gccttctttg aaggattaat   8580
ttcaaggtac ctaactctag gtagcatgtg ccagaagatg tacagtgttg gagaatcata   8640
catcttagaa ttttagagtt gtcaaggact tcaggaaatc gtcttggcat ttcaatcagc   8700
aattagtaag tttatccttc ctgagcatct agagaatggg atatatagga cccaaatcaa   8760
ggcgattgta gtatataatc aatgctataa tacacaatca gtgttgttat caataaacag   8820
caggcatgtg tctgggtaca attttcaaat atattaataa agattattca aatagatgaa   8880
tactttttgt tacagtatcc cttgctggga atgtcttaat ctaaaatgta ggaccgttta   8940
aatgttttca agtgtatgag ttcaaatgtc atagagacac acagtgtgta ccatgtatag   9000
caaaagggac atgagctcta ccaatcagaa gtaaagtgtt taatctgtga aaaccttaac   9060
atgttttcca catccagaga ggagaaaatt aattcacttt ttgcctacaa aaggcttaag   9120
gggtcaagat aaataagaac aataaatata tgtcctttgt aatatgctat atttatatag   9180
atgatttttt tttcttaaag agtaatcagc cttatagaat cttgttttat aaaatgtaaa   9240
gatctatcct gaaaccttgt tccctttttt ggaaatgaag ctttagttga ggttagcttt   9300
ttaccctcat atttacctgg agggcatttg ctttctcaat gtcaacagtt aggtaattgg   9360
ccagaggcaa gtggttaaaa gggcttggcc ccaggcttgt gtttgcaaat gctaagtggg   9420
tgcagaggct agaagtccct taatctcata ttggaaaaat ttactgtaga aagaaatgta   9480
ggctctagaa ctaggaaaaa aaaattattc taagctcatt aatctgttga gttatttgag   9540
cgaatcctga atcacaggag gaaggtaagg ggaggcttca gggcagccaa atgtttgcac   9600
tttctgaaac tttagtgtca gatgagagca gtggaaggga agctgaggca ggagtgggca   9660
```

-continued

```
tagttagaga aggtttacaa cagcagtaca atgcgtttag ggttaaaaga aggagtcaga   9720

tatttaagaa ggagtcagat attagggtta aaagaaggag tcagaatggg atgatgtcat   9780

aatatatggg tctcattttg gaaggaagag cctgatttaa agagagagag agagaaaggc   9840

caagaggcag caggaccaac aaggaagaat gcccaagctg tgagcctgct gaggagttaa   9900

tctttgttct gtggagcctc ctctcaatct cctgtcaaag gatctgagcc tgttacggat   9960

tttccaactg aagaagagag tctttgatgc ctagagactg agagctcacc tactcccagg  10020

gcaacatgta gccagcagga taattttatt tcgagcatgc atagtagagt tgtgatgcca  10080

ttttacagtg ggaaacacat ttgttcttaa ataatttaat gcaacataat gttgggaatt  10140

cagtttcagt taaaacagag atcttttgga agatgggaaa gtgagaggat ttcttcccaa  10200

gtttttctcc tctaggcttt ctctaagcct gttaaaattc agttatctat gtgaatatct  10260

ttacatatct atctacacaa acatttctac atatacaata tgatgagttt ataatctttt  10320

tatgaatact attccagtgt cctttattta tttctcaacc ttctatgcag gtcaattttt  10380

cagaaggagg accgggctct aattccactg gcagtgaagt agcatcaatg tcctctcaac  10440

ttccagatac acctaacagc atggtagcca gtcctattga ggcatgagga acattcattc  10500

tgtatttttt ttccctgttg gagaaagtgg gaaattataa tgtcgaactc tgaaacaaaa  10560

gtatttaacg acccagtcaa tgaaaactga atcaagaaat gaatgctcca tgaaatgcac  10620

gaagtctgtt ttaatgacaa ggtgatatgg tagcaacact gtgaagacaa tcatgggatt  10680

ttactagaat taaacaacaa acaaaacgca aaacccagta tatgctattc aatgatctta  10740

gaagtactga aaaaaaaaga cgtttttaaa acgtagagga tttatattca aggatctcaa  10800

agaaagcatt ttcatttcac tgcacatcta gagaaaaaca aaaatagaaa attttctagt  10860

ccatcctaat ctgaatggtg ctgtttctat attggtcatt gccttgccaa acaggagctc  10920

cagcaaaagc gcaggaagag agactggcct ccttggctga aagagtcctt tcaggaaggt  10980

ggagctgcat tggtttgata tgtttaaagt tgactttaac aaggggttaa ttgaaatcct  11040

gggtctcttg gcctgtcctg tagctggttt atttttttact ttgccccctc cccacttttt  11100

ttgagatcca tcctttatca agaagtctga agcgactata aaggtttttg aattcagatt  11160

taaaaaccaa cttataaagc attgcaacaa ggttacctct attttgccac aagcgtctcg  11220

ggattgtgtt tgacttgtgt ctgtccaaga acttttcccc caaagatgtg tatagttatt  11280

ggttaaaatg actgttttct ctctctatgg aaataaaaag gaaaaaaaaa aaggaaactt  11340

tttttgtttg ctcttgcatt gcaaaaatta taaagtaatt tattatttat tgtcggaaga  11400

cttgccactt ttcatgtcat ttgacatttt ttgtttgctg aagtgaaaaa aaaagataaa  11460

ggttgtacgg tggtctttga attatatgtc taattctatg tgttttgtct ttttcttaaa  11520

tattatgtga aatcaaagcg ccatatgtag aattatatct tcaggactat ttcactaata  11580

aacatttggc atagataaat aaataaa                                      11607
```

<210> SEQ ID NO 2
<211> LENGTH: 2729
<212> TYPE: DNA
<213> ORGANISM: Homo sapiens
<220> FEATURE:
<221> NAME/KEY: CDS
<222> LOCATION: (549)..(1598)

<400> SEQUENCE: 2

```
gaaggaagag gaagaggagg agagggaggc cagagccaga acagcccggc agcccgagct     60
```

-continued

```
tcgggggaga acggcctgag ccccgagcaa gttgcctcgg gagccctaat cctctcccgc    120

tggctcgccg agcggtcagt ggcgctcagc ggcggcgagg ctgaaatatg ataatcagaa    180

cagctgcgcc gcgcgccctg cagccaatgg gcgcggcgct cgcctgacgt ccccgcgcgc    240

tgcgtcagac caatggcgat ggagctgagt tggagcagag aagtttgagt aagagataag    300

gaagagaggt gcccgagccg cgccgagtct gccgccgccg cagcgcctcc gctccgccaa    360

ctccgccggc ttaaattgga ctcctagatc cgcgagggcg cggcgcagcc gagcagcggc    420

tctttcagca ttggcaaccc caggggccaa tatttcccac ttagccacag ctccagcatc    480

ctctctgtgg gctgttcacc aactgtacaa ccaccatttc actgtggaca ttactccctc    540

ttacagat atg gga gac atg gga gat cca cca aaa aaa aaa cgt ctg att     590
         Met Gly Asp Met Gly Asp Pro Pro Lys Lys Lys Arg Leu Ile
         1               5                   10

tcc cta tgt gtt ggt tgc ggc aat cag att cac gat cag tat att ctg      638
Ser Leu Cys Val Gly Cys Gly Asn Gln Ile His Asp Gln Tyr Ile Leu
15                  20                  25                  30

agg gtt tct ccg gat ttg gaa tgg cat gcg gca tgt ttg aaa tgt gcg      686
Arg Val Ser Pro Asp Leu Glu Trp His Ala Ala Cys Leu Lys Cys Ala
                35                  40                  45

gag tgt aat cag tat ttg gac gag agc tgt aca tgc ttt gtt agg gat      734
Glu Cys Asn Gln Tyr Leu Asp Glu Ser Cys Thr Cys Phe Val Arg Asp
            50                  55                  60

ggg aaa acc tac tgt aaa aga gat tat atc agg ttg tac ggg atc aaa      782
Gly Lys Thr Tyr Cys Lys Arg Asp Tyr Ile Arg Leu Tyr Gly Ile Lys
        65                  70                  75

tgc gcc aag tgc agc atc ggc ttc agc aag aac gac ttc gtg atg cgt      830
Cys Ala Lys Cys Ser Ile Gly Phe Ser Lys Asn Asp Phe Val Met Arg
    80                  85                  90

gcc cgc tcc aag gtg tat cac atc gag tgt ttc cgc tgt gtg gcc tgc      878
Ala Arg Ser Lys Val Tyr His Ile Glu Cys Phe Arg Cys Val Ala Cys
95                  100                 105                 110

agc cgc cag ctc atc cct ggg gac gaa ttt gcg ctt cgg gag gac ggt      926
Ser Arg Gln Leu Ile Pro Gly Asp Glu Phe Ala Leu Arg Glu Asp Gly
                115                 120                 125

ctc ttc tgc cga gca gac cac gat gtg gtg gag agg gcc agt cta ggc      974
Leu Phe Cys Arg Ala Asp His Asp Val Val Glu Arg Ala Ser Leu Gly
            130                 135                 140

gct ggc gac ccg ctc agt ccc ctg cat cca gcg cgg cca ctg caa atg     1022
Ala Gly Asp Pro Leu Ser Pro Leu His Pro Ala Arg Pro Leu Gln Met
        145                 150                 155

gca gcg gag ccc atc tcc gcc agg cag cca gcc ctg cgg ccc cac gtc     1070
Ala Ala Glu Pro Ile Ser Ala Arg Gln Pro Ala Leu Arg Pro His Val
    160                 165                 170

cac aag cag ccg gag aag acc acc cgc gtg cgg act gtg ctg aac gag     1118
His Lys Gln Pro Glu Lys Thr Thr Arg Val Arg Thr Val Leu Asn Glu
175                 180                 185                 190

aag cag ctg cac acc ttg cgg acc tgc tac gcc gca aac ccg cgg cca     1166
Lys Gln Leu His Thr Leu Arg Thr Cys Tyr Ala Ala Asn Pro Arg Pro
                195                 200                 205

gat gcg ctc atg aag gag caa ctg gta gag atg acg ggc ctc agt ccc     1214
Asp Ala Leu Met Lys Glu Gln Leu Val Glu Met Thr Gly Leu Ser Pro
            210                 215                 220

cgt gtg atc cgg gtc tgg ttt caa aac aag cgg tgc aag gac aag aag     1262
Arg Val Ile Arg Val Trp Phe Gln Asn Lys Arg Cys Lys Asp Lys Lys
        225                 230                 235

cga agc atc atg atg aag caa ctc cag cag cag cag ccc aat gac aaa     1310
Arg Ser Ile Met Met Lys Gln Leu Gln Gln Gln Gln Pro Asn Asp Lys
    240                 245                 250
```

```
act aat atc cag ggg atg aca gga act ccc atg gtg gct gcc agt cca     1358
Thr Asn Ile Gln Gly Met Thr Gly Thr Pro Met Val Ala Ala Ser Pro
255                 260                 265                 270

gag aga cac gac ggt ggc tta cag gct aac cca gtg gaa gta caa agt     1406
Glu Arg His Asp Gly Gly Leu Gln Ala Asn Pro Val Glu Val Gln Ser
                275                 280                 285

tac cag cca cct tgg aaa gta ctg agc gac ttc gcc ttg cag agt gac     1454
Tyr Gln Pro Pro Trp Lys Val Leu Ser Asp Phe Ala Leu Gln Ser Asp
            290                 295                 300

ata gat cag cct gct ttt cag caa ctg gtc aat ttt tca gaa gga gga     1502
Ile Asp Gln Pro Ala Phe Gln Gln Leu Val Asn Phe Ser Glu Gly Gly
        305                 310                 315

ccg ggc tct aat tcc act ggc agt gaa gta gca tca atg tcc tct caa     1550
Pro Gly Ser Asn Ser Thr Gly Ser Glu Val Ala Ser Met Ser Ser Gln
    320                 325                 330

ctt cca gat aca cct aac agc atg gta gcc agt cct att gag gca tga     1598
Leu Pro Asp Thr Pro Asn Ser Met Val Ala Ser Pro Ile Glu Ala
335                 340                 345

ggaacattca ttctgtattt tttttccctg ttggagaaag tgggaaatta taatgtcgaa   1658

ctctgaaaca aaagtattta acgacccagt caatgaaaac tgaatcaaga aatgaatgct   1718

ccatgaaatg cacgaagtct gttttaatga caaggtgata tggtagcaac actgtgaaga   1778

caatcatggg attttactag aattaaacaa caaacaaaac gcaaaaccca gtatatgcta   1838

ttcaatgatc ttagaagtac tgaaaaaaaa agacgttttt aaaacgtaga ggatttatat   1898

tcaaggatct caaagaaagc attttcattt cactgcacat ctagagaaaa acaaaaatag   1958

aaaattttct agtccatcct aatctgaatg gtgctgtttc tatattggtc attgccttgc   2018

caaacaggag ctccagcaaa agcgcaggaa gagagactgg cctccttggc tgaaagagtc   2078

ctttcaggaa ggtggagctg cattggtttg atatgtttaa agttgacttt aacaaggggt   2138

taattgaaat cctgggtctc ttggcctgtc ctgtagctgg tttatttttt actttgcccc   2198

ctccccactt tttttgagat ccatccttta tcaagaagtc tgaagcgact ataaaggttt   2258

ttgaattcag atttaaaaac caacttataa agcattgcaa caaggttacc tctattttgc   2318

cacaagcgtc tcgggattgt gtttgacttg tgtctgtcca agaacttttc ccccaaagat   2378

gtgtatagtt attggttaaa atgactgttt tctctctcta tggaaataaa aaggaaaaaa   2438

aaaaaggaaa cttttttgt ttgctcttgc attgcaaaaa ttataaagta atttattatt   2498

tattgtcgga agacttgcca cttttcatgt catttgacat tttttgtttg ctgaagtgaa   2558

aaaaaaagat aaaggttgta cggtggtctt tgaattatat gtctaattct atgtgttttg   2618

tctttttctt aaatattatg tgaaatcaaa gcgccatatg tagaattata tcttcaggac   2678

tatttcacta ataaacattt ggcatagata aataaataaa aaaaaaaaaa a            2729


<210> SEQ ID NO 3
<211> LENGTH: 349
<212> TYPE: PRT
<213> ORGANISM: Homo sapiens

<400> SEQUENCE: 3

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45
```

-continued

```
Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
    290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
                325                 330                 335

Asp Thr Pro Asn Ser Met Val Ala Ser Pro Ile Glu Ala
            340                 345
```

<210> SEQ ID NO 4
<211> LENGTH: 11465
<212> TYPE: DNA
<213> ORGANISM: Mouse

<400> SEQUENCE: 4

```
caatggcgat ggagctgagt tggagctgag aagtttgagt aagagataag gaagagaggt      60

gccccgagcc gtgcgagtcc gccgctgctg ctgcgcctcc gctctgccaa ctccgccggc     120

ttaaatcgga ctcccagatc tgcgagggcg cggcgcagcc gggcagctgt ttcccccagt     180

tttggcaacc ccgggggcca ctatttgcca cctagccaca gcaccagcat cctctctgtg     240

ggctattcac caattgtcca accaccattt cactgtggac attactccct cttacagata     300

tgggagacat gggcgatcca ccaaaaagta agaagcggtt taaccttgtg gggcttggtg     360

tgctgttgtg gtgtgggggg gtctctctca ggcaccgatg acagggctct ttggatttgt     420
```

```
agtcactgcc tggagagaca gaagagaagg tggtcctttt gttgttgttg ttgctgctgc    480
tgttgtgtgt gtgtgtgtgt gtgtgtgtgt gtgtgtgtgt gtgtgtgtgt gtgtgtgtgt    540
tttcttcttg tcacgcttgc agcttgcatg tttggtgtga attccgatct ttgagaaact    600
gatcatacct tgtgtttgaa tgctctgtgc cctcccaaac tctagccgcc tgcccggtgc    660
ttagcggtga tttcctcctc cggattccgg agctcttgga gaagttatta tgtagcaaag    720
gtctgcctgc acaaaccaca ccggcagata tgaattagca ttagacttgc aaaagagagc    780
gagtgacaac tgtattgatg tctactcttc taacaatatc cattcccgcg tgctattgaa    840
gaacgtgctt cacggaaaat atagacatcc cagcgttgct ttaacgcttc tagtcaaaac    900
cttttctttg acatgactta tccataatct tgcctaatga ttatagcaaa gagggaggag    960
ggagaaaaca caaaatgagc gggtttgatt gcgtgctaag cttacaatgt agactattca   1020
aatctgcgtt ttacatatat tccacctccc tttttaaaaa agcgagtcaa ggttttgatg   1080
gcacactcca attaccatcc caaagtgcaa tactctttaa gggaagaaca agaaaaaaaa   1140
aaaaagggaa agaaaaaaat tcttccagaa tacaccctat aagagaacga cactaaaagt   1200
gtgtttatct ctgtaggaag taaacggtta gtcaatcatg catttatttt catttcagaa   1260
aaacgtctga tttccctgtg tgttggttgc ggcaatcaaa ttcacgacca gtatattctg   1320
agggtttctc cggatttgga gtggcatgca gcatgtttga aatgtgcgga gtgtaatcag   1380
tatttggacg aaagctgtac gtgctttgtt agggatggga aaacctactg taaaagagat   1440
tatatcaggt atgccatttt tacagggtta ttttctgaga tttcttggct ctccttgttt   1500
attatttgat gtgccctttgt tttgttttgt tgtttttaga gggagggaga acgtttactt   1560
tagagtgccc agtgtacaag aaatgttttt aaaattaaac tgttgttcat ttcatatctt   1620
tggggggtgg ggtgtcgctg tgtttcataa atttttgttg ataaggtttg ttaatgactc   1680
tttgaatttt tcatacaaaa gattatttcc ctctttaaac ttccctaagg acaacaacaa   1740
aattaaggca aataagttta gggtttcaaa ctttaaaaat tctattttca ctgtatagtt   1800
tatcatctta tttattttc tcctgtttta tcaatgactt acattatttt gggggctcca   1860
aataaacaga caaaagtttc accaaaggat ttttgaagaa caagtacaaa cattgctccc   1920
tttacttttg gggtgactct tcctttgata aaaaatttta aaaccaaaat aaaatattcc   1980
ttaacgcccc ccccccaaaa aaaaccaccg gaaatttaat ctttttaaat attaaccctt   2040
tggtgatatc taactgcctt ttctttctta tcttatctgg gctgatgaat tagacagagc   2100
agatcaaatt gcccatcatc tgtctgcgaa caattggtat atttaggtaa ttgaacagct   2160
tcctttctca cattaaaatc tagtaactga taaaatgagg gaatcagctg acggacaaga   2220
ccaaaaccag ggaggaggat ctgagctggc ttttgttgca cttttttttt tttcctaatt   2280
tcaagtttct ctgacctacc agtttatatc agaaacttga ctttctacct tagaaagcct   2340
ggtagaattt ctaaaggaaa atgtgtttgt tctaatacaa agcaagatac tgttcccctt   2400
cactgttagg ctggcgatgg cagaaatgta gccgatttta gatttcagag gtggccattg   2460
gcaagtgatc ggcttttcct aagccataaa gcgctttgga gcttcagaac tttcattaaa   2520
gtttagttaa gatttaaaat acagccccac cagtttttct cctgctggaa taatgcccct   2580
ccctcggttt tgttttgttt tgctttaaaa aaaacataga ttggaggata tattcatgat   2640
agctaaaatt aaacaatata ctagggaggg tttgcttgtt tgtttgtttg gtttggtttt   2700
aatgacaagg agaatgggag gaagtgggat acaggaaagg ggagggattt cgtcaatggt   2760
```

-continued

```
ttgggaaccc ggcaaagtaa gtcttccttc tataaaatgg atgatcttgc attggagagg   2820
cagaaggtag gaaaaaaaat ttcaagtctg tcttccaacc tctgagaaat aatccctttt   2880
catcttttac ttggctggtg tggctctcg ggacactgga gagggagaag ggagaaccta   2940
ctttgaaact ccaaaagcat ctttacgcct ctgaagatac tgtttccctc ccttgtatac   3000
agacttgctt cattccggat ctgtcaattt gcagatggag tcactcagtt acttttcctt   3060
ttctcttctc ttctcttccg cctgggagca tgtttgtaag tgtgtgtgtg tgtgtgtgtg   3120
tgtgtgtgtg tgtgtgtgta acacccatgc acaacccttt tggaggatct atagttgtaa   3180
aagcagggta gagtgaccat ttttatttta aggtctctca ttggggaagc aacatgccac   3240
ctcctttgtg tggatcttgt cctatctttt ttcactctct atgtagaaat tactgatagc   3300
tattgaggga tatccaggca atgaagcagt ggatggacta taaggactat aaggactgag   3360
cggtggtaag gaaaggctga caggggagga agcttttagc agtgcgggtt ggttttgttg   3420
ttttttgtc catttgtctt gctagccttg tcccccaggc aaactgaagt agaggtacat   3480
gctttaggaa ccgaggaaag actggttgga ggaacagaag ctgggcatta aaataaaaga   3540
ggaagaatgg agaaagaact ttccattaac aagagccccg tggaaaatct ttagttggat   3600
aaatactgga aggccttcac tggagaggac ctggaaactc tctagtgctt catcttgtta   3660
ttgcgttctg ggattttgtg tgttcagatg gagtggggtg accctcagtc cccttcccca   3720
cctttgttgt tgatggtgat gatggtggtg gtggtggtgg tgtgcttttt cagaaatact   3780
tttagtagca gaaattgagg gatagagaat ggaaagcata gggctactgg ccactaatgt   3840
cccctgaatc cctccctgca agtatttgca agaataatcc tgagactggt accagaggct   3900
ggttcgaggt ttagaatcca tcaataaatt ttccttggtt tgggctgagt gcctgaacta   3960
agaggtacaa acttagacag acacagaggt tcaccataaa ggttcccctt gttaaagggg   4020
aggttaagga agaaggaggg agaggaagag aagggggagg agggaggaag ggggtggggt   4080
tgtttctata ttctgcccaa ctttgctatt gctatttttt tttccaggca ggtcaggttt   4140
atggcccggg tctctggcca tcttgggaca gaacctgcct gaaatcaccc atttttgtgt   4200
gtgtgtgtgt gcttttcttc ccatgccggg gccggttcat tcaggttgta cgggatcaaa   4260
tgcgccaagt gcagcatagg cttcagcaag aacgacttcg tgatgcgtgc ccgctctaag   4320
gtgtaccaca tcgagtgttt ccgctgtgta gcctgcagcc gacagctcat cccgggagac   4380
gaattcgccc tgcgggagga tgggcttttc tgccgtgcag accacgatgt ggtggagaga   4440
gccagcctgg gagctggaga ccctctcagt cccttgcatc cagcgcggcc tctgcaaatg   4500
gcaggtactc ctccacccag aggctgagaa aaggcaggcg gggctaaatc ataacctttc   4560
tttcctgcaa cctaggggtc acacagtggt gcagaaagtg gcctgcagta aaccacacgt   4620
gctctttgcc tttctagcaa atttccatac actcgtcgtc tgccttgacg gcacaaccac   4680
acatctaaat gtctgtctat atacaagtac acagcatacc ccgcttgtgc acacatgtat   4740
acacaagccc aaactgtact gtcagcttta ctttggcctc taacccatag cttactgaaa   4800
atgggcttca gctctctgcc aggttttctc ctagctgccg cctaattaaa ggggtggagc   4860
cctaggtctc gaggagtttc ctccctagcc ctgcgaagga agcttaagca gccccaaggc   4920
atttagcttc ccacctctct ctctctctct ctctctctct ctctctctct ctctctctct   4980
ctctctctct ccctctccct ctccctctcc ctctccctct ccctctctct ctctctctct   5040
ctctctctcc cccccccttg ggatttactt tccaatccaa aagcttttta aaatttattt   5100
ttatgccttt gtcaaaaaac aaaacaaaca aacaaacaaa aacccccatg tccctaaaag   5160
```

atacagtgtc agtaactgca ggcactgcac aggactgtaa cttaaaactg tcaacagcct 5220
aatctgcagt aattgccttt taaaaaggag cctgcctctt taagccattc attctacgtg 5280
atttggtgag aatttcatct ccaagcctgt agctgtagct ctaaattgac cccataggtg 5340
tttggcctga ccccaggggg gcgtggaagg tgtgggattt gtaccgtgga gatcagagga 5400
ccagttgccc ataaaggaaa gtggaaacac aaaggttggc taaaaccaag accggcagac 5460
agcagaacat tgtttcctcc ctgccttcca gtcagaagca ggtctccatc cctccatccc 5520
cgttagtata aagccatcag ctcctactaa ataccagagg tgagaaaatg acagcttttc 5580
cccaaccccc aactcacctc ttctagctgc tctgcaattc ttccctgagt gatgtctaac 5640
tagcagacaa gggataaagc caagggtgag aaacggcaga agaggcagaa atcttgggag 5700
ggaagggaag gaccgtctcc actcctcagt catctcaagc tcagacagtt caacagagtt 5760
tcagttttct tttgcttggg gtcagcgggt ctctggaaca tcccacattg ttgatttagt 5820
actaagaaag acaggcggac cattcgggta gttggaatcc agcatttctt tagcttctaa 5880
atatgattgt cccctagaac tgaagttcaa ggctttctgg cataattatc tgacttttgg 5940
tcgcagactt cccagccctg tcgtgtctct agctgtcact ggggtgttct gcgttttatt 6000
ttcaggtacc ctctatgact ttaatccaga agggaaaggc aagcctggag gtgggggtgt 6060
aatctgtgac cttcttctgg ttatgaggga agggggaggg gagagatttt actgttgaaa 6120
aaaaaatgtc tctggtgcgg gtggagacag acttctttcg gctaattgtg tagtgaatgg 6180
ggagtaggaa caggggttgc atctcttatc tcccccatta ctctctgcat tgtcttctat 6240
tgactaagga gcgagagatc ttcttcctcc tcatccctac cctctgctgt ttctgcgagg 6300
tgtgctgagc cagggctaga tagggaatgg agtgggctga tggtggcggg agtggccttg 6360
catgctcacc gagtcccttt gccccgtagc cgaacccatc tcggctaggc agccagctct 6420
gcggccgcac gtccacaagc agccggagaa gaccacccga gtgcggactg tgctcaacga 6480
gaagcagctg cacaccttgc ggacctgcta tgccgccaac cctcggccag atgcgctcat 6540
gaaggagcaa ctagtggaga tgacgggcct cagtcccaga gtcatccgag tgtggtttca 6600
aaacaagcgg tgcaaggaca agaaacgcag catcatgatg aagcagctcc agcagcagca 6660
acccaacgac aaaactgtga gtagccccga agctaagcaa ggaagggatg ctaggagacc 6720
ttggaagacc gggctagcgg ggcatccctg tgatctgatg gattggtact ctgtggagca 6780
ccagcaggag cccaaaccaa ggtggacctc tcacttcacc taaacccagg tgtatagtgt 6840
ctactctcta caagaaggcc gagatttggc tggttagaaa ctgcagacgt ctgagtggtg 6900
cccatcctcc cccatccatt gctgattcca aaaggggtca tggtcttcat caccatgggc 6960
accctggaac ctaaaggacc tagtggctcc ctccctccca gggcagatgg tgcgaggtct 7020
tgaactcagg ttctgcaagc attggcacca ttagagttgc tcccgttgtg aagggcaaca 7080
tcttgagtgc tgatctagaa catgattcaa tatactttcc atctatccag cattctggtc 7140
tcaccccaac tcttggcaag acttgccact gtttttgcat ttgggagatc ccttcaaggt 7200
gcccatgcag acactcccct cttccaagct tccttccagc ctttggtatc attatgttag 7260
gcaacaacac actccccttc cacccccctc ccccacctct tgcttaagtt aaggtaaagg 7320
ttttttgttt ttttttttta aactacttca gccctatttt taaatgccat tttttaaaaa 7380
aaatccattg tcattaaact tggcaggcag accgagactg ggtaagggta ctttctaagt 7440
tagagcataa tagcacagaa gtagccagac ccagaaacct tggggctagg gtggggtaag 7500

-continued

```
tatgattctg gaaggaagag tgcttagggg caggggggatg ggttcagcta actcaaactg   7560
cctagaaaac cagtatcaga aggctgaagg gagacagacc ctggctggac ctcagttttc   7620
tagttctggg agactgtggc ctcttaacgc aggtgggagg ggttggggta gggcataagc   7680
tgtgaaggtg aagcaaaagg tgatagatgc agcagaattg ttttaataag atctcagcca   7740
gtctcataat ccactgcaca gaagtagaaa aacaaaactg aactcaaact catatccata   7800
ggtacagcag attaactgag tcaatacagg gccactgtgt agataagata aatacttggg   7860
tatatttact tagcacatgc agaccaggaa gggagggagt ttgctcatta acatgttggg   7920
atggggggggg gcgttattca cagaatatcc aggggatgac aggaactccc atggtggctg   7980
ctagtccgga gagacatgat ggtggtttac aggctaaccc agtagaggtg caaagttacc   8040
agccgccctg gaaagtactg agtgacttcg ccttgcaaag cgacatagat cagcctgctt   8100
ttcagcaact ggtaagtgtc tggctcccaa atgggaaaag actggatccc taacaaaaaa   8160
aggagactcg ttttaactgt taggcattga aaggtcccct ggggtgaggg agggtaccgg   8220
gattagagag aaagcaggat gtggtggtga agaggaggga ggcagatgga aggaaaggag   8280
atctcttgtg aatctttgtt taaaactgag atgccacaat ttaactatgt agcctaagtg   8340
tgtagtgtga tcttcctaca aaggaggcat atcttatggg ttgagcttct cagtgcctaa   8400
gtagttctgt gtacagaggt acagacagtg gcaatgtcac atattttagg ctgttctaaa   8460
ttacaaggac ttcagagacc accgtggcat ttggatcagc aatcagtaag ttctttgctt   8520
tacctgtgtc ttgtgactga ttcaagtaaa aatgactggg atgcacgccc agtgtgatac   8580
ccagttagaa tgcagttgtg cataagcagc agggagctgt ctgaacacaa ttctcttcta   8640
tgtcaaccac gaggatagtt atttaaatag tttggttgat atttattatt gttatgtttc   8700
tttcaaagca cagattgatc taaagcagag gattttaaaa atatttttaa acaaatgagt   8760
tcagatatga cacaattaca ttcagtgtgg catgtatgcc aaaaggaaca tgagcattgt   8820
cagaggcaat gcatatttaa cttgtgaaaa cctgtcttag cactaaaggg tctaacacat   8880
tcatccatag cagagaatta attcatttta cctataaaag gttaagataa agaaaaattt   8940
aaagatagat cggtgtggtg catatgctta aggttttttt tcttcttcct taaaggatga   9000
tcagccccat agatactgtt ttattaaaca cgaagctgag tcctaaaaaa cacccctttc   9060
tttagaagca cagttaatgc atcaattgag aataggtttc cccccattct atcctgtgcc   9120
ctaagcatat ttgctttctc ttgtcaacag ttataagggt gattggccag aggcaagtgc   9180
ttaaaagggc ttggtaccat gctctctctc tctctctctc tctctctctt tctctctctc   9240
tcctccccac ccccgtgtgt gtgtgtgtgt gtgtgtgtgt gtgtgtgtgt gtgtgtgtgt   9300
gtgtgtgtat gtgtatgtgt aaatgggcca atctagtgag caggcaaatt tgagaagtcc   9360
cctgacctcg caaggagaag gtttaataga tagtagataa gggattctgg agccaaagag   9420
aaagtttttc cttaaataaa acaaattgtc cctaggaagc attctgtagg taaactttga   9480
ataatagaaa aggaggtgag agggggcttg gttcctcctg aaacttgagt gtcaggtgag   9540
aacggtgaag tggaacccga ggaaggggta ggagggtatg gttatgggtg ggggtgacag   9600
tttacgtcac actgaattta taatgagatg atgaatgtgt aggtctcctt gtggaaaggg   9660
gaggaggggt caggcaatga gagcacactg tgaatccact aaagagttaa gcattgttcc   9720
tcaggagcct gccttgaatt tctggcctag agaactttcc tactccccgg gctagtaggc   9780
agctggataa ttttatttca agccttagag ggagagttat gatgccactt tacagtggga   9840
aacacatttg ctcttaaata atttaatagg acacaatgtt gggaattcag cttgggttaa   9900
```

-continued

```
aagagagctc tttaggaaga tggagaaatg gagagcattt ctttgcaagt gcttctcctg   9960

ggcttccttt aaagcctgtt taaattctat gacaggcata ggtatctttg ttggtatacc  10020

agttctactt acaggaactt ataggcgtag actcaatgta atacttttgt atagctcggg  10080

acactactga agcccctttt gctgacttct caaccttcca tacaggtcaa tttttcagaa  10140

ggaggaccag gctctaattc tactggcagt gaagtagcat cgatgtcctc gcagctccca  10200

gatacaccca acagcatggt agccagtcct attgaggcat gaggaacatt cattcagatg  10260

ttttgttttg ttttgttttg tttttttccc ctgttggaga aagtgggaaa tgacgttgaa  10320

ctccgaaata aaaagtattt aacgacccag tcaatggaaa ctgaatcaag aaatgaacgc  10380

tccaggaagc gcatgaagtc tgttctaatg acaaagtgat atggtagcaa cactgtgaag  10440

acaatcatgg gattttacta gaataaaaac aaacaaacaa acaaaaccct aagcccaaca  10500

tatgctattc aatgacctta ggagtactta aaaaagaaaa agaaaaaaaa aagagagaga  10560

gaccgttttt aaaacgtaga ggatttatat tcaaggatct caaaaaatgc gcgttttcat  10620

ttcactgcac atctagagga agagcagaaa cagagaattt cctagtccat cctattctga  10680

atggtgctgt ttctatattg gtcactgcct tgccaaacag gagctccggc acagagcgga  10740

agaaaccagc ctcagtgact tgaaagtgtc ctttcaggaa ggcggagctg cgttggtttg  10800

caatgttttt agttgacttt gacaaggggt tacgtgaaat tctgggtctc ttaagcatgc  10860

cctgtagctg gtttctcttt tacgtttgcc tctcctccca tccttttctt tccttttctt  10920

tatttctctt tacaattttt ttgagatcca tcctctatca agaagtctga agcgacttta  10980

aaggttttta aatttgtatt taaaaaccaa cttataaagc attgcaacaa ggttacctct  11040

attttgccac aagcgtctcg ggattgtgtt tgactcctgt ctgtccaaga acttttcccc  11100

caaagatgtg tatagttatt ggttaaaatg actgttttcg ctctttctgg aaataaagag  11160

gaaaaaggaa actttttttg tttgctcttg cattgcaaaa attataaaag taatttatta  11220

tttattgtca ggagacttgc cacttttcat gtcatttgac tttttttttg tttgctgaag  11280

taaaaagaag ataaaggttg taccgtggtc tttgaattat atgtctaagt ttatgtgttt  11340

tgtctttttt ttttctttaa atattatgtg aaatcaaagc gccatatgta gaattatatc  11400

ttcaggacta tttcactaat aaacgtttgg catagataat taaataaacg caatgattca  11460

gggtc                                                              11465


<210> SEQ ID NO 5
<211> LENGTH: 2526
<212> TYPE: DNA
<213> ORGANISM: mouse
<220> FEATURE:
<221> NAME/KEY: CDS
<222> LOCATION: (267)..(1316)

<400> SEQUENCE: 5

tttgagtaag agataaggaa gagaggtgcc ccgagccgtg cgagtccgcc gctgctgctg     60

cgcctccgct ctgccaactc cgccggctta aatcggactc ccagatctgc gagggcgcgg    120

cgcagccggg cagctgtttc ccccagtttt ggcaaccccg ggggccacta tttgccacct    180

agccacagca ccagcatcct ctctgtgggc tattcaccaa ttgtccaacc accatttcac    240

tgtggacatt actccctctt acagat atg gga gac atg ggc gat cca cca aaa     293
                             Met Gly Asp Met Gly Asp Pro Pro Lys
                             1               5

aaa aaa cgt ctg att tcc ctg tgt gtt ggt tgc ggc aat caa att cac      341
```

-continued

```
Lys Lys Arg Leu Ile Ser Leu Cys Val Gly Cys Gly Asn Gln Ile His
10                  15                  20                  25

gac cag tat att ctg agg gtt tct ccg gat ttg gag tgg cat gca gca      389
Asp Gln Tyr Ile Leu Arg Val Ser Pro Asp Leu Glu Trp His Ala Ala
                30                  35                  40

tgt ttg aaa tgt gcg gag tgt aat cag tat ttg gac gaa agc tgt acg      437
Cys Leu Lys Cys Ala Glu Cys Asn Gln Tyr Leu Asp Glu Ser Cys Thr
            45                  50                  55

tgc ttt gtt agg gat ggg aaa acc tac tgt aaa aga gat tat atc agg      485
Cys Phe Val Arg Asp Gly Lys Thr Tyr Cys Lys Arg Asp Tyr Ile Arg
        60                  65                  70

ttg tac ggg atc aaa tgc gcc aag tgc agc ata ggc ttc agc aag aac      533
Leu Tyr Gly Ile Lys Cys Ala Lys Cys Ser Ile Gly Phe Ser Lys Asn
    75                  80                  85

gac ttc gtg atg cgt gcc cgc tct aag gtg tac cac atc gag tgt ttc      581
Asp Phe Val Met Arg Ala Arg Ser Lys Val Tyr His Ile Glu Cys Phe
90                  95                  100                 105

cgc tgt gta gcc tgc agc cga cag ctc atc ccg gga gac gaa ttc gcc      629
Arg Cys Val Ala Cys Ser Arg Gln Leu Ile Pro Gly Asp Glu Phe Ala
                110                 115                 120

ctg cgg gag gat ggg ctt ttc tgc cgt gca gac cac gat gtg gtg gag      677
Leu Arg Glu Asp Gly Leu Phe Cys Arg Ala Asp His Asp Val Val Glu
            125                 130                 135

aga gcc agc ctg gga gct gga gac cct ctc agt ccc ttg cat cca gcg      725
Arg Ala Ser Leu Gly Ala Gly Asp Pro Leu Ser Pro Leu His Pro Ala
        140                 145                 150

cgg cct ctg caa atg gca gcc gaa ccc atc tcg gct agg cag cca gct      773
Arg Pro Leu Gln Met Ala Ala Glu Pro Ile Ser Ala Arg Gln Pro Ala
    155                 160                 165

ctg cgg ccg cac gtc cac aag cag ccg gag aag acc acc cga gtg cgg      821
Leu Arg Pro His Val His Lys Gln Pro Glu Lys Thr Thr Arg Val Arg
170                 175                 180                 185

act gtg ctc aac gag aag cag ctg cac acc ttg cgg acc tgc tat gcc      869
Thr Val Leu Asn Glu Lys Gln Leu His Thr Leu Arg Thr Cys Tyr Ala
                190                 195                 200

gcc aac cct cgg cca gat gcg ctc atg aag gag caa cta gtg gag atg      917
Ala Asn Pro Arg Pro Asp Ala Leu Met Lys Glu Gln Leu Val Glu Met
            205                 210                 215

acg ggc ctc agt ccc aga gtc atc cga gtg tgg ttt caa aac aag cgg      965
Thr Gly Leu Ser Pro Arg Val Ile Arg Val Trp Phe Gln Asn Lys Arg
        220                 225                 230

tgc aag gac aag aaa cgc agc atc atg atg aag cag ctc cag cag cag     1013
Cys Lys Asp Lys Lys Arg Ser Ile Met Met Lys Gln Leu Gln Gln Gln
    235                 240                 245

caa ccc aac gac aaa act aat atc cag ggg atg aca gga act ccc atg     1061
Gln Pro Asn Asp Lys Thr Asn Ile Gln Gly Met Thr Gly Thr Pro Met
250                 255                 260                 265

gtg gct gct agt ccg gag aga cat gat ggt ggt tta cag gct aac cca     1109
Val Ala Ala Ser Pro Glu Arg His Asp Gly Gly Leu Gln Ala Asn Pro
                270                 275                 280

gta gag gtg caa agt tac cag ccg ccc tgg aaa gta ctg agt gac ttc     1157
Val Glu Val Gln Ser Tyr Gln Pro Pro Trp Lys Val Leu Ser Asp Phe
            285                 290                 295

gcc ttg caa agc gac ata gat cag cct gct ttt cag caa ctg gtc aat     1205
Ala Leu Gln Ser Asp Ile Asp Gln Pro Ala Phe Gln Gln Leu Val Asn
        300                 305                 310

ttt tca gaa gga gga cca ggc tct aat tct act ggc agt gaa gta gca     1253
Phe Ser Glu Gly Gly Pro Gly Ser Asn Ser Thr Gly Ser Glu Val Ala
    315                 320                 325
```

```
tcg atg tcc tcg cag ctc cca gat aca ccc aac agc atg gta gcc agt      1301
Ser Met Ser Ser Gln Leu Pro Asp Thr Pro Asn Ser Met Val Ala Ser
330                 335                 340                 345

cct att gag gca tga ggaacattca ttcagatgtt ttgttttgtt ttgttttgtt      1356
Pro Ile Glu Ala

tttttcccct gttggagaaa gtgggaaatg acgttgaact ccgaaataaa aagtatttaa   1416

cgacccagtc aatggaaact gaatcaagaa atgaacgctc caggaagcgc atgaagtctg   1476

ttctaatgac aaagtgatat ggtagcaaca ctgtgaagac aatcatggga ttttactaga   1536

ataaaaacaa acaaacaaac aaaaccctaa gcccaacata tgctattcaa tgaccttagg   1596

agtacttaaa aaagaaaaag aaaaaaaaaa gagagagaga ccgtttttaa aacgtagagg   1656

atttatattc aaggatctca aaaaatgcgc gttttcattt cactgcacat ctagaggaag   1716

agcagaaaca gagaatttcc tagtccatcc tattctgaat ggtgctgttt ctatattggt   1776

cactgccttg ccaaacagga gctccggcac agagcggaag aaaccagcct cagtgacttg   1836

aaagtgtcct ttcaggaagg cggagctgcg ttggtttgca atgtttttag ttgactttga   1896

caaggggtta cgtgaaattc tgggtctctt aagcatgccc tgtagctggt ttctctttta   1956

cgtttgcctc tcctcccatc cttttctttc cttttcttta tttctcttta caattttttt   2016

gagatccatc ctctatcaag aagtctgaag cgactttaaa ggtttttaaa tttgtattta   2076

aaaaccaact tataaagcat tgcaacaagg ttacctctat tttgccacaa gcgtctcggg   2136

attgtgtttg actcctgtct gtccaagaac ttttccccca aagatgtgta tagttattgg   2196

ttaaaatgac tgttttcgct ctttctggaa ataaagagga aaaaggaaac tttttttgtt   2256

tgctcttgca ttgcaaaaat tataaaagta atttattatt tattgtcagg agacttgcca   2316

cttttcatgt catttgactt tttttttgtt tgctgaagta aaaagaagat aaaggttgta   2376

ccgtggtctt tgaattatat gtctaagttt atgtgttttg tcttttttttt ttctttaaat  2436

attatgtgaa atcaaagcgc catatgtaga attatatctt caggactatt tcactaataa   2496

acgtttggca tagataatta aataaacgca                                     2526


<210> SEQ ID NO 6
<211> LENGTH: 349
<212> TYPE: PRT
<213> ORGANISM: mouse

<400> SEQUENCE: 6

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45

Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125
```

```
Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
    290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
                325                 330                 335

Asp Thr Pro Asn Ser Met Val Ala Ser Pro Ile Glu Ala
            340                 345
```

<210> SEQ ID NO 7
<211> LENGTH: 5753
<212> TYPE: DNA
<213> ORGANISM: Homo sapiens

<400> SEQUENCE: 7

```
gctagtgcgt gttgacgtca tgctgcgtgc gggccggtgc ggaatcgctc cttcaactcc      60

gcggggcagt aggagttagt tagcaaagag ccgaggccgg gcgcgcgacc ctcgtccttc     120

tgcccctggc cgcacacttt gcgcacatct ctttttctgc atggtggata ttatttttca     180

ttatcctttt ctgggtgcta tgggtgatca ttccaagagt aagtatttct gtgtgtgtgt     240

ggggtggggt gtgtgtgtat gcttaatatg caaaatttct aatgcagaaa aatgtttagt     300

ggattctaca agtggcttct atttgtcaga atagtttagg agaggaaaaa cgaatgcatg     360

tctcctgcag gactgcttat ctttgggaat cctgttgttt tattttataa gtaaacacta     420

tttctcaagc cggctaggat gacttcgggc tgcgaaatct gcttctgttt tgcgcaaagg     480

caattaggtt tgatttaggg atgtgggttt tttttttttt ggttgttgtt tgtttgcctt     540

tcggtttttc aaagctagga agctttcttt cgcttgctct gggatattta aactaagaaa     600

tgtctgagag gatgagcggg gactgccgaa agacgatgtg tctgtgttgg gataggaggc     660

agccgctgtg agtgggagtg tgtgagcgga aatgccagga cagcaccgtt aggtgttgat     720

atccaggcgt ccgcagtgcc tgtgtattta ctctcttctt agtttcgtgt ttgcgtttag     780

tttcaagaca cgtcgacaaa acgactgtca ttaatgaatg taataacgaa atatttgggg     840

tgggggacag aagaaacctt cagcaatcca caagatactg gtttttcgtt tccaatgccc     900
```

tggaccttta gagagctcat catctttcct tatggtcgca agtcttgaaa gaaagagcaa 960
gagagcgagc gggttgggtt ggggctggag tagccgaggc cggcctgggt ccgggcagtc 1020
aggcctgacg cggccccgcg cccttccccg gcagagaagc ccgggacggc catgtgcgtg 1080
ggctgcggga gtcagatcca cgaccagttt atcctgcggg tgtcgcccga cctcgagtgg 1140
cacgcggcct gcctcaagtg tgccgagtgc agccagtacc tggacgagac gtgcacgtgc 1200
ttcgtgagag acgggaagac ctactgcaag cgggactatg tcaggtgagg ccggcgggaa 1260
cgcgggctgg gccaccgcgc gcaggggccg gggccgggac tggggatggc ggcctgcccg 1320
cgcgccccgg ccctgcccag ggagaaggcc atccgcatcc cgcacgggtg ccgcagcgct 1380
cccccgggcc cgggaatgcc cgcaggcggg tcaccgcagt ctcctggtgg ccacaaagtg 1440
tcctgggcgc gcgccggagc cgtagcagcc agggagatga gggcggccgc aggcccagcg 1500
ctgacaccgc cgcaccttgg gcccgcaggc tgttcggcat caagtgcgcc aagtgccagg 1560
tgggcttcag cagcagcgac ctggtgatga gggcgcggga cagcgtgtac cacatcgagt 1620
gcttccgctg ctccgtgtgc agccgccagc tgctgcctgg ggacgagttc tcgctgcggg 1680
agcacgagct gctctgccgc gccgaccacg gcctcctgct cgagcgcgcc gcggccggca 1740
gcccgcgcag ccccggcccg cttcccggcg cccgcggcct gcatctgccc ggtaagcgcg 1800
ccggggcctg tgccggggtg agcggggtgt atgtgcgtgc gtgtgtgtag gggtacgctt 1860
gtgtccctaa cgagaagttg tcagttgtgt gtggttccgt ctgccgggat agtgtttttc 1920
tgtatcagtg cggaactgtg tgctgggaac aaggctgtgt gtattctcgt gtgctcggga 1980
gaaactgcgt gtgtatgagt gtgtgagcac ggagaattgt gcagaatcgt gttctccatg 2040
accaggaaca tgcagggcac agtgctagga gcagaagagt ggatgacaac agggaatctt 2100
aagtggtgtc cgtcttgggg cttgtattag gaatttcttg gaggaatatg tgttattgtc 2160
agagggtaag gtttgcccag gggtatgtgt gtaagtaaca cagctccaaa ctgggagctg 2220
ggcaggagct tggtcagcca ggagccaaga acccaacaaa gaggggtttt tgccatcttg 2280
ttttgaggcc cagtttgatg aacaatttag ccaggttctt ctgggggagg gggagtatca 2340
atgcatagtg gactgtcact ggaatattct gggtcctaat cagcagctgc ccagagatgg 2400
ggtctgagtg tataatgggc aggtacggct gaacagaaac agaggtgcct ccaccccagg 2460
caaggcagtt tcccccaggt agccataggc ctgcagcaca gatccgtaga ccaggctggg 2520
cctctgggtg ctgtgtggcc ttgccccgct cctcccctct ctggatcttc acttcctccc 2580
tatagaaaga ggaaactggg ctggatgggc tatttgtaaa tatttgtcca gacctagaaa 2640
ttcgtagagg ggaacataaa ccgaaatggt gcagtacaga tccacggtat atatgggtcg 2700
ggatcaaatg gagatgtgaa atgggagcaa gcgggtattc agtgcacccc catctgggat 2760
ctcggagagg ctcccctttg tttgtttcgg gcttcagggt gcaggctctg gaatcagtca 2820
ctgtttcccc gggatggaga gaacctgggg ccaagcgagg agagtgccag cggctgctca 2880
gcaccttggt cggtgggagg ccactgggct ggggaacctg gagccttgag gaaggagaca 2940
ggggccgaag cccaagggcg ggcaggaagg aactgttgca agccctggag gcccgtccat 3000
aaccgtggat gagtcttcta cacatgtggc ctggccctgt ccaaatgggc tctgaaggag 3060
gggaagggcc ctcgtaggcc cccggcatat tcgcacctcc cacccagtcc cctgggcagc 3120
gcctcgccct gggtccacgt cggtcccttt ccctctccag agtcctgggc aagcctcttt 3180
cctcttcctc tgaaactccg acttcttccg gagggcttcg ctcgttccga gggtcctgcg 3240

-continued

```
actggaggag gcacatccct gagcagccac tccctccccg cagcggcctg tcgccgagct   3300
cccgcgccct gcttgagctc gggagagatc gctgcggggc agtccggccc gggagcgaga   3360
gaaagaacga aaatgcacag ctctctccga gtaaggcgaa cagatggaga ggaagacgaa   3420
caattaaacg aaacaaacag aataaaacag aaacgaaatc gggccccggg gggctgggcc   3480
acccggaggt tgggctcggg gcgggtgggt ggcggcccct cgctaacctc tggcctcacc   3540
ctgtcctggc agacgctggg tcgggccggc agcccgcgtt gcgcccgcac gtgcacaagc   3600
agacggagaa gacgacccgc gtgcggactg tgctgaacga gaagcagctg cacactctgc   3660
ggacctgcta cgccgccaac ccgcggcccg acgctctcat gaaggagcag ctggtggaga   3720
tgaccggcct gagcccgcgg gtcatccgcg tctggttcca gaacaagcgc tgcaaggaca   3780
agaagaaatc cattctcatg aagcagctgc agcagcagca gcacagcgac aagacggtga   3840
gcagccgctg ggccggaggc tcgagtcggg tgggggctgc gcttccgccg cggtatctgc   3900
gtgccctttt ctgggcgagc cctgggagat ccagggagaa ctgggcgctc cagatggtgt   3960
atgtctgtac cttcacagca aggcttccct tggatttgag gcttcctatt ttgtctggga   4020
tcggggtttc tccttgtccc agtggcagcc ccgcgttgcg ggttccgggc gctgcgcgga   4080
gcccaaggct gcatggcagt gtgcagcgcc cgccagtcgg gctggtgggt tgtgcactcc   4140
gtcggcagct gcagaaaggt gggagtgcag gtcttgcctt tcctcaccgg gcggttggct   4200
tccagcaccg aggctgacct atcgtggcaa gtttgcggcc cccgcagatc cccagtggag   4260
aaagagggct cttccgatgc gatcgagtgt gcgcctcccc gcaaagcaat gcagacccta   4320
aatcactcaa ggcctggagc tccagtctca aaggtggcag aaaaggccag acctaactcg   4380
agcacctact gccttctgct tgccccgcag agccttcagg gactgactgg gacgcccctg   4440
gtggcgggca gtcccatccg ccatgagaac gccgtgcagg gcagcgcagt ggaggtgcag   4500
acgtaccagc cgccgtggaa ggcgctcagc gagtttgccc tccagagcga cctggaccaa   4560
cccgccttcc aacagctggt gaggccctgc cctacccgcc ccgacctcgg gactctgcgg   4620
gttggggatt tagccactta gcctggcaga gaggggaggg ggtggccttg ggctgagggg   4680
ctgggtacag ccctaggcgg tgggggaggg ggaacagtgg cgggctctga aacctcacct   4740
cggcccatta cgcgccctaa accaggtctc cctggattaa agtgctcaca agagaggtcg   4800
caggattaac caacccgctc ccccgcccta atccccccct cgtgcgcctg gggacctggc   4860
ctccttctcc gcagggcttg ctctcagctg gcggccggtc cccaagggac actttccgac   4920
tcggagcacg cggccctgga gcaccagctc gcgtgcctct tcacctgcct cttcccggtg   4980
tttccgccgc cccaggtctc cttctccgag tccggctccc taggcaactc ctccggcagc   5040
gacgtgacct ccctgtcctc gcagctcccg gacaccccca acagtatggt gccgagtccc   5100
gtggagacgt gaggggggacc cctccctgcc agcccgcgga cctcgcatgc tccctgcatg   5160
agactcaccc atgctcaggc cattccagtt ccgaaagctc tctcgccttc gtaattattc   5220
tattgttatt tatgagagag taccgagaga cacggtctgg acagcccaag gcgccaggat   5280
gcaacctgct ttcaccagac tgcagacccc tgctccgagg actcttagtt tttcaaaacc   5340
agaatctggg acttaccagg gttagctctg ccctctcctc tcctctctac gtggccgccg   5400
ctctgtctct ccacgcccca cctgtgtccc catctcggcc ggcccggagc tcgcccacgc   5460
ggaccccccgc cctgccccag ctcagcgctc cctggcggct tcgcccgggc tcctagcggg   5520
gaaaaggaag gggataactc agaggaacag acactcaaac tcccaaagcg catgattgct   5580
gggaaacagt agaaaccaga cttgccttga aagtgtttaa gttattcgac ggaggacaga   5640
```

gtatgtgagc ctttgccgaa caaacaaacg taagttattg ttatttattg tgagaacagc 5700
cagttcatag tgggacttgt attttgatct taataaaaaa taataacccg ggg 5753

<210> SEQ ID NO 8
<211> LENGTH: 1918
<212> TYPE: DNA
<213> ORGANISM: Homo sapiens
<220> FEATURE:
<221> NAME/KEY: CDS
<222> LOCATION: (161)..(1240)

<400> SEQUENCE: 8

```
gctagtgcgt gttgacgtca tgctgcgtgc gggccggtgc ggaatcgctc cttcaactcc     60

gcggggcagt aggagttagt tagcaaagag ccgaggccgg gcgcgcgacc ctcgtccttc    120

tgcccctggc cgcacacttt gcgcacatct ctttttctgc atg gtg gat att att      175
                                            Met Val Asp Ile Ile
                                            1               5

ttt cat tat cct ttt ctg ggt gct atg ggt gat cat tcc aag aag aag      223
Phe His Tyr Pro Phe Leu Gly Ala Met Gly Asp His Ser Lys Lys Lys
                10                  15                  20

ccc ggg acg gcc atg tgc gtg ggc tgc ggg agt cag atc cac gac cag      271
Pro Gly Thr Ala Met Cys Val Gly Cys Gly Ser Gln Ile His Asp Gln
            25                  30                  35

ttt atc ctg cgg gtg tcg ccc gac ctc gag tgg cac gcg gcc tgc ctc      319
Phe Ile Leu Arg Val Ser Pro Asp Leu Glu Trp His Ala Ala Cys Leu
        40                  45                  50

aag tgt gcc gag tgc agc cag tac ctg gac gag acg tgc acg tgc ttc      367
Lys Cys Ala Glu Cys Ser Gln Tyr Leu Asp Glu Thr Cys Thr Cys Phe
    55                  60                  65

gtg aga gac ggg aag acc tac tgc aag cgg gac tat gtc agg ctg ttc      415
Val Arg Asp Gly Lys Thr Tyr Cys Lys Arg Asp Tyr Val Arg Leu Phe
70                  75                  80                  85

ggc atc aag tgc gcc aag tgc cag gtg ggc ttc agc agc agc gac ctg      463
Gly Ile Lys Cys Ala Lys Cys Gln Val Gly Phe Ser Ser Ser Asp Leu
                90                  95                  100

gtg atg agg gcg cgg gac agc gtg tac cac atc gag tgc ttc cgc tgc      511
Val Met Arg Ala Arg Asp Ser Val Tyr His Ile Glu Cys Phe Arg Cys
            105                 110                 115

tcc gtg tgc agc cgc cag ctg ctg cct ggg gac gag ttc tcg ctg cgg      559
Ser Val Cys Ser Arg Gln Leu Leu Pro Gly Asp Glu Phe Ser Leu Arg
        120                 125                 130

gag cac gag ctg ctc tgc cgc gcc gac cac ggc ctc ctg ctc gag cgc      607
Glu His Glu Leu Leu Cys Arg Ala Asp His Gly Leu Leu Leu Glu Arg
    135                 140                 145

gcc gcg gcc ggc agc ccg cgc agc ccc ggc ccg ctt ccc ggc gcc cgc      655
Ala Ala Ala Gly Ser Pro Arg Ser Pro Gly Pro Leu Pro Gly Ala Arg
150                 155                 160                 165

ggc ctg cat ctg ccc gac gct ggg tcg ggc cgg cag ccc gcg ttg cgc      703
Gly Leu His Leu Pro Asp Ala Gly Ser Gly Arg Gln Pro Ala Leu Arg
                170                 175                 180

ccg cac gtg cac aag cag acg gag aag acg acc cgc gtg cgg act gtg      751
Pro His Val His Lys Gln Thr Glu Lys Thr Thr Arg Val Arg Thr Val
            185                 190                 195

ctg aac gag aag cag ctg cac act ctg cgg acc tgc tac gcc gcc aac      799
Leu Asn Glu Lys Gln Leu His Thr Leu Arg Thr Cys Tyr Ala Ala Asn
        200                 205                 210

ccg cgg ccc gac gct ctc atg aag gag cag ctg gtg gag atg acc ggc      847
Pro Arg Pro Asp Ala Leu Met Lys Glu Gln Leu Val Glu Met Thr Gly
    215                 220                 225
```

```
ctg agc ccg cgg gtc atc cgc gtc tgg ttc cag aac aag cgc tgc aag      895
Leu Ser Pro Arg Val Ile Arg Val Trp Phe Gln Asn Lys Arg Cys Lys
230                 235                 240                 245

gac aag aag aaa tcc att ctc atg aag cag ctg cag cag cag cag cac      943
Asp Lys Lys Lys Ser Ile Leu Met Lys Gln Leu Gln Gln Gln Gln His
                250                 255                 260

agc gac aag acg agc ctt cag gga ctg act ggg acg ccc ctg gtg gcg      991
Ser Asp Lys Thr Ser Leu Gln Gly Leu Thr Gly Thr Pro Leu Val Ala
            265                 270                 275

ggc agt ccc atc cgc cat gag aac gcc gtg cag ggc agc gca gtg gag     1039
Gly Ser Pro Ile Arg His Glu Asn Ala Val Gln Gly Ser Ala Val Glu
        280                 285                 290

gtg cag acg tac cag ccg ccg tgg aag gcg ctc agc gag ttt gcc ctc     1087
Val Gln Thr Tyr Gln Pro Pro Trp Lys Ala Leu Ser Glu Phe Ala Leu
    295                 300                 305

cag agc gac ctg gac caa ccc gcc ttc caa cag ctg gtc tcc ttc tcc     1135
Gln Ser Asp Leu Asp Gln Pro Ala Phe Gln Gln Leu Val Ser Phe Ser
310                 315                 320                 325

gag tcc ggc tcc cta ggc aac tcc tcc ggc agc gac gtg acc tcc ctg     1183
Glu Ser Gly Ser Leu Gly Asn Ser Ser Gly Ser Asp Val Thr Ser Leu
                330                 335                 340

tcc tcg cag ctc ccg gac acc ccc aac agt atg gtg ccg agt ccc gtg     1231
Ser Ser Gln Leu Pro Asp Thr Pro Asn Ser Met Val Pro Ser Pro Val
            345                 350                 355

gag acg tga gggggacccc tccctgccag cccgcggacc tcgcatgctc             1280
Glu Thr

cctgcatgag actcacccat gctcaggcca ttccagttcc gaaagctctc tcgccttcgt   1340

aattattcta ttgttattta tgagagagta ccgagagaca cggtctggac agcccaaggc   1400

gccaggatgc aacctgcttt caccagactg cagacccctg ctccgaggac tcttagtttt   1460

tcaaaaccag aatctgggac ttaccagggt tagctctgcc ctctcctctc ctctctacgt   1520

ggccgccgct ctgtctctcc acgccccacc tgtgtcccca tctcggccgg cccggagctc   1580

gcccacgcgg acccccgccc tgccccagct cagcgctccc tggcggcttc gcccgggctc   1640

ctagcgggga aaaggaaggg gataactcag aggaacagac actcaaactc ccaaagcgca   1700

tgattgctgg gaaacagtag aaaccagact tgccttgaaa gtgtttaagt tattcgacgg   1760

aggacagagt atgtgagcct ttgccgaaca aacaaacgta agttattgtt atttattgtg   1820

agaacagcca gttcatagtg ggacttgtat tttgatctta ataaaaaata ataacccggg   1880

aaaaaaaaaa aaaaaaaaaa aaaaaaaaaa aaaaaaaa                           1918


<210> SEQ ID NO 9
<211> LENGTH: 359
<212> TYPE: PRT
<213> ORGANISM: Homo sapiens

<400> SEQUENCE: 9

Met Val Asp Ile Ile Phe His Tyr Pro Phe Leu Gly Ala Met Gly Asp
1               5                   10                  15

His Ser Lys Lys Lys Pro Gly Thr Ala Met Cys Val Gly Cys Gly Ser
            20                  25                  30

Gln Ile His Asp Gln Phe Ile Leu Arg Val Ser Pro Asp Leu Glu Trp
        35                  40                  45

His Ala Ala Cys Leu Lys Cys Ala Glu Cys Ser Gln Tyr Leu Asp Glu
    50                  55                  60

Thr Cys Thr Cys Phe Val Arg Asp Gly Lys Thr Tyr Cys Lys Arg Asp
```

```
65                  70                  75                  80

Tyr Val Arg Leu Phe Gly Ile Lys Cys Ala Lys Cys Gln Val Gly Phe
                85                  90                  95

Ser Ser Ser Asp Leu Val Met Arg Ala Arg Asp Ser Val Tyr His Ile
            100                 105                 110

Glu Cys Phe Arg Cys Ser Val Cys Ser Arg Gln Leu Leu Pro Gly Asp
        115                 120                 125

Glu Phe Ser Leu Arg Glu His Glu Leu Leu Cys Arg Ala Asp His Gly
    130                 135                 140

Leu Leu Leu Glu Arg Ala Ala Ala Gly Ser Pro Arg Ser Pro Gly Pro
145                 150                 155                 160

Leu Pro Gly Ala Arg Gly Leu His Leu Pro Asp Ala Gly Ser Gly Arg
                165                 170                 175

Gln Pro Ala Leu Arg Pro His Val His Lys Gln Thr Glu Lys Thr Thr
            180                 185                 190

Arg Val Arg Thr Val Leu Asn Glu Lys Gln Leu His Thr Leu Arg Thr
        195                 200                 205

Cys Tyr Ala Ala Asn Pro Arg Pro Asp Ala Leu Met Lys Glu Gln Leu
    210                 215                 220

Val Glu Met Thr Gly Leu Ser Pro Arg Val Ile Arg Val Trp Phe Gln
225                 230                 235                 240

Asn Lys Arg Cys Lys Asp Lys Lys Lys Ser Ile Leu Met Lys Gln Leu
                245                 250                 255

Gln Gln Gln Gln His Ser Asp Lys Thr Ser Leu Gln Gly Leu Thr Gly
            260                 265                 270

Thr Pro Leu Val Ala Gly Ser Pro Ile Arg His Glu Asn Ala Val Gln
        275                 280                 285

Gly Ser Ala Val Glu Val Gln Thr Tyr Gln Pro Pro Trp Lys Ala Leu
    290                 295                 300

Ser Glu Phe Ala Leu Gln Ser Asp Leu Asp Gln Pro Ala Phe Gln Gln
305                 310                 315                 320

Leu Val Ser Phe Ser Glu Ser Gly Ser Leu Gly Asn Ser Ser Gly Ser
                325                 330                 335

Asp Val Thr Ser Leu Ser Ser Gln Leu Pro Asp Thr Pro Asn Ser Met
            340                 345                 350

Val Pro Ser Pro Val Glu Thr
        355
```

<210> SEQ ID NO 10
<211> LENGTH: 1057
<212> TYPE: DNA
<213> ORGANISM: Homo sapiens

<400> SEQUENCE: 10

```
tgattggaca gcagcgaggt cccaccgggc gcctccgcgg cttaaaaccg aagcgggggc      60

gagggggagg tagagcccgc cccctgcgcg tcgcggctgg gagggagagg aggtgggaga     120

gaaggaagag gcggaggagg cagcgggcgc cgaggctctg ggacccgcag gcaagccaga     180

ccgacgcgca gagccgggag cctcatcgca gcggcagcgg cagcggcggg ctcgggccgg     240

cctcgggggc tgctcaccca catgagcatc cgcccacccg gcgagccccc gagcccaggc     300

ggcgcggcca tggccgagct caagtcgctg tcgggggacg cgtacctggc actaagccac     360

ggctacgcgg cggcggctgc gggtctcgcc tacggggcgg cgcgagaacc cgaagcggcc     420

cgcggctacg gcactccggg cccgggcggc gacctccccg cggcgcctgc acctcgcgcc     480
```

```
ccagctcagg cggcggagag cagcggcgaa cagagcgggg acgaggacga cgccttcgag    540

cagcggcggc ggcggcgcgg gccagggagc gcggcggacg ggcggcggcg gccgcgagag    600

cagcggtctc tgcggctcag catcaacgcg cgcgagcggc ggcgcatgca cgacctaaac    660

gacgcgctgg acgggctgcg agccgtcatc ccctacgcgc acagcccgtc ggtgcgcaag    720

ctctccaaga tcgccacgct gctgctcgcc aagaactata tcctcatgca ggcgcaggcc    780

ctggacgaga tgcggcgcct ggtggccttc ctcaaccagg gccagggcct ggccgcgccc    840

gtaaacgccg cgcccttgac gcccttcggc caggccactg tgtgcccctt ctccgcaggc    900

gccgccctgg ggccctgccc tgacaagtgc gccgccttct ccgggacgcc ctccgcgctt    960

tgcaaacact gtcacgagaa gccgtgaccg cgcgggcccc cggccctccc gcacgcgtcc   1020

tccgatcgcc cctgtgactg tctctctgcc cggacag                            1057


<210> SEQ ID NO 11
<211> LENGTH: 1057
<212> TYPE: DNA
<213> ORGANISM: Homo sapiens
<220> FEATURE:
<221> NAME/KEY: CDS
<222> LOCATION: (262)..(987)

<400> SEQUENCE: 11

tgattggaca gcagcgaggt cccaccgggc gcctccgcgg cttaaaaccg aagcgggggc     60

gagggggagg tagagcccgc cccctgcgcg tcgcggctgg gagggagagg aggtgggaga    120

gaaggaagag gcggaggagg cagcgggcgc cgaggctctg ggacccgcag gcaagccaga    180

ccgacgcgca gagccgggag cctcatcgca gcggcagcgg cagcggcggg ctcgggccgg    240

cctcgggggc tgctcaccca c atg agc atc cgc cca ccc ggc gag ccc ccg      291
                        Met Ser Ile Arg Pro Pro Gly Glu Pro Pro
                        1               5                   10

agc cca ggc ggc gcg gcc atg gcc gag ctc aag tcg ctg tcg ggg gac      339
Ser Pro Gly Gly Ala Ala Met Ala Glu Leu Lys Ser Leu Ser Gly Asp
                15                  20                  25

gcg tac ctg gca cta agc cac ggc tac gcg gcg gcg gct gcg ggt ctc      387
Ala Tyr Leu Ala Leu Ser His Gly Tyr Ala Ala Ala Ala Ala Gly Leu
            30                  35                  40

gcc tac ggg gcg gcg cga gaa ccc gaa gcg gcc cgc ggc tac ggc act      435
Ala Tyr Gly Ala Ala Arg Glu Pro Glu Ala Ala Arg Gly Tyr Gly Thr
        45                  50                  55

ccg ggc ccg ggc ggc gac ctc ccc gcg gcg cct gca cct cgc gcc cca      483
Pro Gly Pro Gly Gly Asp Leu Pro Ala Ala Pro Ala Pro Arg Ala Pro
    60                  65                  70

gct cag gcg gcg gag agc agc ggc gaa cag agc ggg gac gag gac gac      531
Ala Gln Ala Ala Glu Ser Ser Gly Glu Gln Ser Gly Asp Glu Asp Asp
75                  80                  85                  90

gcc ttc gag cag cgg cgg cgg cgg cgc ggg cca ggg agc gcg gcg gac      579
Ala Phe Glu Gln Arg Arg Arg Arg Arg Gly Pro Gly Ser Ala Ala Asp
                95                  100                 105

ggg cgg cgg cgg ccg cga gag cag cgg tct ctg cgg ctc agc atc aac      627
Gly Arg Arg Arg Pro Arg Glu Gln Arg Ser Leu Arg Leu Ser Ile Asn
            110                 115                 120

gcg cgc gag cgg cgg cgc atg cac gac cta aac gac gcg ctg gac ggg      675
Ala Arg Glu Arg Arg Arg Met His Asp Leu Asn Asp Ala Leu Asp Gly
        125                 130                 135

ctg cga gcc gtc atc ccc tac gcg cac agc ccg tcg gtg cgc aag ctc      723
Leu Arg Ala Val Ile Pro Tyr Ala His Ser Pro Ser Val Arg Lys Leu
    140                 145                 150
```

```
tcc aag atc gcc acg ctg ctg ctc gcc aag aac tat atc ctc atg cag      771
Ser Lys Ile Ala Thr Leu Leu Leu Ala Lys Asn Tyr Ile Leu Met Gln
155                 160                 165                 170

gcg cag gcc ctg gac gag atg cgg cgc ctg gtg gcc ttc ctc aac cag      819
Ala Gln Ala Leu Asp Glu Met Arg Arg Leu Val Ala Phe Leu Asn Gln
                175                 180                 185

ggc cag ggc ctg gcc gcg ccc gta aac gcc gcg ccc ttg acg ccc ttc      867
Gly Gln Gly Leu Ala Ala Pro Val Asn Ala Ala Pro Leu Thr Pro Phe
            190                 195                 200

ggc cag gcc act gtg tgc ccc ttc tcc gca ggc gcc gcc ctg ggg ccc      915
Gly Gln Ala Thr Val Cys Pro Phe Ser Ala Gly Ala Ala Leu Gly Pro
        205                 210                 215

tgc cct gac aag tgc gcc gcc ttc tcc ggg acg ccc tcc gcg ctt tgc      963
Cys Pro Asp Lys Cys Ala Ala Phe Ser Gly Thr Pro Ser Ala Leu Cys
    220                 225                 230

aaa cac tgt cac gag aag ccg tga ccgcgcgggc ccccggccct cccgcacgcg    1017
Lys His Cys His Glu Lys Pro
235                 240

tcctccgatc gcccctgtga ctgtctctct gcccggacag                         1057


<210> SEQ ID NO 12
<211> LENGTH: 241
<212> TYPE: PRT
<213> ORGANISM: Homo sapiens

<400> SEQUENCE: 12

Met Ser Ile Arg Pro Pro Gly Glu Pro Pro Ser Pro Gly Gly Ala Ala
1               5                   10                  15

Met Ala Glu Leu Lys Ser Leu Ser Gly Asp Ala Tyr Leu Ala Leu Ser
            20                  25                  30

His Gly Tyr Ala Ala Ala Ala Ala Gly Leu Ala Tyr Gly Ala Ala Arg
        35                  40                  45

Glu Pro Glu Ala Ala Arg Gly Tyr Gly Thr Pro Gly Pro Gly Gly Asp
    50                  55                  60

Leu Pro Ala Ala Pro Ala Pro Arg Ala Pro Ala Gln Ala Ala Glu Ser
65                  70                  75                  80

Ser Gly Glu Gln Ser Gly Asp Glu Asp Asp Ala Phe Glu Gln Arg Arg
                85                  90                  95

Arg Arg Arg Gly Pro Gly Ser Ala Ala Asp Gly Arg Arg Arg Pro Arg
            100                 105                 110

Glu Gln Arg Ser Leu Arg Leu Ser Ile Asn Ala Arg Glu Arg Arg Arg
        115                 120                 125

Met His Asp Leu Asn Asp Ala Leu Asp Gly Leu Arg Ala Val Ile Pro
    130                 135                 140

Tyr Ala His Ser Pro Ser Val Arg Lys Leu Ser Lys Ile Ala Thr Leu
145                 150                 155                 160

Leu Leu Ala Lys Asn Tyr Ile Leu Met Gln Ala Gln Ala Leu Asp Glu
                165                 170                 175

Met Arg Arg Leu Val Ala Phe Leu Asn Gln Gly Gln Gly Leu Ala Ala
            180                 185                 190

Pro Val Asn Ala Ala Pro Leu Thr Pro Phe Gly Gln Ala Thr Val Cys
        195                 200                 205

Pro Phe Ser Ala Gly Ala Ala Leu Gly Pro Cys Pro Asp Lys Cys Ala
    210                 215                 220

Ala Phe Ser Gly Thr Pro Ser Ala Leu Cys Lys His Cys His Glu Lys
225                 230                 235                 240
```

Pro

<210> SEQ ID NO 13
<211> LENGTH: 2520
<212> TYPE: DNA
<213> ORGANISM: Mouse

<400> SEQUENCE: 13
agagcggccc cggccggcca cgcgccttgg tgagaaggcg caggaagggt ggccggccgg 60
agaggccacg cgcaggcccg gggactgaca gacagctgga caggtggacg cgcccgcagg 120
gcaagaagcc atactgccgt agcgggctcc agaggtcatg gccgagctca agtcgctgtc 180
gggggactcg tacctggcgc tgagccacag ctacacggcg accggccacg cctacgctgc 240
agcgcgcgga ccggagacca cacgcggctt cggtgcatcg ggtccgggtg gcgacctccc 300
ggcggctccc gcttctcgtg tccccgccgc gacggtggag agcagcggcg agcagagcgg 360
cgacgaggac gaagccttcg agaggcggcg gcggcggcga gggtccgggg ttgcggttga 420
cgcacggcgg cggccccggg agcagcgctc gctgaggctc agcatcaacg cgcgcgaacg 480
gcgacgcatg catgacctga acgacgcgct ggacggactg cgcgcagtca tcccctacgc 540
gcacagcccg tcggtgcgca agctctccaa gatagccaca cttctgctgg ccaaaaacta 600
catcctcatg caggcgcagg ccctggagga gatgcggcgc ttggtagcat acctcaacca 660
aggccagggc ctcgcggcgc cggtggccgc cgcgcctcta acgccctttg gccaggcagc 720
gatttacccg ttctcggcgg gcaccgcgct cgggccctgc ccagacaagt gtgccacctt 780
ctcaggatcg ccctcggcgc tttgcaaaca ctgcggcgag aagccctgag ggctccgatc 840
ccctctgcag ccgcctttct atttagactg ttccctgtcc tcgctggcgg gactctatga 900
gaaagcccag tactccgctt acagaactgt tgggtgcaga atgagaagtc cgtctgagaa 960
agccagagag ttggcgctgg actctagacc ctgccgcatc cactgaacta tctcagctaa 1020
aaggctacgg gagtgagcag ttagtgaatg gtcccacatc tgacaggtga ctgcccaagg 1080
ctcaggagcg caggcacaga gcatcgcgct tgaccacatc ctagcgttgg atggggaacc 1140
cagccccttc taagccaact tgcagggcct tgcttgcttc aactagacct gttcctcagg 1200
acgggtgcgg cccctcacct cggcctctg ttggctccaa gactccagac ccggcctaaa 1260
agcaaaatta cgccgaggtc ctttggagag gtcgtggagg cagacgcagg aagatcccag 1320
gaggtgagct ttacaacgtt ttccaagtct gagcttgttc tgttaacatt cttgcctgcc 1380
cagaggctca ggaaattcaa gccagcctca aaagtctgtg gaaacatctc taaataagcc 1440
tggagcgcca ccgccggcct cctgtgggct gagctgggtt tcacttcttt ctacttgtcc 1500
caaggggact ggtggagccc tcacaacctg ctcagggcta cttgaccctg gagggtcagc 1560
cgaagagtct agtctagctc caggaccaac caagtcccct ctgcgccagt tcgggaactt 1620
ctggaggaag ccgggctacc ggtgagtacc cggtgaggtg ttggactgaa tgggaactgg 1680
tcgctcccca aatcggacca cagcccagaa tcctgccact gtacctagtc tgagccttag 1740
cccgcgcgtc tcagatgttg cctggttttc ctctgtggcc atcagcagct tccgcctcca 1800
tttacccagt tttcttggct ttcattgatg caaagcaaat cgggagaggg ccactgctca 1860
gcaaagcgcc tgtctatagc gcttaacttg aattaacgca ttggaaaagg cccttttgta 1920
tttgcaaaat gacgtgtgtg attaagtctt attcataaag acgtatgctt aatactggtt 1980
tctgctaatt tctatttttt atttcttaag tgtctttccc ctcccctaaa ataatctatt 2040

-continued ttgcacattt caaaacagac tgtttttcaa gttcgcttaa gatgaacagg gaaaactgga 2100
aactcaagtg ttgttagctc tggggtcatt acccactatt atttttcaaa gtcttttatt 2160
tatatttaga cgaggggtag tgtgcagaat aaagtactta aaacttattt ttttaaaaat 2220
atgattaaaa tttaatatca aattaagtgt acatctatga tttgattcat aatttcaatt 2280
gtcagacagt gatactggtt tggaatcctt ctacggcccc aagaaatgct gagattttac 2340
aatggatcca tactccatta agagatgtgt gagttcatac gaaaaatgtg taggagtgtt 2400
gggtggagac acaggggtga tcccaacctg caggaggcag agacaggggc atggggattc 2460
tgagaccagc ctgagcaaca cagggaggct ctcttaggac aagaaaacaa ttaactttga 2520

<210> SEQ ID NO 14
<211> LENGTH: 2520
<212> TYPE: DNA
<213> ORGANISM: mouse
<220> FEATURE:
<221> NAME/KEY: CDS
<222> LOCATION: (158)..(829)

<400> SEQUENCE: 14
agagcggccc cggccggcca cgcgccttgg tgagaaggcg caggaagggt ggccggccgg 60
agaggccacg cgcaggcccg gggactgaca gacagctgga caggtggacg cgcccgcagg 120
gcaagaagcc atactgccgt agcgggctcc agaggtc atg gcc gag ctc aag tcg 175
Met Ala Glu Leu Lys Ser
1 5 ctg tcg ggg gac tcg tac ctg gcg ctg agc cac agc tac acg gcg acc 223
Leu Ser Gly Asp Ser Tyr Leu Ala Leu Ser His Ser Tyr Thr Ala Thr
10 15 20 ggc cac gcc tac gct gca gcg cgc gga ccg gag acc aca cgc ggc ttc 271
Gly His Ala Tyr Ala Ala Ala Arg Gly Pro Glu Thr Thr Arg Gly Phe
25 30 35 ggt gca tcg ggt ccg ggt ggc gac ctc ccg gcg gct ccc gct tct cgt 319
Gly Ala Ser Gly Pro Gly Gly Asp Leu Pro Ala Ala Pro Ala Ser Arg
40 45 50 gtc ccc gcc gcg acg gtg gag agc agc ggc gag cag agc ggc gac gag 367
Val Pro Ala Ala Thr Val Glu Ser Ser Gly Glu Gln Ser Gly Asp Glu
55 60 65 70 gac gaa gcc ttc gag agg cgg cgg cgg cgg cga ggg tcc ggg gtt gcg 415
Asp Glu Ala Phe Glu Arg Arg Arg Arg Arg Arg Gly Ser Gly Val Ala
75 80 85 gtt gac gca cgg cgg cgg ccc cgg gag cag cgc tcg ctg agg ctc agc 463
Val Asp Ala Arg Arg Arg Pro Arg Glu Gln Arg Ser Leu Arg Leu Ser
90 95 100 atc aac gcg cgc gaa cgg cga cgc atg cat gac ctg aac gac gcg ctg 511
Ile Asn Ala Arg Glu Arg Arg Arg Met His Asp Leu Asn Asp Ala Leu
105 110 115 gac gga ctg cgc gca gtc atc ccc tac gcg cac agc ccg tcg gtg cgc 559
Asp Gly Leu Arg Ala Val Ile Pro Tyr Ala His Ser Pro Ser Val Arg
120 125 130 aag ctc tcc aag ata gcc aca ctt ctg ctg gcc aaa aac tac atc ctc 607
Lys Leu Ser Lys Ile Ala Thr Leu Leu Leu Ala Lys Asn Tyr Ile Leu
135 140 145 150 atg cag gcg cag gcc ctg gag gag atg cgg cgc ttg gta gca tac ctc 655
Met Gln Ala Gln Ala Leu Glu Glu Met Arg Arg Leu Val Ala Tyr Leu
155 160 165 aac caa ggc cag ggc ctc gcg gcg ccg gtg gcc gcc gcg cct cta acg 703
Asn Gln Gly Gln Gly Leu Ala Ala Pro Val Ala Ala Ala Pro Leu Thr
170 175 180

-continued

```
ccc ttt ggc cag gca gcg att tac ccg ttc tcg gcg ggc acc gcg ctc      751
Pro Phe Gly Gln Ala Ala Ile Tyr Pro Phe Ser Ala Gly Thr Ala Leu
        185                 190                 195

ggg ccc tgc cca gac aag tgt gcc acc ttc tca gga tcg ccc tcg gcg      799
Gly Pro Cys Pro Asp Lys Cys Ala Thr Phe Ser Gly Ser Pro Ser Ala
    200                 205                 210

ctt tgc aaa cac tgc ggc gag aag ccc tga gggctccgat cccctctgca        849
Leu Cys Lys His Cys Gly Glu Lys Pro
215                 220

gccgcctttc tatttagact gttccctgtc ctcgctggcg ggactctatg agaaagccca    909

gtactccgct tacagaactg ttgggtgcag aatgagaagt ccgtctgaga aagccagaga    969

gttggcgctg gactctagac cctgccgcat ccactgaact atctcagcta aaaggctacg   1029

ggagtgagca gttagtgaat ggtcccacat ctgacaggtg actgcccaag gctcaggagc   1089

gcaggcacag agcatcgcgc ttgaccacat cctagcgttg gatggggaac ccagcccctt   1149

ctaagccaac ttgcagggcc ttgcttgctt caactagacc tgttcctcag gacgggtgcg   1209

gcccctcacc tcgggcctct gttggctcca agactccaga cccggcctaa aagcaaaatt   1269

acgccgaggt cctttggaga ggtcgtggag gcagacgcag gaagatccca ggaggtgagc   1329

tttacaacgt tttccaagtc tgagcttgtt ctgttaacat tcttgcctgc ccagaggctc   1389

aggaaattca agccagcctc aaaagtctgt ggaaacatct ctaaataagc ctggagcgcc   1449

accgccggcc tcctgtgggc tgagctgggt ttcacttctt tctacttgtc ccaaggggac   1509

tggtggagcc ctcacaacct gctcagggct acttgaccct ggagggtcag ccgaagagtc   1569

tagtctagct ccaggaccaa ccaagtcccc tctgcgccag ttcgggaact tctggaggaa   1629

gccgggctac cggtgagtac ccggtgaggt gttggactga atgggaactg gtcgctcccc   1689

aaatcggacc acagcccaga atcctgccac tgtacctagt ctgagcctta gcccgcgcgt   1749

ctcagatgtt gcctggtttt cctctgtggc catcagcagc ttccgcctcc atttacccag   1809

ttttcttggc tttcattgat gcaaagcaaa tcgggagagg gccactgctc agcaaagcgc   1869

ctgtctatag cgcttaactt gaattaacgc attggaaaag gccctttgt atttgcaaaa   1929

tgacgtgtgt gattaagtct tattcataaa gacgtatgct taatactggt ttctgctaat   1989

ttctattttt tatttcttaa gtgtctttcc cctcccctaa aataatctat tttgcacatt   2049

tcaaaacaga ctgtttttca agttcgctta agatgaacag ggaaaactgg aaactcaagt   2109

gttgttagct ctggggtcat tacccactat tatttttcaa agtcttttat ttatatttag   2169

acgaggggta gtgtgcagaa taaagtactt aaaacttatt tttttaaaaa tatgattaaa   2229

atttaatatc aaattaagtg tacatctatg atttgattca taatttcaat tgtcagacag   2289

tgatactggt ttggaatcct tctacggccc caagaaatgc tgagatttta caatggatcc   2349

atactccatt aagagatgtg tgagttcata cgaaaaatgt gtaggagtgt tgggtggaga   2409

cacaggggtg atcccaacct gcaggaggca gagacagggg catggggatt ctgagaccag   2469

cctgagcaac acagggaggc tctcttagga caagaaaaca attaactttg a            2520


<210> SEQ ID NO 15
<211> LENGTH: 223
<212> TYPE: PRT
<213> ORGANISM: mouse

<400> SEQUENCE: 15

Met Ala Glu Leu Lys Ser Leu Ser Gly Asp Ser Tyr Leu Ala Leu Ser
1               5                   10                  15
```

-continued

```
His Ser Tyr Thr Ala Thr Gly His Ala Tyr Ala Ala Ala Arg Gly Pro
            20                  25                  30

Glu Thr Thr Arg Gly Phe Gly Ala Ser Gly Pro Gly Gly Asp Leu Pro
        35                  40                  45

Ala Ala Pro Ala Ser Arg Val Pro Ala Ala Thr Val Glu Ser Ser Gly
    50                  55                  60

Glu Gln Ser Gly Asp Glu Asp Glu Ala Phe Glu Arg Arg Arg Arg Arg
65                  70                  75                  80

Arg Gly Ser Gly Val Ala Val Asp Ala Arg Arg Arg Pro Arg Glu Gln
                85                  90                  95

Arg Ser Leu Arg Leu Ser Ile Asn Ala Arg Glu Arg Arg Arg Met His
            100                 105                 110

Asp Leu Asn Asp Ala Leu Asp Gly Leu Arg Ala Val Ile Pro Tyr Ala
        115                 120                 125

His Ser Pro Ser Val Arg Lys Leu Ser Lys Ile Ala Thr Leu Leu Leu
    130                 135                 140

Ala Lys Asn Tyr Ile Leu Met Gln Ala Gln Ala Leu Glu Glu Met Arg
145                 150                 155                 160

Arg Leu Val Ala Tyr Leu Asn Gln Gly Gln Gly Leu Ala Ala Pro Val
                165                 170                 175

Ala Ala Ala Pro Leu Thr Pro Phe Gly Gln Ala Ala Ile Tyr Pro Phe
            180                 185                 190

Ser Ala Gly Thr Ala Leu Gly Pro Cys Pro Asp Lys Cys Ala Thr Phe
        195                 200                 205

Ser Gly Ser Pro Ser Ala Leu Cys Lys His Cys Gly Glu Lys Pro
    210                 215                 220
```

<210> SEQ ID NO 16
<211> LENGTH: 20
<212> TYPE: DNA
<213> ORGANISM: Artificial Sequence
<220> FEATURE:
<223> OTHER INFORMATION: gRNA for Bhlhb4

<400> SEQUENCE: 16
ccgagctcaa gtcgctgtcg 20

<210> SEQ ID NO 17
<211> LENGTH: 20
<212> TYPE: DNA
<213> ORGANISM: Artificial Sequence
<220> FEATURE:
<223> OTHER INFORMATION: gRNA for Bhlhb4

<400> SEQUENCE: 17
cgcgccttgg tgagaaggcg 20

<210> SEQ ID NO 18
<211> LENGTH: 20
<212> TYPE: DNA
<213> ORGANISM: Artificial Sequence
<220> FEATURE:
<223> OTHER INFORMATION: gRNA for mouse ISL1

<400> SEQUENCE: 18
tcttcaatag cacgcgggaa 20

<210> SEQ ID NO 19
<211> LENGTH: 20
<212> TYPE: DNA

-continued

```
<213> ORGANISM: Artificial Sequence
<220> FEATURE:
<223> OTHER INFORMATION: gRNA for mouse ISL1

<400> SEQUENCE: 19

tcctaagcca taaagcgctt                                              20


<210> SEQ ID NO 20
<211> LENGTH: 20
<212> TYPE: DNA
<213> ORGANISM: Artificial Sequence
<220> FEATURE:
<223> OTHER INFORMATION: gRNA for Human ISL1

<400> SEQUENCE: 20

ccaactccgc cggcttaaat                                              20


<210> SEQ ID NO 21
<211> LENGTH: 20
<212> TYPE: DNA
<213> ORGANISM: Artificial Sequence
<220> FEATURE:
<223> OTHER INFORMATION: gRNA for Human ISL1

<400> SEQUENCE: 21

gggaggttaa tacttcggag                                              20


<210> SEQ ID NO 22
<211> LENGTH: 27
<212> TYPE: DNA
<213> ORGANISM: Artificial Sequence
<220> FEATURE:
<223> OTHER INFORMATION: synthetic construct_Fig. 6B control

<400> SEQUENCE: 22

tccgccggct taaattggac tcctaga                                      27


<210> SEQ ID NO 23
<211> LENGTH: 28
<212> TYPE: DNA
<213> ORGANISM: Artificial Sequence
<220> FEATURE:
<223> OTHER INFORMATION: synthetic construct_Fig. 6B No. 16

<400> SEQUENCE: 23

tccgccggct taggagaggg agtgaaag                                     28


<210> SEQ ID NO 24
<211> LENGTH: 27
<212> TYPE: DNA
<213> ORGANISM: Artificial Sequence
<220> FEATURE:
<223> OTHER INFORMATION: synthetic construct_Fig. 6B No. 19

<400> SEQUENCE: 24

tccgccggct tagagaggga gtgaaag                                      27
```